(12) United States Patent
Baram et al.

(10) Patent No.: US 12,258,599 B2
(45) Date of Patent: Mar. 25, 2025

(54) **METHOD TO INACTIVATE A MUTANT ALLELE OF AN *ELANE* GENE**

(71) Applicant: EmendoBio Inc., Wilmington, DE (US)

(72) Inventors: David Baram, Tel Aviv (IL); Lior Izhar, Tel Aviv (IL); Asael Herman, Ness-Ziona (IL); Rafi Emmanuel, Ramla (IL); Liat Rockah, Rishon LeZion (IL); Nadav Marbach-Bar, Rehovot (IL); Michal Golan Mashiach, Ness-Ziona (IL); Joseph Georgeson, Rehovot (IL)

(73) Assignee: EmendoBio Inc., Wilmington, DE (US)

( * ) Notice: Subject to any disclaimer, the term of this patent is extended or adjusted under 35 U.S.C. 154(b) by 649 days.

(21) Appl. No.: 17/090,814

(22) Filed: Nov. 5, 2020

(65) Prior Publication Data
US 2021/0130804 A1 May 6, 2021

Related U.S. Application Data

(60) Provisional application No. 62/931,655, filed on Nov. 6, 2019.

(51) Int. Cl.
*C12N 9/22* (2006.01)
*C12N 9/64* (2006.01)
*C12N 15/11* (2006.01)

(52) U.S. Cl.
CPC .............. *C12N 9/6448* (2013.01); *C12N 9/22* (2013.01); *C12N 15/111* (2013.01); *C12N 2310/20* (2017.05)

(58) Field of Classification Search
CPC ...... C12N 9/6448; C12N 9/22; C12N 15/111; C12N 2310/20; C12N 2310/315; C12N 2310/321; C12N 15/113
See application file for complete search history.

(56) References Cited

U.S. PATENT DOCUMENTS

| | | |
|---|---|---|
| 2011/0023143 A1 | 1/2011 | Weinstein et al. |
| 2018/0155688 A1 | 6/2018 | Seet et al. |
| 2019/0024086 A1 | 1/2019 | Lande et al. |
| 2019/0264232 A1* | 8/2019 | Hou ..................... C12N 15/113 |
| 2021/0155929 A1 | 5/2021 | Baram |
| 2021/0363547 A1 | 11/2021 | Baram |
| 2022/0387515 A1 | 12/2022 | Baram |

FOREIGN PATENT DOCUMENTS

| | | |
|---|---|---|
| WO | WO 2018/085460 A2 | 5/2018 |
| WO | WO 2019/217294 A1 | 11/2019 |
| WO | WO 2020/112979 A2 | 6/2020 |
| WO | WO 2023/281083 A1 | 1/2023 |

OTHER PUBLICATIONS

Deng et al., Genes Genomes Genetics 6:205-207, 2016.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Mullins et al., Hypertension 22(4):630-633, 1993.*
Houdebine, J., Journal of Biotechnology 98:145-160, 2002.*
Phillips, A., J. Pharm. Pharmacology 53:1169-1174, 2001.*
Gardlik et al., Med. Sci. Monit. 11(4):RA110-121, 2005.*
Wang et al., ChemBioChem 20:634-643, 2019.*
Nasri et al., Haematologica 105(3):598-609, pre-published Jun. 27, 2019.*
DbSNP reference SNP report rs1057520110, Sep. 21, 2022.*
Hequet, O., Journal of Blood Medicine 6:55-67, 2015.*
Makaryan et al. (Curr Opin Hematol 22:3-11, 2015.*
Zou et al., GenBank accession No. RHS40773 Sep. 6, 2018.*
International Search Report issued Mar. 31, 2021 in connection with PCT International Application No. PCT/US2020/059186.
Written Opinion (form PCT/ISA/237) issued Mar. 31, 2021 in connection with PCT International Application No. PCT/US2020/059186.
Arun et al., "Spectrum of ELANE mutations in congenital neutropenia: a single-centre study in patients of Indian origin." Journal of Clinical Pathology, Aug. 31, 2018, vol. 71, iss. 12, pp. 1046-1051.

* cited by examiner

*Primary Examiner* — Delia M Ramirez
(74) *Attorney, Agent, or Firm* — Potomac Law Group, PLLC; Jamaica Potts Szeliga

(57) ABSTRACT

Methods for inactivating in a cell a mutant allele of the elastase, neutrophil expressed gene (ELANE gene) gene having a mutation associated with severe congenital neutropenia (SCN) or cyclic neutropenia (CyN) wherein the mutant allele is selected from the group consisting of the ELANE mutants set forth in Table 1, the method comprising
  introducing to the cell a composition comprising:
    a CRISPR nuclease or a sequence encoding the CRISPR nuclease; and
    a first RNA molecule comprising a guide sequence portion having 17-30 nucleotides,
  wherein a complex of the CRISPR nuclease and the first RNA molecule affects a double strand break in the mutant allele of the ELANE gene
the method optionally further comprising introduction of a second RNA molecule comprising a guide sequence portion capable of complexing with a CRISPR nuclease, wherein the complex of the second RNA molecule and CRISPR nuclease affects a second double strand break in the ELANE gene.

8 Claims, 5 Drawing Sheets
Specification includes a Sequence Listing.

OMNI-50

On-target g35 5' AGTCCGGGCTGGGAGCGGGTGGGGAGCA (SEQ ID NO: 31231)

On-target g62 5' GTCAAGCCCCAGAGGCCACAGGGACAGA (SEQ ID NO: 31232)

Off-target g35 5' AGTCCTGGCTGGGAGCAGGTGGGGAGAG (SEQ ID NO: 31233)

Off-target g62 5' GCCAAGCCTCAGAGGCCACAGGGCAGCA (SEQ ID NO: 31234)

METHOD TO INACTIVATE A MUTANT ALLELE OF AN *ELANE* GENE

This application claims the benefit of U.S. Provisional Application No. 62/931,655 filed Nov. 6, 2019, the contents of which are hereby incorporated by reference.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference nucleotide sequences which are present in the file named "201105_91192-A_Sequence_Listing_AWG.txt", which is 6,022 kilobytes in size, and which was created on Oct. 14, 2020 in the IBM-PC machine format, having an operating system compatibility with MS-Windows, which is contained in the text file filed Nov. 5, 2020 as part of this application.

BACKGROUND OF INVENTION

A genetic disorder is caused by one or more abnormalities in the genome. Genetic disorders may be regarded as either "dominant" or "recessive." Recessive genetic disorders are those which require two copies (i.e., two alleles) of the abnormal/defective gene to be present. In contrast, a dominant genetic disorder involves a gene or genes which exhibit(s) dominance over a normal (functional/healthy) gene or genes. As such, in dominant genetic disorders only a single copy (i.e., allele) of an abnormal gene is required to cause or contribute to the symptoms of a particular genetic disorder. Such mutations include, for example, gain-of-function mutations in which the altered gene product possesses a new molecular function or a new pattern of gene expression. Gain-of-function mutations are generally dominant negative mutations. An example of a dominant negative mutation is haploinsufficiency where one allele is mutated and loses its function and the single wild type allele left does not generate enough protein to be sufficient for a specific cellular function. Other examples include dominant negative mutations which have a gene product that acts antagonistically to the wild-type allele.

Neutropenia

Neutropenia is defined as a reduction in the absolute number of neutrophils in the blood circulation and commonly diagnosed by measuring the absolute neutrophil count (ANC) in peripheral blood. The severity of neutropenia is characterized as mild with an ANC of 1000-1500/µL, moderate with an ANC of 500-1000/µL, or severe with an ANC of less than 500/µL (Boxer 2012).

Neutropenia can be classified as congenital (hereditary) or acquired. The two main types of the congenital condition, commonly of autosomal dominant inheritance, are cyclic neutropenia (CyN) and severe congenital neutropenia (SCN). Cyclic neutropenia is characterized by fluctuating neutrophil counts from normal levels to zero while severe congenital neutropenia (SCN) is characterized by very low ANC (500/µL) observed at birth, maturation arrest of the myelopoiesis in bone marrow at the promyelocyte/myelocyte stage, and early onset of bacterial infections (Carlsson et al. 2012; Horwitz et al. 2013).

SCN may be diagnosed by measuring a very low ANC in the blood and examining bone marrow aspirate to identify myeloid maturation arrest (Dale 2017). SCN is usually diagnosed before age 6 months, while diagnosis for CyN is generally raised during the second year of life, or later, and the main clinical manifestation is recurrent acute stomatologic disorders. Bone marrow examination is often necessary to rule out malignant hemopathies, determine cellularity, assess myeloid maturation, and detect signs of a precise etiology, with cytogenetic bone marrow studies now crucial when SCN is suspected. Antineutrophil antibody assay, immunoglobulin assay (Ig GAM), lymphocyte immunophenotyping, pancreatic markers (serum trypsinogen and fecal elastase) and liposoluble vitamin levels (vitamins A, E and D) are also of interest in assessing SCN and CyN (See Donadieu 2011).

SCN can be autosomal-recessive (HAX1, G6PC3), autosomal-dominant (ELANE, GFI1), or X-linked (WAS) forms of inheritance or occur sporadically (Carlsson et al. 2012; Boxer 2012). Cyclic and congenital neutropenia are most frequently caused by mutations in the "elastase, neutrophil expressed gene" (ELANE gene)—the gene for neutrophil elastase. "ELANE gene mutations are identified in 40-55% of SCN patients and males and females are equally affected (Donadieu et al. 2011; Dale 2017). Mutations in the ELANE gene are associated with autosomal-dominant and sporadic cases of SCN (Carlsson et al. 2012). To date, more than 200 different ELANE mutations have been identified, which are randomly distributed over all exons as well as in intron 3 and intron 4 (Skokowa et al. 2017). More than 120 distinct ELANE gene mutations related to CyN and SCN are now known, for example C151Y and G214R particularly associated with a poor prognosis. (See Makaryan et al. 2012; see also Germeshausen et al. 2013 for a comprehensive list of ELANE mutations related to CyN and SCN).

ELANE encodes neutrophil elastase (NE) which is involved in the function of neutrophil extracellular traps (networks of fibers that bind pathogens). Some studies suggest that the product of mutant ELANE acts to disrupt neutrophil production in the bone marrow and cause neutropenia. These studies indicate that mutations in NE initiate the unfolded protein response (UPR) leading to cell loss in the process of neutrophil formation in the marrow (Makaryan et al. 2017).

Current Treatments

Granulocyte colony-stimulating factor (G-CSF) is considered the first-line treatment for SCN (Connelly, Choi, and Levine 2012). G-CSF stimulates the production of more neutrophils and delays their apoptosis (Schiffer and Klein 2007). Overall survival is now estimated to exceed 80%, including patients developing malignancies, although 10% of SCN patients still die from severe bacterial infections or sepsis (Skokowa et al. 2017). Although G-CSF therapy is successful in preventing mortality from sepsis, long-term treatment was identified to be associated with an increased risk of developing myelodysplastic syndrome (MDS) or leukemia in SCN patients. The most common leukemia in SCN is AML, but acute lymphoid leukemia (ALL), juvenile myelomonocytic leukemia (JMML), chronic myelomonocytic leukemia (CMML), and bi-phenotypic leukemia are also reported in the literature (Connelly, Choi, and Levine 2012). It was previously demonstrated that patients who had a robust response to G-CSF (doses≤8 µg/kg/day) had a cumulative incidence of 15% for developing MDS/leukemia after 15 years on G-CSF, while an incidence of 34% was reported in patients with poor response to G-CSF despite high doses (Rosenberg et al. 2010).

Hematopoietic stem cell transplant (HSCT) is an alternative, curative therapy for patients who do not respond to G-CSF therapy or who develop AML/MDS. However, patients with chronic neutropenia who undergo HCT are at increased risk of developing infectious complications such as fungal and graft-versus-host disease (Skokowa et al. 2017). Moreover, HCT requires a matched related donor for successful survival but most patients will not have an available matched donor (Connelly, Choi, and Levine 2012).

SUMMARY OF THE INVENTION

Disclosed is an approach for knocking out the expression of a dominant-mutant allele by disrupting the dominant-mutant allele or degrading the resulting mRNA.

Embodiments of the present invention provide methods for knocking out expression of a mutant allele of the elastase, neutrophil expressed gene (ELANE gene) gene having a mutation associated with severe congenital neutropenia (SCN) or cyclic neutropenia (CyN) and allowing expression of the functional protein.

The present invention provides a method for inactivating in a cell a mutant allele of the elastase, neutrophil expressed gene (ELANE gene) gene having a mutation associated with severe congenital neutropenia (SCN) or cyclic neutropenia (CyN), wherein the mutant allele is selected from the group consisting of the ELANE mutants set forth in Table 1, the method comprising
  introducing to the cell a composition comprising:
    a CRISPR nuclease or a sequence encoding the CRISPR nuclease; and
    a first RNA molecule comprising a guide sequence portion having 17-30 nucleotides,
  wherein a complex of the CRISPR nuclease and the first RNA molecule affects a double strand break in the mutant allele of the ELANE gene.

The present invention provides for a modified cell obtained by the methods of the present invention.

The present invention provides for a modified cell lacking at least a portion of one allele of the ELANE gene.

The present invention provides for a composition comprising modified cells and a pharmaceutically acceptable carrier.

The present invention provides for an in vitro or ex vivo method of preparing a composition, comprising mixing the cells of the present invention with the pharmaceutically acceptable carrier.

The present invention provides for a method of preparing in vitro or ex vivo a composition comprising modified cells, the method comprising:
  a) isolating HSPCs from cells obtained from a subject with an ELANE gene mutation related to SCN or CyN and/or suffering from SCN or CyN and which subject has a mutant allele of the ELANE gene selected from the group consisting of the ELANE mutants set forth in Table 1, and obtaining the cell from the subject;
  b) introducing to the cells of step (a) a composition comprising:
    a CRISPR nuclease or a sequence encoding the CRISPR nuclease; and
    a first RNA molecule comprising a guide sequence portion having 17-30 nucleotides,
    wherein a complex of the CRISPR nuclease and the first RNA molecule affects a double strand break in the mutant allele of the ELANE gene in one or more cells,
    optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally
  c) culture expanding the modified cells of step (b),
  wherein the modified cells are capable of engraftment and giving rise to progeny cells after engraftment.

The present invention provides for use of a composition prepared in vitro by a method comprising:
  a) isolating HSPCs from cells obtained from a subject with an ELANE gene mutation related to SCN or CyN and/or suffering from SCN or CyN and subject has a mutant allele of the ELANE gene selected from the group consisting of the ELANE mutants set forth in Table 1;
  b) introducing to the cells of step (a) a composition comprising:
    a CRISPR nuclease or a sequence encoding the CRISPR nuclease; and
    a first RNA molecule comprising a guide sequence portion having 17-30 nucleotides,
    wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally;
  c) culture expanding the cells of step (b) wherein the modified cells are capable of engraftment and giving rise to progeny cells after engraftment; and
  d) administering to the subject the cells of step (b) or step (c)
  for treating the SCN or CyN in the subject.

The present invention provides for a method of treating a subject afflicted with SCN or CyN, comprising administration of a therapeutically effective amount of the modified cells, compositions, or the compositions prepared by the methods of the instant invention The present invention provides for a method for treating SCN or CyN in a subject with an ELANE gene mutation relating to SCN or CYN in need thereof and which subject has a mutant allele of the ELANE gene selected from the group consisting of the ELANE mutants set forth in Table 1, the method comprising:
  a) isolating HSPCs from cells obtained from the subject;
  b) introducing to the cells of step (a) a composition comprising:
    a CRISPR nuclease or a sequence encoding the CRISPR nuclease; and
    a first RNA molecule comprising a guide sequence portion having 17-30 nucleotides,
    wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally;
c) culture expanding the cells of step (b) wherein the modified cells are capable of engraftment and giving rise to progeny cells after engraftment; and
d) administering to the subject the cells of step (b) or step (c)

thereby treating the SCN or CyN in the subject.

The present invention provides for a method for treating SCN or CyN in a subject with an ELANE gene mutation relating to SCN or CYN in need thereof and subject has a mutant allele of the ELANE gene selected from the group consisting of the ELANE mutants set forth in Table 1, the method comprising administering to the subject autologous modified cells or progeny of autologous modified cells, wherein the autologous modified cells are modified so as to have a double strand break in the mutant allele of the ELANE gene, wherein said double strand break results from introduction to the cells of a composition comprising a CRISPR nuclease or a sequence encoding the CRISPR nuclease and a first RNA molecule wherein a complex of the CRISPR nuclease and the first RNA molecule affects a double strand break in the mutant allele of the ELANE gene so as to inactive the mutant allele of the ELANE gene in the cell, thereby treating the SCN or CyN in the subject.

The present invention provides for a method of selecting a subject for treatment from a pool of subjects diagnosed with SCN or CyN, comprising the steps of:
a) obtaining cells from each subject in the pool of subjects;
b) screening each subject's cells for an ELANE gene mutation related to SCN or CyN, and selecting only subjects with an ELANE gene mutation related to SCN or CyN;
c) screening by sequencing the cells of the subjects selected in step (b) for a mutant allele of the ELANE gene selected from the group consisting of the ELANE mutations set forth in Table 1,
d) selecting for treatment only subjects with cells heterozygous for an ELANE mutation set forth in Table 1
e) obtaining hematopoetic stem and progenitor cells (HSPC) cells from the bone marrow of the subject either by aspiration or by mobilization and apheresis of peripheral blood; and
f) introducing to the HSPC cells of step (e):
one or more CRISPR nucleases or sequences encoding the one or more CRISPR nuclease;
a first RNA molecule comprising a guide sequence portion having 17-30 contiguous nucleotides containing nucleotides in the sequence set forth in any one of SEQ ID NOs: 1-31117 targeting the mutant allele of the ELANE gene, and
a second RNA molecule comprising a guide sequence portion targeting a sequence in intron 3, intron 4 or 3' UTR of the ELANE gene,
wherein a complex of the first RNA molecule and a CRISPR nuclease affects a first double strand break in the mutant allele of the ELANE gene in one or more of the HSPC cells and a complex of the second RNA molecule and a CRISPR nuclease affect a second double strand break in intron 3, intron 4, or 3' UTR of both alleles of the ELANE gene in the one or more HSPC cells in which the complex of the first RNA molecule and the CRISPR nuclease affected a first double strand break, thereby obtaining modified cells;
g) administering to the subject the modified cells of step (f), thereby treating SCN or CyN in the subject.

The present invention provides an RNA molecule comprising a guide sequence portion having 17-30 contiguous nucleotides containing nucleotides in the sequence set forth in any one of SEQ ID NOs: 1-31117.

The present invention provides a method for inactivating in a cell a mutant ELANE allele, the method comprising delivering to the cell the RNA molecules or compositions of the present invention.

The present invention provides use of the RNA molecules, the compositions, or the composition prepared by the method of the present invention for inactivating in a cell a mutant ELANE allele.

The present invention provides a medicament comprising the RNA molecules, compositions, or the compositions prepared by the methods of the instant invention for use in inactivating in a cell a mutant ELANE allele, wherein the medicament is administered by delivering to the cell the RNA molecules, compositions, or the compositions prepared by the methods of the instant invention.

The present invention provides for use of the methods, the modified cells, the compositions, or the compositions prepared by the methods, or the RNA molecules of the instant invention for treating ameliorating or preventing SCN or CyN in to a subject having or at risk of having SCN or CyN.

The present invention provides for a medicament comprising the RNA molecules, compositions, compositions prepared by the methods of the instant invention, or the modified cells of the instant invention, for use in treating ameliorating or preventing SCN or CyN, wherein the medicament is administered by delivering to a subject having or at risk of having SCN or CyN the RNA molecules, compositions, compositions prepared by the methods of the instant invention, or the modified cells of the instant invention.

The present invention provides for a kit for inactivating a mutant ELANE allele in a cell, comprising the RNA molecules of the instant invention, a CRISPR nuclease or a sequence encoding the CRISPR nuclease, and/or a tracrRNA molecule or a sequence encoding the tracrRNA; and instructions for delivering the RNA molecule; CRISPR nuclease or sequence encoding the CRISPR nuclease, and/or tracrRNA molecule or sequence encoding the tracrRNA to the cell to inactivate the mutant ELANE allele in the cell.

The present invention provides for a kit for treating SCN or CyN in a subject, comprising the RNA molecules of the instant invention, a CRISPR nuclease or sequence encoding the CRISPR nuclease, and/or a tracrRNA molecule or sequence encoding the tracrRNA molecule; and instructions for delivering the RNA molecule; CRISPR nuclease, and/or the tracrRNA to a subject having or at risk of having SCN or CyN so as to treat the SCN or CyN.

The present invention provides a kit for inactivating a mutant ELANE allele in a cell, comprising the compositions, the composition prepared by the methods of the instant invention, or the modified cells of the instant invention, and instructions for delivering the composition to the cell so as to inactivate the ELANE gene in the cell.

The present invention provides a kit for treating SCN or CyN in a subject, comprising the composition, the compositions prepared by the methods of the instant invention, or the modified cells of the instant invention, and instructions for delivering the compositions, the compositions prepared by the methods of the instant invention, or the modified cells of the instant invention, to a subject having or at risk of having SCN or CyN so as to treat SCN or CyN.

BRIEF DESCRIPTION OF THE DRAWINGS

FIG. 3A: Activity assay of OMNI-50 RNP with different spacer lengths (17-23 nucleotides) of guide 35 (Table 4). FIG. 3B: Reducing amounts of RNPs (4, 2, 1.2, 0.6 and 0.2 pmol) with spacer lengths 20-23 nucleotides were incubated with 100 ng of DNA target template. FIG. 3C: Activity assay for OMNI-50 as RNP in U2OS cells: RNPs with spacer lengths 17-23 nucleotides were electroporated into a U2OS cell line and editing levels (indels) were measured by NGS. FIG. 3D: Activity assay for OMNI-50 as RNP in U2OS cells: RNPs with ELANE g35 sgRNA V1-4 were electroporated into a U2OS cell line and editing levels (indels) were measured by NGS.

DETAILED DESCRIPTION

Figure 1:
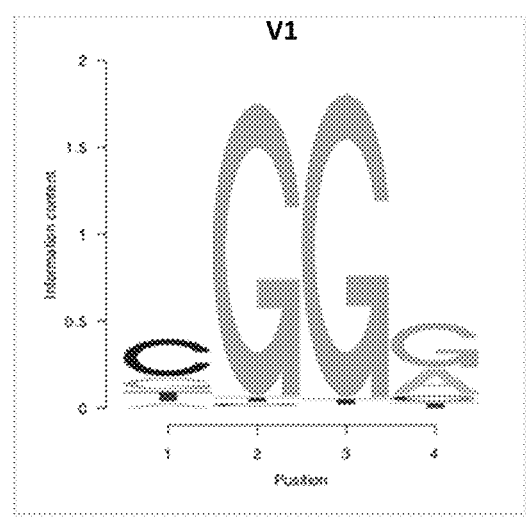
FIG. 1: In-vitro PAM Depletion by TXTL results for OMNI-50. The OMNI-50 nuclease was challenged with two versions of sgRNA with targeting spacer (T2) and non-targeting spacer (T1). The PAM logo is a schematic representation of the ratio of the depleted site. A table with the tested sgRNA version is presented for the most depleted reads with their ratio comparing to the non-targeted library.
Figure 1:
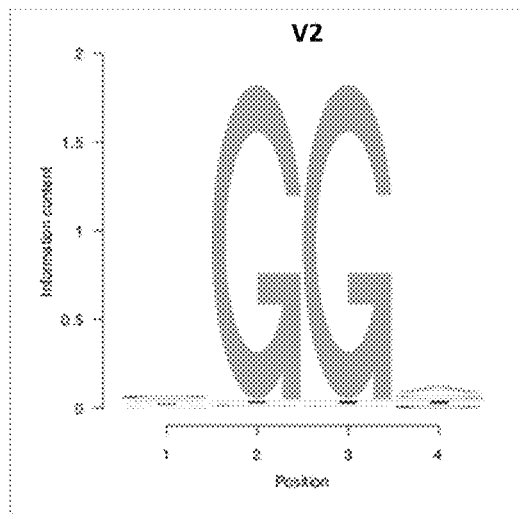

Embodiments of the present invention provide a method for inactivating in a cell a mutant allele of the elastase, neutrophil expressed gene (ELANE gene) gene having a mutation associated with severe congenital neutropenia (SCN) or cyclic neutropenia (CyN) wherein the mutant allele is selected from the group consisting of the ELANE mutants set forth in Table 1, the method comprising
    introducing to the cell a composition comprising:
        a CRISPR nuclease or a sequence encoding the CRISPR nuclease; and
        a first RNA molecule comprising a guide sequence portion having 17-30 nucleotides,
    wherein a complex of the CRISPR nuclease and the first RNA molecule affects a double strand break in the mutant allele of the ELANE gene.

In embodiments of the present invention, the guide sequence portion of the first RNA molecule comprises 17-22 contiguous nucleotides as set forth in any one of SEQ ID NOs: 1-31117.

In embodiments of the present invention, the complex of the CRISPR nuclease and the first RNA molecule affects a double strand break in the mutant allele of the ELANE gene, wherein the mutation associated with severe congenital neutropenia (SCN) or cyclic neutropenia (CyN) in mutant allele is targeted for the double strand break by the complex of the CRISPR nuclease and the first RNA molecule.

In embodiments of the present invention, the CRISPR nuclease and the first RNA molecule affects a double strand break in the mutant allele of the ELANE gene, which mutant allele is targeted for the double strand break based on a sequence of the mutant allele at the mutation associated with severe congenital neutropenia (SCN) or cyclic neutropenia (CyN).

In embodiments of the present invention, the CRISPR nuclease and the first RNA molecule affects a double strand break in the mutant allele of the ELANE based on the nucleotide base of the mutation associated with severe congenital neutropenia (SCN) or cyclic neutropenia (CyN) present on the mutant allele of the ELANE gene.

Embodiments of the present invention further comprise introduction of a second RNA molecule comprising a guide sequence portion capable of complexing with a CRISPR nuclease, wherein the complex of the second RNA molecule and CRISPR nuclease affects a second double strand break in the ELANE gene.

In embodiments of the present invention, a composition may comprise 1, 2, 3 or more CRISPR nucleases or sequencing encoding the CRISPR nucleases. In embodiments of the present invention, introducing a composition to the cell may comprise introducing 1, 2, 3, or more compositions to the cell. In embodiments of the present invention, each composition may comprise a different CRISPR nuclease or sequence encoding the CRISPR nucleases or the same CRISPR nuclease or sequence encoding the CRISPR nuclease. In embodiments of the present invention involving two RNA molecules, the second RNA molecule may form a complex with the same CRISPR nuclease as the first RNA molecule, or may form a complex with another CRISPR nuclease.

In embodiments of the present invention, the second double strand break is within a non-coding region of the ELANE gene. In embodiments of the present invention, the non-coding region of the ELANE gene is selected an intron or an untranslated region (UTR). In embodiments of the present invention, the non-coding region is in intron 3 or intron 4. In an embodiments of the present invention the UTR is the 3'UTR.

In embodiments of the present invention, the guide sequence portion of the first RNA molecule comprises 17-22 contiguous nucleotides as set forth in any one of SEQ ID NOs: 1-31117.

According to embodiments of the present invention, the guide sequence portion of the second RNA molecule comprises 17-30 contiguous nucleotides containing nucleotides in the sequence set forth in any one of SEQ ID NOs: 1-31117.

In embodiments of the present invention, the second double strand break is within a non-coding region of the ELANE gene.

Embodiments of the present invention comprise obtaining the cell with an ELANE gene mutation associated with severe congenital neutropenia (SCN) or CyN from a subject with an ELANE gene mutation related to SCN or CyN and/or suffering from SCN or CyN wherein the ELANE gene mutation is selected from the group consisting of the ELANE mutants set forth in Table 1.

Embodiments of the present invention comprise first selecting a subject with an ELANE gene mutation related to SCN or CyN and/or suffering from SCN or CyN wherein the ELANE gene mutation is selected from the group consisting of the ELANE mutants set forth in Table 1, and obtaining the cell from the subject.

Embodiments of the present invention comprise obtaining the cell from the subject by mobilization and/or by apheresis.

Embodiments of the present invention comprise obtaining the cell from the subject by bone marrow aspiration.

In embodiments of the present invention, the cell is prestimulated prior to introducing the composition to the cell.

Embodiments of the present invention comprise culture expanding the cell to obtain cells.

In embodiments of the present invention, the cells are cultured with one or more of: stem cell factor (SCF), IL-3, and GM-CSF.

In embodiments of the present invention, the cells are cultured with at least one cytokine.

In embodiments of the present invention, the at least one cytokine is a recombinant human cytokine.

In embodiments of the present invention, the cell is among a plurality of cells, wherein the composition comprising the first RNA molecule or both the first and the second RNA molecule is introduced into at least the cell as well as other cells among the plurality of cells, and the mutant allele of the ELANE gene is inactivated in at least the cell as well as in the other cells among the plurality of cells, thereby obtaining multiple modified cells.

In embodiments of the present invention, introducing the composition comprising the first RNA molecule or introduction of the second RNA molecule comprises electroporation of the cell or cells.

Embodiments of the present invention provide for a modified cell obtained by the methods of the present invention.

In embodiments of the present invention, the modified cells are further culture expanded.

In embodiments of the present invention, the modified cells are capable of engraftment.

In embodiments of the invention, modified cells are capable of long-term engraftment when infused into a patient, giving rise to differentiated hematopoietic cells for at least 12 months after infusion, preferably at least 24 months and even more preferably at least 30 months after infusion. In a further embodiment, the modified cells are capable of long-term engraftment when infused into an autologous subject. In a further embodiment, the modified cells are capable of long-term engraftment when infused into a subject without myeloablation. In an embodiment of the present invention, the modified cells are delivered to a subject in sufficient numbers that, when engrafted into a human subject, provide long term engraftment.

In embodiments of the present invention, the modified cell or cells are capable of giving rise to progeny cells.

In embodiments of the present invention, the modified cell or cells are capable of giving rise to progeny cells after engraftment.

In embodiments of the present invention, the modified cell or cells are capable of giving rise to progeny cells after an autologous engraftment.

In embodiments of the present invention, the modified cell or cells are capable of giving rise to progeny cells for at least 12 months or at least 24 months after engraftment.

In one embodiment, the cell or cells are stem cells. In one embodiment, the cell is an embryonic stem cell. In some embodiment, the stem cell is a hematopoietic stem/progenitor cell (HSPC).

In embodiments of the present invention, the modified cell or cells are CD34+ hematopoietic stem cells.

In embodiments of the present invention, the modified cell or cells are bone marrow cells or peripheral mononucleated cells (PMCs).

Embodiments of the present invention provide for a modified cell lacking at least a portion of one allele of the ELANE gene.

In embodiments of the present invention, the modified cell was modified from a cell with an ELANE gene mutation selected from the group consisting of the ELANE mutants set forth in Table 1.

Embodiments of the present invention provide for a composition comprising modified cells and a pharmaceutically acceptable carrier.

Embodiments of the present invention provide for an in vitro or ex vivo method of preparing a composition, comprising mixing the cells of the present invention with the pharmaceutically acceptable carrier.

Embodiments of the present invention provide for a method of preparing in vitro or ex vivo a composition comprising modified cells, the method comprising:
 a) isolating HSPCs from cells obtained from a subject with an ELANE gene mutation related to SCN or CyN and/or suffering from SCN or CyN, wherein the ELANE gene mutation is selected from the group consisting of the ELANE mutants set forth in Table 1, and obtaining the cell from the subject;
 b) introducing to the cells of step (a) a composition comprising:
  a CRISPR nuclease or a sequence encoding the CRISPR nuclease; and
  a first RNA molecule comprising a guide sequence portion having 17-30 nucleotides,
  wherein a complex of the CRISPR nuclease and the first RNA molecule affects a double strand break in the mutant allele of the ELANE gene in one or more cells,
  optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally
 c) culture expanding the modified cells of step (b),
  wherein the modified cells are capable of engraftment and giving rise to progeny cells after engraftment.

Embodiments of the present invention provide for use of a composition prepared in vitro by a method comprising:
 a) isolating HSPCs from cells obtained from a subject with an ELANE gene mutation related to SCN or CyN and/or suffering from SCN or CyN wherein the ELANE gene mutation is selected from the group consisting of the ELANE mutants set forth in Table 1;
b) introducing to the cells of step (a) a composition comprising:
   a CRISPR nuclease or a sequence encoding the CRISPR nuclease; and
   a first RNA molecule comprising a guide sequence portion having 17-30 nucleotides,
   wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally;
c) culture expanding the cells of step (b) wherein the modified cells are capable of engraftment and giving rise to progeny cells after engraftment; and
d) administering to the subject the cells of step (b) or step (c)
for treating the SCN or CyN in the subject.

Embodiments of the present invention provide for a method of treating a subject afflicted with SCN or CyN, comprising administration of a therapeutically effective amount of the modified cells, compositions, or the compositions prepared by the methods of the instant invention Embodiments of the present invention provide for a method for treating SCN or CyN in a subject with an ELANE gene mutation relating to SCN or CYN in need thereof wherein the ELANE gene mutation is selected from the group consisting of the ELANE mutants set forth in Table 1, the method comprising:
a) isolating HSPCs from cells obtained from the subject;
b) introducing to the cells of step (a) a composition comprising:
   a CRISPR nuclease or a sequence encoding the CRISPR nuclease; and
   a first RNA molecule comprising a guide sequence portion having 17-30 nucleotides,
   wherein a complex of the CRISPR nuclease and the first RNA molecule affects a double strand break in the mutant allele of the ELANE gene in one or more cells,
   optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally;
c) culture expanding the cells of step (b) wherein the modified cells are capable of engraftment and giving rise to progeny cells after engraftment; and
d) administering to the subject the cells of step (b) or step (c)
thereby treating the SCN or CyN in the subject.

Embodiments of the present invention provide for a method for treating SCN or CyN in a subject with an ELANE gene mutation relating to SCN or CYN in need thereof wherein the ELANE gene mutation is selected from the group consisting of the ELANE mutants set forth in Table 1, the method comprising
administering to the subject autologous modified cells or progeny of autologous modified cells, wherein the autologous modified cells are modified so as to have a double strand break in the mutant allele of the ELANE gene,
   wherein said double strand break results from introduction to the cells of a composition comprising a CRISPR nuclease or a sequence encoding the CRISPR nuclease and a first RNA molecule wherein a complex of the CRISPR nuclease and the first RNA molecule affects a double strand break in the mutant allele of the ELANE gene so as to inactive the mutant allele of the ELANE gene in the cell, thereby treating the SCN or CyN in the subject.

Embodiments of the present invention provide for a method of selecting a subject for treatment from a pool of subjects diagnosed with SCN or CyN, comprising the steps of:
a) obtaining cells from each subject in the pool of subjects;
b) screening each subject's cells for an ELANE gene mutation related to SCN or CyN, and selecting only subjects with an ELANE gene mutation related to SCN or CyN;
c) screening by sequencing the cells of the subjects selected in step (b) for a mutant allele of the ELANE gene selected from the group consisting of the ELANE mutations set forth in Table 1,
d) selecting for treatment only subjects with cells heterozygous for an ELANE mutation set forth in Table 1.
e) obtaining HSPC cells from the bone marrow of the subject either by aspiration or by mobilization and apheresis of peripheral blood; and
f) introducing to the HSPC cells of step (e):
   one or more CRISPR nucleases or sequences encoding the one or more CRISPR nucleases
   a first RNA molecule comprising a guide sequence portion having 17-30 contiguous nucleotides containing nucleotides in the sequence set forth in any one of SEQ ID NOs: 1-31117 targeting the mutant allele of the ELANE gene, and
   a second RNA molecule comprising a guide sequence portion targeting a sequence in intron 3, intron 4 or 3' UTR of the ELANE gene,
   wherein a complex of the first RNA molecule and a CRISPR nuclease affects a first double strand break in the mutant allele of the ELANE gene in one or more of the HSPC cells and a complex of the second RNA molecule and a CRISPR nuclease affect a second double strand break in intron 3, intron 4, or 3' UTR of both alleles of the ELANE gene in the one or more HSPC cells in which the complex of the first RNA molecule and the CRISPR nuclease affected a first double strand break, thereby obtaining modified cells;
g) administering to the subject the modified cells of step (f),
thereby treating SCN or CyN in the subject.

Embodiments of the present invention provide an RNA molecule comprising a guide sequence portion having 17-30 contiguous nucleotides containing nucleotides in the sequence set forth in any one of SEQ ID NOs: 1-31117.

Embodiments of the present invention further comprise a second RNA molecule comprising a guide sequence portion.

In embodiments of the present invention, the second RNA molecule targets a non-coding region of the ELANE gene.

In embodiments of the present invention, the nucleotide sequence of the guide sequence portion of the second RNA molecule is a different nucleotide sequence from the sequence of the guide sequence portion of the first RNA molecule.

In embodiments of the present invention, the first RNA molecule further comprise a portion having a sequence which binds to a CRISPR nuclease. In embodiments of the present invention, the second RNA molecule further comprise a portion having a sequence which binds to a CRISPR nuclease.

In an embodiment of the present invention:
a. the CRISPR nuclease has at least 100%, 99%, 98%, 97%, 96%, 95%, 94%, 93%, 92%, 91%, 90%, 85%, 80% identity to SEQ ID NO: 31123, and the sequence which binds to a CRISPR nuclease comprises a sequence selected from SEQ ID NOs: 31151 to 31160;
b. the CRISPR nuclease has at least 100%, 99%, 98%, 97%, 96%, 95%, 94%, 93%, 92%, 91%, 90%, 85%, 80% identity to SEQ ID NO: 31124, and the sequence which binds to a CRISPR nuclease comprises a sequence selected from SEQ ID NOs: 31161 to 31170;
c. the CRISPR nuclease has at least 100%, 99%, 98%, 97%, 96%, 95%, 94%, 93%, 92%, 91%, 90%, 85%, 80% identity to SEQ ID NO: 31125, and the sequence which binds to a CRISPR nuclease comprises a sequence selected from SEQ ID NOs: 31171 to 31181; or
d. the CRISPR nuclease has at least 100%, 99%, 98%, 97%, 96%, 95%, 94%, 93%, 92%, 91%, 90%, 85%, 80% identity to SEQ ID NO: 31126, and the sequence which binds to a CRISPR nuclease comprises a sequence selected from SEQ ID NOs: 31182 to 31189 and GGAUUAUCC.

In embodiments of the present invention, the sequence which binds to a CRISPR nuclease is a tracrRNA sequence.

In embodiments of the present invention, the first RNA molecule further comprises a portion having a tracr mate sequence. In embodiments of the present invention, the second RNA molecule further comprises a portion having a tracr mate sequence.

In embodiments of the present invention, the first RNA molecule further comprises one or more linker portions. In embodiments of the present invention, the second RNA molecule further comprises one or more linker portions.

In embodiments of the present invention, the first RNA molecule is up to 300 nucleotides in length. In embodiments of the present invention, the second RNA molecule is up to 300 nucleotides in length.

In embodiments of the present invention, the composition further comprises one or more CRISPR nucleases or sequences encoding the one or more CRISPR nucleases. In embodiments of the present invention, the composition further comprises one or more tracrRNA molecules or sequences encoding the one or more tracrRNA molecules.

Embodiments of the present invention provide a method for inactivating in a cell a mutant ELANE allele, the method comprising delivering to the cell the RNA molecules or compositions of the present invention.

In embodiments of the present invention, the one or more CRISPR nuclease or sequences encoding the one or more CRISPR nucleases and the RNA molecule or RNA molecules are delivered to the subject and/or cells substantially at the same time or at different times.

In embodiments of the present invention, the tracrRNA molecules or sequences encoding the one or more tracrRNA molecules and the RNA molecule or RNA molecules are delivered to the subject and/or cells substantially at the same time or at different times.

In embodiments of the present invention, the method comprises removing an exon containing a disease-causing mutation from a mutant allele, wherein the first RNA molecule or the first and the second RNA molecules target regions flanking an entire exon or a portion of the exon.

In embodiments of the present invention, the method comprises removing multiple exons, the entire open reading frame of a gene, or removing the entire gene.

In embodiments of the present invention, the first RNA molecule or the first and the second RNA molecules target an alternative splicing signal sequence between an exon and an intron of a mutant allele.

In embodiments of the present invention, the second RNA molecule targets a sequence present in both a mutant allele and a functional allele.

In embodiments of the present invention, the second RNA molecule targets an intron.

In embodiments of the present invention, the method results in subjecting the mutant allele to insertion or deletion by an error prone non-homologous end joining (NHEJ) mechanism, generating a frameshift in the mutant allele's sequence.

In embodiments of the present invention, the frameshift results in inactivation or knockout of the mutant allele.

In embodiments of the present invention, the frameshift creates an early stop codon in the mutant allele or the frameshift results in nonsense-mediated mRNA decay of the transcript of the mutant allele.

In embodiments of the present invention, inactivating or treating results in a truncated protein encoded by the mutant allele and a functional protein encoded by the functional allele.

Embodiments of the present invention provide use of the RNA molecules, the compositions, or the composition prepared by the method of the present invention for inactivating in a cell a mutant ELANE allele.

Embodiments of the present invention provide a medicament comprising the RNA molecules, compositions, or the compositions prepared by the methods of the instant invention for use in inactivating in a cell a mutant ELANE allele, wherein the medicament is administered by delivering to the cell the RNA molecules, compositions, or the compositions prepared by the methods of the instant invention.

Embodiments of the present invention provide for use of the methods, the modified cells, the compositions, or the compositions prepared by the methods, or the RNA molecules of the instant invention for treating ameliorating or preventing SCN or CyN in to a subject having or at risk of having SCN or CyN.

Embodiments of the present invention provide for a medicament comprising the RNA molecules, compositions, compositions prepared by the methods of the instant invention, or the modified cells of the instant invention, for use in treating ameliorating or preventing SCN or CyN, wherein the medicament is administered by delivering to a subject having or at risk of having SCN or CyN the RNA molecules, compositions, compositions prepared by the methods of the instant invention, or the modified cells of the instant invention.

Embodiments of the present invention provide for a kit for inactivating a mutant ELANE allele in a cell, comprising the RNA molecules of the instant invention, a CRISPR nuclease or sequence encoding the CRISPR nuclease, and/or a tracrRNA molecule or sequence encoding the tracrRNA molecule; and instructions for delivering the RNA molecule; CRISPR nuclease or sequence encoding the CRISPR nuclease, and/or the tracrRNA or sequence encoding the tracrRNA molecule to the cell to inactivate the mutant ELANE allele in the cell.

Embodiments of the present invention provide for a kit for treating SCN or CyN in a subject, comprising the RNA molecules of the instant invention, a CRISPR nuclease or sequence encoding the CRISPR nuclease, and/or a tracrRNA molecule or sequence encoding the tracrRNA molecule; and instructions for delivering the RNA molecule; CRISPR nuclease or sequence encoding the CRISPR nuclease, and/or the tracrRNA or sequence encoding the tracrRNA molecule to a subject having or at risk of having SCN or CyN so as to treat the SCN or CyN.

Embodiments of the present invention provide for a kit for inactivating a mutant ELANE allele in a cell, comprising the compositions, the composition prepared by the methods of the instant invention, or the modified cells of the instant invention, and instructions for delivering the composition to the cell so as to inactivate the ELANE gene in the cell.

Embodiments of the present invention provide for a kit for treating SCN or CyN in a subject, comprising the composition, the compositions prepared by the methods of the instant invention, or the modified cells of the instant invention, and instructions for delivering the compositions, the compositions prepared by the methods of the instant invention, or the modified cells of the instant invention, to a subject having or at risk of having SCN or CyN so as to treat SCN or CyN.

Definitions

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The "guide sequence portion" of an RNA molecule refers to a nucleotide sequence that is capable of hybridizing to a specific target DNA sequence, e.g., the guide sequence portion has a nucleotide sequence which is fully complementary to the DNA sequence being targeted along the length of the guide sequence portion. In some embodiments, the guide sequence portion is 17, 18, 19, 20, 21, 22, 23, 24, 25, 26, 27, 28, 29, or 30 nucleotides in length, or approximately 17-30, 17-29, 17-28, 17-27, 17-26, 17-25, 17-24, 18-22, 19-22, 18-20, 17-20, or 17-22 nucleotides in length. The entire length of the guide sequence portion is fully complementary to the DNA sequence being targeted along the length of the guide sequence portion. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence.

The term "targets" as used herein, refers to the guide sequence portion of the RNA molecule's preferential hybridization to a nucleic acid having a targeted nucleotide sequence. It is understood that the term "targets" encompasses variable hybridization efficiencies, such that there is preferential targeting of the nucleic acid having the targeted nucleotide sequence, but unintentional off-target hybridization in addition to on-target hybridization might also occur. It is understood that where an RNA molecule targets a sequence, a complex of the RNA molecule and a CRISPR nuclease molecule targets the sequence for nuclease activity.

As used herein, the term "targeting sequence" or "targeting molecule" refers a nucleotide sequence or molecule comprising a nucleotide sequence that is capable of hybridizing to a specific target sequence, e.g., the targeting sequence has a nucleotide sequence which is at least partially complementary to the sequence being targeted along the length of the targeting sequence. The targeting sequence or targeting molecule may be part of an RNA molecule that can form a complex with a CRISPR nuclease with the targeting sequence serving as the targeting portion of the CRISPR complex. When the molecule having the targeting sequence is present contemporaneously with the CRISPR molecule the RNA molecule is capable of targeting the CRISPR nuclease to the specific target sequence.

In the context targeting a DNA sequence that is present in a plurality of cells, it is understood that the targeting encompasses hybridization of the guide sequence portion of the RNA molecule with the sequence in one or more of the cells, and also encompasses hybridization of the RNA molecule with the target sequence in fewer than all of the cells in the plurality of cells. Accordingly, it is understood that where an RNA molecule targets a sequence in a plurality of cells, a complex of the RNA molecule and a CRISPR nuclease is understood to hybridize with the target sequence in one or more of the cells, and also may hybridize with the target sequence in fewer than all of the cells. Accordingly, it is understood that the complex of the RNA molecule and the CRISPR nuclease introduces a double strand break in relation to hybridization with the target sequence in one or more cells and may also introduce a double strand break in relation to hybridization with the target sequence in fewer than all of the cells. As used herein, the term "modified cells" refers to cells in which a double strand break is effected by a complex of an RNA molecule and the CRISPR nuclease as a result of hybridization with the target sequence, i.e. on-target hybridization.

The term "non-discriminatory" as used herein refers to a guide sequence portion of an RNA molecule that targets a specific DNA sequence that is common both a mutant and functional allele of a gene.

In embodiments of the present invention, RNA guide molecule may target the ELANE mutant allele based on the mutation associated with severe congenital neutropenia (SCN) or cyclic neutropenia (CyN).

In embodiments of the present invention, an RNA molecule comprises a guide sequence portion having 17-30 contiguous nucleotides containing nucleotides in the sequence set forth in any one of SEQ ID NOs: 1-31117.

It is understood that in any of the embodiments of the present invention the guide sequence portion of an RNA molecule may comprise 17-22 contiguous nucleotides set forth in any single sequence of SEQ ID NOs: 1-31117, or in any single sequence from the above groups of sequences.

The RNA molecule and or the guide sequence portion of the RNA molecule may contain modified nucleotides. Exemplary modifications to nucleotides or polynucleotides may be synthetic and encompass polynucleotides which contain nucleotides comprising bases other than the naturally occurring adenine, cytosine, thymine, uracil, or guanine bases. Modifications to polynucleotides include polynucleotides which contain synthetic, non-naturally occurring nucleosides e.g., locked nucleic acids. Modifications to polynucleotides may be utilized to increase or decrease stability of an RNA. An example of a modified polynucleotide is an mRNA containing 1-methyl pseudouridine. For examples of modified polynucleotides and their uses, see U.S. Pat. No. 8,278,036, PCT International Publication No. WO/2015/006747, and Weissman and Kariko (2015), hereby incorporated by reference.

As used herein, "contiguous nucleotides" set forth in a SEQ ID NO refers to nucleotides in a sequence of nucleotides in the order set forth in the SEQ ID NO without any intervening nucleotides.

In embodiments of the present invention, the guide sequence portion may be 20 nucleotides in length and consists of 20 nucleotides in the sequences set forth in any one of SEQ ID NOs: 1-31117. In embodiments of the present invention, the guide sequence portion may be less than 20 nucleotides in length. For example, in embodiments of the present invention the guide sequence portion may be 17, 18, or 19 nucleotides in length. In such embodiments the guide sequence portion may consist of 17, 18, or 19 nucleotides, respectively, in the sequences set forth in any one of SEQ ID NOs: 1-31117. For example, a guide sequence portion having 17 nucleotides in the sequence of 17 contiguous nucleotides set forth in SEQ ID NO: 31118 may consist of any one of the following nucleotide sequences (nucleotides excluded from the contiguous sequence are marked in strike-through):

```
                                    (SEQ ID NO: 31118)
        AAAAAAACCAGACGCCGGCC 17 nucleotide guide sequence 1:
                                    (SEQ ID NO: 31119)
        A̶A̶A̶AAAACCAGACGCCGGCC 17 nucleotide guide sequence 2:
                                    (SEQ ID NO: 31120)
        A̶A̶AAAAACCAGACGCCGGC̶C̶

17 nucleotide guide sequence 3:
                                    (SEQ ID NO: 31121)
        A̶AAAAAACCAGACGCCGG̶C̶C̶

17 nucleotide guide sequence 4:
                                    (SEQ ID NO: 31122)
        AAAAAAACCAGACGCCG̶G̶C̶C̶
```

In embodiments of the present invention, the guide sequence portion may be greater than 22 nucleotides in length. For example, in embodiments of the present invention the guide sequence portion may be 23, 24, 25, 26, 27, 28, 29, or 30 nucleotides in length. In such embodiments the guide sequence portion comprises 20, 21, or 22 nucleotides in the sequences set forth in any one of SEQ ID NOs: 1-31117 and additional nucleotides fully complimentary to a nucleotide or sequence of nucleotides adjacent to the 3' end of the target sequence, 5' end of the target sequence, or both.

In embodiments of the present invention, a CRISPR nuclease and an RNA molecule comprising a guide sequence portion form a CRISPR complex that binds to a target DNA sequence to effect cleavage of the target DNA sequence. CRISPR nucleases, e.g. Cpf1, may form a CRISPR complex comprising a CRISPR nuclease and RNA molecule without a further tracrRNA molecule. Alternatively, CRISPR nucleases, e.g. Cas9, may form a CRISPR complex between the CRISPR nuclease, an RNA molecule, and a tracrRNA molecule.

In embodiments of the present invention, the RNA molecule may further comprise the sequence of a tracrRNA molecule. Such embodiments may be designed as a synthetic fusion of the guide portion of the RNA molecule and the trans-activating crRNA (tracrRNA). (See Jinek (2012) Science). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via base pairing and may be advantageous in certain applications of the invention described herein.

The term "tracr mate sequence" refers to a sequence sufficiently complementary to a tracrRNA molecule so as to hybridize to the tracrRNA via basepairing and promote the formation of a CRISPR complex. (See U.S. Pat. No. 8,906, 616). In embodiments of the present invention, the RNA molecule may further comprise a portion having a tracr mate sequence.

According to embodiments of the present invention, an RNA molecule may be up to 300, 290, 280, 270, 260, 250, 240, 230, 220, 210, 200, 190, 180, 170, 160, 150, 140, 130, 120, 110, or 100 nucleotides in length. Each possibility represents a separate embodiment. In embodiments of the present invention, the RNA molecule may be 17 up to 300 nucleotides in length, 100 up to 300 nucleotides in length, 150 up to 300 nucleotides in length, 200 up to 300 nucleotides in length, 100 to 200 nucleotides in length, or 150 up to 250 nucleotides in length. Each possibility represents a separate embodiment.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Eukaryotic" cells include, but are not limited to, fungal cells (such as yeast), plant cells, animal cells, mammalian cells and human cells.

As used herein, the term HSPC refers to both hematopoietic stem cells and hematopoietic stem progenitor cells. Non-limiting examples of stem cells include a bone marrow cell, a myeloid progenitor cell, a multipotent progenitor cell, a lineage restricted progenitor cell.

As used herein, "progenitor cell" refers to a lineage cell that is derived from stem cell and retains mitotic capacity and multipotency (e.g., can differentiate or develop into more than one but not all types of mature lineage of cell). As used herein "hematopoiesis" or "hemopoiesis" refers to the formation and development of various types of blood cells (e.g., red blood cells, megakaryocytes, myeloid cells (e.g., monocytes, macrophages and neutrophil), and lymphocytes) and other formed elements in the body (e.g., in the bone marrow).

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity. Gene modification can be achieved using a nuclease, for example a CRISPR nuclease.

According to embodiments of the present invention, the first RNA molecule or the first and the second RNA molecules targets at least a portion of the promoter and/or the start codon and/or a portion of the UTR of the mutant allele of the ELANE gene.

According to embodiments of the present invention, there is provided a method comprising removing an exon containing a disease-causing mutation from a mutant allele, wherein the first RNA molecule or the first and the second RNA molecules target regions flanking an entire exon or a portion of the exon.

According to embodiments of the present invention, there is provided a method comprising removing multiple exons, the entire open reading frame of a gene, or removing the entire gene.

According to embodiments of the present invention, the first RNA molecule targets a mutant allele of the ELANE gene, and the second RNA molecule targets a sequence in an intron present in both the mutant and functional allele of the ELANE gene.

According to embodiments of the present invention, the second RNA molecule targets a sequence present in both a mutant allele and a functional allele of the ELANE gene.

According to embodiments of the present invention, the second RNA molecule targets an intron.

According to embodiments of the present invention, there is provided a method comprising subjecting the mutant allele to insertion or deletion by an error prone non-homologous end joining (NHEJ) mechanism, generating a frameshift in the mutant allele's sequence.

According to embodiments of the present invention, the frameshift results in inactivation or knockout of the mutant allele.

According to embodiments of the present invention, the frameshift creates an early stop codon in the mutant allele.

According to embodiments of the present invention, the frameshift results in nonsense-mediated mRNA decay of the transcript of the mutant allele.

According to embodiments of the present invention, the inactivating or treating results in a truncated protein encoded by the mutant allele and a functional protein encoded by the functional allele.

The compositions and methods of the present disclosure may be utilized for treating, preventing, ameliorating, or slowing progression of SCN or CyN.

In some embodiments, the method of deactivating a mutant allele comprises an exon skipping step comprising removing an exon containing a disease-causing mutation from the mutant allele. Removing an exon containing a disease-causing mutation in the mutant allele requires two RNA molecules which target regions flanking the entire exon or a portion of the exon. Removal of an exon containing the disease-causing mutation may be designed to eliminate the disease-causing action of the protein while allowing for expression of the remaining protein product which retains some or all of the wild-type activity. As an alternative to single exon skipping, multiple exons, the entire open reading frame or the entire gene can be excised using two RNA molecules flanking the region desired to be excised.

In some embodiments, the method of deactivating a mutant allele comprises delivering two RNA molecules to a cell, wherein one RNA molecule targets a first mutant allele of an ELANE gene and wherein the other RNA molecule targets a second mutant allele of the ELANE gene, or the second RNA molecule targets a sequence in an intron present in both the mutant or functional allele.

In some embodiments, an RNA molecule is used to target a CRISPR nuclease to an alternative splicing signal sequence between an exon and an intron of a mutant allele, thereby destroying the alternative splicing signal sequence in the mutant allele.

Any one of, or combination of, the above-mentioned strategies for deactivating a mutant allele may be used in the context of the invention.

Additional strategies may be used to deactivate a mutant allele. For example, in embodiments of the present invention, an RNA molecule is used to direct a CRISPR nuclease to an exon or a splice site of a mutant allele in order to create a double-stranded break (DSB), leading to insertion or deletion of nucleotides by an error-prone non-homologous end-joining (NHEJ) mechanism and formation of a frameshift mutation in the mutant allele. The frameshift mutation may result in: (1) inactivation or knockout of the mutant allele by generation of an early stop codon in the mutant allele, resulting in generation of a truncated protein; or (2) nonsense mediated mRNA decay of the transcript of the mutant allele. In further embodiments, one RNA molecule is used to direct a CRISPR nuclease to a promotor of a mutant allele.

In some embodiments, the method of deactivating a mutant allele further comprises enhancing activity of the functional protein such as by providing a protein/peptide, a nucleic acid encoding a protein/peptide, or a small molecule such as a chemical compound, capable of activating/enhancing activity of the functional protein.

According to some embodiments, the present disclosure provides an RNA molecule which binds to/associates with and/or directs the RNA guided DNA nuclease e.g., CRISPR nuclease to a mutant of the ELANE gene.

In some embodiments, the method comprises the steps of: contacting a mutant allele of a gene of interest with an allele-specific RNA molecule and a CRISPR nuclease e.g., a Cas9 protein, wherein the allele-specific RNA molecule and the CRISPR nuclease e.g., Cas9 associate with a nucleotide sequence of the mutant allele of the gene of interest which differs by at least one nucleotide from a nucleotide sequence of a functional allele of the gene of interest, thereby modifying or knocking-out the mutant allele.

In some embodiments, the allele-specific RNA molecule and a CRISPR nuclease is introduced to a cell encoding the gene of interest. In some embodiments, the cell encoding the gene of interest is in a mammalian subject. In some embodiments, the cell encoding the gene of interest is in a plant.

In some embodiments, the cleaved mutant allele is further subjected to insertion or deletion (indel) by an error prone non-homologous end joining (NHEJ) mechanism, generating a frameshift in the mutant allele's sequence. In some embodiments, the generated frameshift results in inactivation or knockout of the mutant allele. In some embodiments, the generated frameshift creates an early stop codon in the mutant allele and results in generation of a truncated protein. In such embodiments, the method results in the generation of a truncated protein encoded by the mutant allele and a functional protein encoded by the functional allele. In some embodiments, a frameshift generated in a mutant allele using the methods of the invention results in nonsense-mediated mRNA decay of the transcript of the mutant allele.

A skilled artisan will appreciate that in each of the embodiments of the present invention, individually, each of the RNA molecules of the present invention are capable of complexing with a nuclease, e.g. a CRISPR nuclease, such as to associate with a target genomic DNA sequence of interest next to a protospacer adjacent motif (PAM). The nuclease then mediates cleavage of target DNA to create a double-stranded break within the protospacer. Accordingly, in embodiments of the present invention, the guide sequences and RNA molecules of the present invention may target a location 1, 2, 3, 4, 5, 6, 7, 8, 9, 10, 11, 12, 13, 14, 15, 16, 17, 18, 19, 20, 21, 22, 23, 24, 25, 26, 27, or 28 nucleotides upstream or downstream from a PAM site.

Therefore, in embodiments of the present invention, an RNA molecule of the present invention in complex with a nuclease, e.g., a CRISPR nuclease, may affect a double strand break in an allele of a gene 1, 2, 3, 4, 5, 6, 7, 8, 9, 10, 11, 12, 13, 14, 15, 16, 17, 18, 19, 20, 21, 22, 23, 24, 25, 26, 27, 28 upstream or downstream from a target site.

Where the target site (e.g. a pathogenic mutation) is within the PAM site, it is understood that the RNA molecule may be designed to target a sequence 1, 2, 3, 4, 5, 6, 7, 8, 9, 10, 11, 12, 13, 14, 15, 16, 17, 18, 19, 20, 21, 22, 23, 24, 25, 26, 27, or 28 nucleotides upstream or downstream from the PAM site. Accordingly, an RNA molecule is designed to target a nuclease, e.g. a CRISPR nuclease, only to an allele containing the pathogenic mutation.

In embodiments of the present invention, an RNA molecule is designed to target a mutant allele in the ELANE gene, wherein the RNA molecule and/or the complex of the RNA molecule and a CRISPR nuclease targets the nucleotide base present in the mutant allele of the ELANE gene In embodiments of the present invention, the RNA molecules, compositions, methods, cells, kits, or medicaments are utilized for treating a subject having a disease phenotype resulting from the heterozygote ELANE gene. In embodiments of the present invention, the disease is SCN or CyN. In such embodiments, the method results in improvement, amelioration or prevention of the disease phenotype.

In embodiments of the present invention, the RNA molecules, compositions, methods, cells, kits, or medicaments of the present invention are utilized in combination with a second therapy for SCN or CyN to treat the subject. In embodiments of the present invention, the RNA molecules, compositions, methods, kits, or medicaments of the present invention are administered prior to administration of the second therapy, during administration of the second therapy, and/or after administration of the second therapy.

In embodiments of the present invention, the RNA molecules, compositions, methods, cells, kits, or medicaments of the present invention are administered in combination with Granulocyte colony-stimulating factor (G-CSF) therapy.

Embodiments referred to above refer to a CRISPR nuclease, RNA molecule(s), and tracrRNA being effective in a subject or cells at the same time. The CRISPR, RNA molecule(s), and tracrRNA can be delivered substantially at the same time or can be delivered at different times but have effect at the same time. For example, this includes delivering the CRISPR nuclease to the subject or cells before the RNA molecule and/or tracr RNA is substantially extant in the subject or cells.

According to embodiments of the present invention, there is provided a method for inactivating in a cell a mutant allele of the ELANE gene, the method comprising the steps of:
  a) selecting a cell with an ELANE gene mutation associated with SCN or CyN wherein the ELANE gene mutation is selected from the group consisting of the ELANE mutants set forth in Table 1;
  b) introducing to the cell a composition comprising:
    a CRISPR nuclease or sequence encoding the CRISPR nuclease, and
    a first RNA molecule comprising a guide sequence portion having 17-30 nucleotides,
  wherein a complex of the CRISPR nuclease and the first RNA molecule affects a double strand break in the mutant allele of the ELANE gene and not in the functional allele of the ELANE gene in the cell;
  thereby inactivating the mutant allele of the ELANE gene in the cell.

According to embodiments of the present invention, there is provided a method for inactivating in a cell a mutant allele of the ELANE gene, the method comprising the steps of:
  a) selecting a cell with an ELANE gene mutation associated with SCN or CyN wherein the ELANE gene mutation is selected from the group consisting of the ELANE mutants set forth in Table 1;
  b) introducing to the cell a composition comprising:
    a CRISPR nuclease or sequence encoding the CRISPR nuclease, and
    a first RNA molecule comprising a guide sequence portion having 17-30 nucleotides,
  wherein a complex of the CRISPR nuclease and the first RNA molecule affects a double strand break in the mutant allele of the ELANE gene and not in the functional allele of the ELANE gene in the cell;
  and wherein the method further comprises introduction of a second RNA molecule comprising a guide sequence portion capable of complexing with a CRISPR nuclease, wherein the complex of the second RNA molecule and the CRISPR nuclease affects a second double strand break in the ELANE gene;
thereby inactivating the mutant allele of the ELANE gene in the cell.

According to embodiments of the present invention, there is provided a method for inactivating in a cell a mutant allele of the ELANE gene having a mutation associated with SCN or CyN wherein the mutant allele is selected from the group consisting of the ELANE mutants set forth in Table 1, the method comprising
  introducing to the cell a composition comprising:
    a CRISPR nuclease or sequence encoding the CRISPR nuclease, and
    a first RNA molecule comprising a guide sequence portion having 17-30 nucleotides,
  wherein a complex of the CRISPR nuclease and the first RNA molecule affects a double strand break in the mutant allele of the ELANE gene;
  thereby inactivating the mutant allele of the ELANE gene in the cell.

According to embodiments of the present invention, there is provided a method for inactivating in a cell a mutant allele of the ELANE gene associated with SCN or CyN wherein the mutant allele is selected from the group consisting of the ELANE mutants set forth in Table 1, the method comprising:
  introducing to the cell a composition comprising:
    a CRISPR nuclease or sequence encoding the CRISPR nuclease, and
    a first RNA molecule comprising a guide sequence portion having 17-30 nucleotides,
  wherein a complex of the CRISPR nuclease and the first RNA molecule affects a double strand break in the mutant allele of the ELANE gene;
  and wherein the method further comprises introduction of a second RNA molecule comprising a guide sequence portion capable of complexing with a CRISPR nuclease, wherein the complex of the second RNA molecule and CRISPR nuclease affects a second double strand break in the ELANE gene;
  thereby inactivating the mutant allele of the ELANE gene in the cell.

In embodiments of the present invention, a complex of the CRISPR nuclease and the first RNA molecule affects a double strand break in the mutant allele of the ELANE gene and not in the functional allele of the ELANE gene in the cell.

In embodiments of the present invention, the cell comprises a second mutant allele selected from the group consisting of the ELANE mutants set forth in Table 1.

In embodiments of the present invention, a cell with an ELANE gene mutation associated with SCN or CyN may be from a subject with the ELANE gene mutation and/or afflicted with SCN or CyN. Accordingly, selecting a cell with an ELANE gene mutation may comprise selecting a subject with the ELANE gene mutation. In further embodiments of the present invention, selecting a cell may comprise selecting a cell from a subject with the ELANE gene mutation. In embodiments of the present invention, introducing the compositions of the subject invention to the cell may comprise introducing the compositions of the invention to the cell of a subject afflicted with the ELANE gene mutation.

Accordingly, in embodiments of the present invention, there is provided a method for inactivating in a cell a mutant allele of the ELANE gene of a subject, the method comprising the step of selecting a subject with an ELANE gene mutation resulting in SCN or CyN wherein the ELANE gene mutation is selected from the group consisting of the ELANE mutants set forth in Table 1.

Accordingly, embodiments of the present invention encompass the screening of subjects or cells for the ELANE gene. A person having ordinary skill in the art would readily understand methods of screening for mutations within the ELANE gene in the art, by way of non-limiting examples, e.g., sequencing-by-synthesis, Sanger sequencing, karyotyping, Fluorescence In situ Hybridization, and/or microarray testing. In embodiments of the present invention, mutations within the ELANE gene are screened by exon sequencing.

In embodiments of the present invention, the subject is or has been diagnosed with SCN or CyN by measuring the absolute neutrophil count (ANC) in peripheral blood. In embodiments of the present invention, SCN is or was diagnosed before the subject reaches the age 6 months. In embodiments of the present invention, CyN is or was diagnosed between the ages of 12 and 24 months, or after the age of 24 months. In embodiments of the present invention, SCN or Cyn is diagnosed by one or more of recurrent acute stomatologic disorders. In embodiments of the present invention, SCN or CyN is diagnosed by bone marrow examination, preferably the bone marrow examination is a cytogenetic bone marrow study. In embodiments of the present invention, SCN or CyN is diagnosed by one or more of: antineutrophil antibody assay, immunoglobulin assay (Ig GAM), lymphocyte immunophenotyping, pancreatic markers (serum trypsinogen and fecal elastase) and liposoluble vitamin levels (vitamins A, E and D). It is understood that any diagnostic method may be used with any other diagnostic method.

In embodiments of the present invention, a subject diagnosed with SCN or CyN is screened by Exon sequencing to identify an ELANE pathogenic mutation in the ELANE gene. In further embodiments the subject is screened by Sanger sequencing to confirm heterozygocity of at least one of the ELANE gene mutations selected from the group consisting of the ELANE mutants set forth in Table 1. In embodiments of the present invention, the nucleotide of the mutant allele of the ELANE gene is determined using BAC bio. In embodiments of the present invention, appropriate guides are selected according to Tables 2A-2C. In embodiments of the present invention, the guides selected are introduced to cells, e.g. PBMCs, obtained from the subject and reduction in the pathogenic ELANE mutation in the cells is measured by, e.g. Next Generation Sequencing.

It is understood that the CRISPR/Cas9 gene editing system enables targeting the nuclease to a target site in a sequence specific manner to address disease-causing mutations. Hematopoietic stem and progenitor cells (HSPCs) have therapeutic potential because of their ability to both self-renew and differentiate (Yu, Natanson, and Dunbar 2016). Accordingly, embodiments of the present invention apply genome editing to HSPCs.

In embodiments of the present invention, an autologous therapy and utilizes autologous CD34+ hematopoietic stem cells from patients diagnosed with SCN or CyN which are edited with CRISPR/Cas9. In embodiments of the present invention, CD34+ cells are isolated from bone marrow or peripheral blood mononucleated cells (PBMCs) following patient apheresis.

In the case of dominant negative (or compound heterozygous) indications, such as SCN or CyN, the strategy is to edit the mutant allele and avoid cleavage in the non-mutant allele or other off targets by targeting the mutant allele sequence.

Embodiments of the present invention may include the following steps:

- selection of a patient diagnosed with SCN or CyN identified as having a mutant allele of the ELANE gene selected from the group consisting of the ELANE mutants set forth in Table 1;
- selection of a therapeutic strategy based on the identified mutant allele of the candidate patient;
- obtaining HSPC cells from the bone marrow of the subject either by aspiration or by mobilization and apheresis of peripheral blood, optionally, the HSPC cells are processed (e.g., enriched, stimulated, both);
- introducing into the HSPC cells (e.g., by ex vivo electroporation) a composition comprising:
  - a CRISPR nuclease or a sequence encoding the same (e.g., mRNA),
  - a discriminatory RNA molecule that targets the mutant allele, and
  - a non-discriminatory RNA molecule targeting a sequence in intron 3, intron 4 or 3' UTR, which is common to both the mutant allele and the other allele,
  - thereby editing the HSPC cells to knockout expression of mutant ELANE allele; and
- introducing the edited HSPC to the candidate patient.

In embodiments of the present invention, CD34+ cells may be isolated from bone marrow or peripheral blood mononucleated cells (PBMCs) following patient apheresis. Bone marrow or PBMCs may be collected from the patient by apheresis following HSPC mobilization. In embodiments of the invention the apheresis product may be washed to remove platelets and a CD34+ cell population may be enriched via purification using, e.g. a CliniMACS system (Miltenyi Biotec). In embodiments of the present invention, the selected cells may be prestimulated ex vivo, e.g. with a mixture of recombinant human cytokines. In embodiments of the present invention, the cells may undergo electroporation. In embodiments of the present invention, prior to electroporation, stimulated cells (e.g. CD34+ cells), the CRISPR nuclease mRNA and gRNA may be preincubated under defined conditions. In embodiments of the present invention, the cells are electroporated ex vivo with the CRISPR nuclease mRNA/gRNA mixture or with a preassembled RNPs (Ribonuclease protein of the CRISPR nuclease protein and gRNA), followed by cell washing. In embodiments of the present invention, the cells are suspended into a final formulation. In embodiments of the present invention, the cells may be resuspended. In embodiments of the present invention, the resuspended cells may be filled into bags for infusion. In embodiments of the present invention, the bags may be frozen using a freeze down step in a controlled rate freezer and/or stored in the vapor phase of liquid nitrogen. In embodiments of the present invention, the product may be administered by intravenous (IV) administration to a patient.

Dominant Genetic Disorders

One of skill in the art will appreciate that all subjects with any type of heterozygote genetic disorder (e.g., dominant genetic disorder) may be subjected to the methods described herein. In one embodiment, the present invention may be used to target a gene involved in, associated with, or causative of dominant genetic disorders such as, for example, SCN or CyN. In some embodiments, the dominant genetic disorder is SCN or CyN. In some embodiments, the target gene is the ELANE gene.

CRISPR Nucleases and PAM Recognition

In some embodiments, the sequence specific nuclease is selected from CRISPR nucleases, or a functional variant thereof. In some embodiments, the sequence specific nuclease is an RNA guided DNA nuclease. In such embodiments, the RNA sequence which guides the RNA guided DNA nuclease (e.g., Cpf1) binds to and/or directs the RNA guided DNA nuclease to the sequence comprising at least one nucleotide which differs between a mutant allele and its counterpart functional allele (e.g., to a pathogenic mutation). In some embodiments, the CRISPR complex does not further comprise a tracrRNA. In a non-limiting example, in which the RNA guided DNA nuclease is a CRISPR protein, the at least one nucleotide which differs between the dominant mutant allele and the functional allele may be within the PAM site and/or proximal to the PAM site within the region that the RNA molecule is designed to hybridize to. A skilled artisan will appreciate that RNA molecules can be engineered to bind to a target of choice in a genome by commonly known methods in the art.

In embodiments of the present invention, a type II CRISPR system utilizes a mature crRNA:tracrRNA complex directs a CRISPR nuclease, e.g. Cas9, to the target DNA via Watson-Crick base-pairing between the crRNA and the protospacer on the target DNA next to the protospacer adjacent motif (PAM), an additional requirement for target recognition. The CRISPR nuclease then mediates cleavage of target DNA to create a double-stranded break within the protospacer. A skilled artisan will appreciate that each of the engineered RNA molecule of the present invention is further designed such as to associate with a target genomic DNA sequence of interest next to a protospacer adjacent motif (PAM), e.g., a PAM matching the sequence relevant for the type of CRISPR nuclease utilized, such as for a non-limiting example, NGG or NAG, wherein "N" is any nucleobase, for *Streptococcus pyogenes* Cas9 WT (Sp-CAS9); NNGRRT for *Staphylococcus aureus* (SaCas9); NNNVRYM for *Jejuni* Cas9 WT; NGAN or NGNG for SpCas9-VQR variant; NGCG for SpCas9-VRER variant; NGAG for SpCas9-EQR variant; NNNNGATT for *Neisseria meningitidis* (NmCas9); or TTTV for Cpf1. RNA molecules of the present invention are each designed to form complexes in conjunction with one or more different CRISPR nucleases and designed to target polynucleotide sequences of interest utilizing one or more different PAM sequences respective to the CRISPR nuclease utilized.

In some embodiments, an RNA-guided DNA nuclease e.g., a CRISPR nuclease, may be used to cause a DNA break at a desired location in the genome of a cell. The most commonly used RNA-guided DNA nucleases are derived from CRISPR systems, however, other RNA-guided DNA nucleases are also contemplated for use in the genome editing compositions and methods described herein. For instance, see U.S. Patent Publication No. 2015-0211023, incorporated herein by reference.

CRISPR systems that may be used in the practice of the invention vary greatly. CRISPR systems can be a type I, a type II, type III, or type V system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas12a, Cas12b, Cas12c, Cas12d, Cas12d, Cas1 Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966. (See, e.g., Koonin 2017).

In some embodiments, the RNA-guided DNA nuclease is a CRISPR nuclease derived from a type II CRISPR system (e.g., Cas9). The CRISPR nuclease may be derived from *Streptococcus pyogenes, Streptococcus thermophilus, Streptococcus* sp., *Staphylococcus aureus, Neisseria meningitidis, Treponema denticola, Nocardiopsis dassonvillei, Streptomyces pristinaespiralis, Streptomyces viridochromogenes, Streptomyces viridochromogenes, Streptosporangiurn roseurn, Streptosporangiurn roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobiurn arabaticum, Ammonifex degensii, Caldicelulosiruptor becscii, Candidatus Desulforudis, Clostridium botulinum, Clostridium Finegoldia magna, Natranaerobius thermophilus, Pelotomaculum thermopropionicum, Acidithiobacillus caldus, Acidithiobacillus ferrooxidans, Allochromatiurn vinosurn, Marinobacter* sp., *Nitrosococcus halophilus, Nitrosococcus watsoni, Pseudoalteromonas haloplanktis, Ktedonobacter racemifer, Methanohalobiurn evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Francisella* cf *novicida* Fx1, *Alicyclobacillus acidoterrestris, Oleiphilus* sp., *Bacterium* CG09_39_24, *Deltaproteobacteria bacterium*, or any species which encodes a CRISPR nuclease with a known PAM sequence. CRISPR nucleases encoded by uncultured bacteria may also be used in the context of the invention. (See Burstein et al. Nature, 2017). Variants of CRIPSR proteins having known PAM sequences e.g., SpCas9 D1135E variant, SpCas9 VQR variant, SpCas9 EQR variant, or SpCas9 VRER variant may also be used in the context of the invention.

In embodiments of the present invention, the CRISPR nuclease has cleavage activity when used with an RNA molecule comprising a guide sequence portion having 21-23, or 21-22 nucleotides and may be derived from any of the species recited above. A specific example of a CRISPR nuclease which has cleavage activity when used with an RNA molecule comprising a guide sequence portion having 21 nucleotides is described in Mojica, F. J., et al. (1993). A specific example of a CRISPR nuclease which has cleavage activity when used with an RNA molecule comprising a guide sequence portion having 22 nucleotides is described in Kim, E. et al. (2017). Mojica, F. J., et al. (1993) and Kim, E. et al. (2017) in their entirety and/or for the specific description CRISPR nucleases, are incorporated herein by reference. In such embodiments, the CRISPR nuclease may be engineered and/or non-naturally occurring.

In embodiments of the present invention, the CRISPR nuclease has greater cleavage activity when used with an RNA molecule comprising a guide sequence portion having 21-23 nucleotides, compared to its cleavage activity when used with an RNA molecule comprising a guide sequence portion having 20 or fewer nucleotides, and/or 24 or more nucleotides. In embodiments of the present invention, the CRISPR nuclease has greater cleavage activity when used with an RNA molecule comprising a guide sequence portion having 21-22 nucleotides, compared to its cleavage activity when used with an RNA molecule comprising a guide sequence portion having 20 or fewer nucleotides, and/or 23 or more nucleotides. In an embodiment, the CRISPR nuclease has its greatest cleavage activity when used with an RNA molecule comprising a guide sequence portion having 22 nucleotides.

Thus, an RNA guided DNA nuclease of a CRISPR system, such as a Cas9 protein or modified Cas9 or homolog or ortholog of Cas9, or other RNA guided DNA nucleases belonging to other types of CRISPR systems, such as Cpf1 and its homologs and orthologs, may be used in the compositions of the present invention.

In certain embodiments, the CRIPSR nuclease may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein.

In some embodiments, the CRISPR nuclease is Cpf1. Cpf1 is a single RNA-guided endonuclease which utilizes a T-rich protospacer-adjacent motif. Cpf1 cleaves DNA via a staggered DNA double-stranded break. Two Cpf1 enzymes from *Acidaminococcus* and Lachnospiraceae have been shown to carry out efficient genome-editing activity in human cells. (See Zetsche et al. (2015) Cell).

Thus, an RNA guided DNA nuclease of a Type II CRISPR System, such as a Cas9 protein or modified Cas9 or homologs, orthologues, or variants of Cas9, or other RNA guided DNA nucleases belonging to other types of CRISPR systems, such as Cpf1 and its homologs, orthologues, or variants, may be used in the present invention.

In some embodiments, the guide molecule comprises one or more chemical modifications which imparts a new or improved property (e.g., improved stability from degradation, improved hybridization energetics, or improved binding properties with an RNA guided DNA nuclease). Suitable chemical modifications include, but are not limited to one or more of: modified bases, modified sugar moieties, or modified inter-nucleoside linkages. Non-limiting examples of suitable chemical modifications include: 4-acetylcytidine, 5-(carboxyhydroxymethyl)uridine. 2'-O-methylcytidine. 5-carboxymethylaminomethyl-2-thiouridine. 5-carboxymethylaminomethyluridine, dihydrouridine, 2'-O-methylpseudouridine, "beta, D-galactosylqueuosine", 2'-O-methylguanosine, inosine, N6-isopentenyladenosine, 1-methyladenosine, 1-methylpseudouridine, 1-methylguanosine. 1-methylinosine, "2,2-dimethvlguanosine", 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, "beta. D-mannosylqueuosine", 5-methoxycarbonylmethyl-2-thiouridine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl)N-methylcarbamoyl)threonine, uridine-5-oxyacetic acid-methylester, uridine-5-oxyacetic acid, wybutoxosine, queuosine, 2-thiocytidine, 5-methyl-2-thiouridine, 2-thiouridine, 4-thiouridine. 5-methyluridine, N-((9-beta-D-ribofuranosylpurine-6-yl)-carbamoyl)threonine, 2'-O-methyl-5-methyluridine, 2'-O-methyluridine, wybutosine, "3-(3-amino-3-carboxy-propyl)uridine, (acp3)u", 2'-O-methyl (M), 3'-phosphorothioate (MS), 3'-thioPACE (MSP), pseudouridine, or 1-methyl pseudo-uridine. Each possibility represents a separate embodiment of the present invention.

Further non-limiting examples of suitable chemical modifications include: $m^1A$ (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2i6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl) adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2$ 2 G ($N^2,N^2$-dimethylguanosine); $m^2Gm$ ($N^{2,}$ 2'-O-dimethylguanosine); $m^2$ $_2$ Gm ($N^2,N^2$, 2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); preQo (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5S^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmmm^5s^2U$ (5-carboxymethylaminomethyl-2-thiouridine); dimethyladenosine); Im (2'-O-methylinosine); $m^4C$ ($N^4$-methylcytidine); $m^4Cm$ ($N^4$, 2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6$ 2 Am ($N^6,N^6,$O-2'-trimethyladenosine); $m^{2,7}G$ ($N^2$,7-dimethylguanosine); m2,2,7G ($N^2,N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); or $ac^6A$ ($N^6$-acetyladenosine). Each possibility represents a separate embodiment of the present invention. (See e.g. U.S. Pat. No. 9,750,824).

In embodiments of the present invention, the CRISPR nuclease has greater cleavage activity when used with an RNA molecule comprising a guide sequence portion having 21-23 nucleotides, compared to its cleavage activity when used with an RNA molecule comprising a guide sequence portion having 20 or fewer nucleotides, and/or 24 or more nucleotides. In embodiments of the present invention, the CRISPR nuclease has greater cleavage activity when used with an RNA molecule comprising a guide sequence portion having 21-22 nucleotides, compared to its cleavage activity when used with an RNA molecule comprising a guide sequence portion having 20 or fewer nucleotides, and/or 23 or more nucleotides. In an embodiment, the CRISPR nuclease has its greatest cleavage activity when used with an RNA molecule comprising a guide sequence portion having 22 nucleotides.

In an embodiment, such a CRISPR nuclease has at least 95% identity to the amino acid sequence as set forth in SEQ ID NO: 31125 or the sequence encoding the CRISPR nuclease has at least a 95% sequence identity to SEQ ID NO: 31131 or SEQ ID NO: 31132. In an embodiment, such a CRISPR nuclease has at least 100%, 99%, 98%, 97%, 96%, 95%, 94%, 93%, 92%, 91%, 90%, 89%, 88%, 87%, 86%, 85%, 84%, 83%, or 82% identity to the amino acid sequence as set forth in SEQ ID NO: 31125 or the sequence encoding the CRISPR nuclease has at least a 100%, 99%, 98%, 97%, 96%, 95%, 94%, 93%, 92%, 91%, 90%, 89%, 88%, 87%, 86%, 85%, 84%, 83%, or 82% sequence identity to SEQ ID NO: 31131 or SEQ ID NO: 31132.

Guide Sequences which Specifically Target a Mutant Allele

A given gene may contain thousands of sequence variations, including variations comprising a pathogenic mutation within a mutant allele. Utilizing a 24 base pair target window for specifically targeting each known pathogenic mutation in a mutant allele would require hundreds of thousands of guide sequences. Furthermore, any given guide sequence when utilized to target a specific sequence (e.g., a target sequence containing a pathogenic mutation) may result in degradation of the guide molecule, limited or no activity, or off-target effects. Accordingly, suitable guide sequences are necessary for targeting a given mutant allele. By the present invention, a novel set of guide sequences have been identified for knocking out expression of a mutated protein, inactivating a mutant ELANE gene allele, and treating SCN or CyN.

The present disclosure provides guide sequences capable of specifically targeting a mutant allele for inactivation while leaving the functional allele unmodified. The guide sequences of the present invention are designed to, and are most likely to, specifically differentiate between a mutant allele and a functional allele. Of all possible guide sequences which target a mutant allele desired to be inactivated, the specific guide sequences disclosed herein are specifically effective to function with the disclosed embodiments.

For each gene, any one of the following strategies may be used to deactivate the mutant allele: (1) Knockout strategy using one RNA molecule—one RNA molecule is utilized to direct a CRISPR nuclease to a mutant allele and create a double-strand break (DSB) leading to formation of a frameshift mutation in an exon or in a splice site region of the mutant allele; (2) Knockout strategy using two RNA molecules—two RNA molecules are utilized. A first RNA molecule targets a region in the promoter or an upstream region of a mutant allele and another RNA molecule targets downstream of the first RNA molecule in a promoter, exon, or intron of the mutant allele; (3) Exon(s) skipping strategy—one RNA molecule may be used to target a CRISPR nuclease to a splice site region, either at the 5'end of an intron (donor sequence) or the 3' end of an intron (acceptor sequence), in order to destroy the splice site. Alternatively, two RNA molecules may be utilized such that a first RNA molecule targets an upstream region of an exon and a second RNA molecule targets a region downstream of the first RNA molecule, thereby excising the exon(s). Based on the locations of each mutant allele, any one of, or a combination of, the above-mentioned methods to deactivate the mutant allele may be utilized.

The at least one nucleotide which differs between the mutant allele and the functional allele, may be upstream, downstream or within the sequence of the disease-causing mutation of the gene of interest. The at least one nucleotide which differs between the mutant allele and the functional allele, may be within an exon or within an intron of the gene of interest. In some embodiments, the at least one nucleotide which differs between the mutant allele and the functional allele is within an exon of the gene of interest. In some embodiments, the at least one nucleotide which differs between the mutant allele and the functional allele is within an intron or an exon of the gene of interest, in close proximity to a splice site between the intron and the exon e.g., 1, 2, 3, 4, 5, 6, 7, 8, 9, 10, 11, 12, 13, 14, 15, 16, 17, 18, 19, or 20 nucleotides upstream or downstream to the splice site.

Guide sequences of the present invention may satisfy any one of the above criteria and are most likely to differentiate between a mutant allele from its corresponding functional allele.

In some embodiments the RNA molecule targets a mutant allele in the ELANE gene as shown in column 1 of Table 1 below.

Embodiments of the present invention may include excising the promoter region until intron 3 or intron 4 or the 3' UTR.

Embodiments of the present invention may include excising from intron 3 or intron 4 or 3' UTR to regions downstream to the 3' UTR.

Embodiments of the present invention excising from intron 3 or intron 4 or 3' UTR to regions downstream to the 3' UTR. The strategy is designed such as to specifically knock-out the disease-causing allele ('mutant allele'), while leaving the healthy allele intact.

Delivery to Cells

It is understood that in the methods embodied, the RNA molecules and compositions described herein may be delivered to a target cell or subject by any suitable means. The following embodiments provide non-limiting examples of methods of delivery of the RNA molecules and composition of the present invention.

In some embodiments, RNA molecule compositions of the present invention may be targeted to any cell which contains and/or expresses a dominant negative allele, including any mammalian or plant cell. For example, in one embodiment the RNA molecule specifically targets a mutant ELANE allele and the target cell is a hepatocyte cell.

Any suitable viral vector system may be used to deliver nucleic acid compositions e.g., the RNA molecule compositions of the subject invention. Conventional viral and non-viral based gene transfer methods can be used to introduce nucleic acids and target tissues. In certain embodiments, nucleic acids are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson (1992) Science 256:808-813; Nabel & Feigner (1993) TIBTECH 11:211-217; Mitani & Caskey (1993) TIBTECH 11:162-166; Dillon (1993) TIBTECH 11:167-175; Miller (1992) Nature 357:455-460; Van Brunt (1988) Biotechnology 6(10):1149-1154; Vigne (1995) Restorative Neurology and Neuroscience 8:35-36; Kremer & Perricaudet (1995) British Medical Bulletin 51(1):31-44; Haddada et al. (1995) in Current Topics in Microbiology and Immunology Doerfler and Bohm (eds.); and Yu et al. (1994) Gene Therapy 1:13-26.

Methods of non-viral delivery of nucleic acids and/or proteins include electroporation, lipofection, microinjection, biolistics, particle gun acceleration, virosomes, liposomes, immunoliposomes, lipid nanoparticles (LNPs), polycation or lipid:nucleic acid conjugates, artificial virions, and agent-enhanced uptake of nucleic acids or can be delivered to plant cells by bacteria or viruses (e.g., *Agrobacterium, Rhizobium* sp. NGR234, *Sinorhizoboium meliloti, Mesorhizobium loti*, tobacco mosaic virus, potato virus X, cauliflower mosaic virus and cassava vein mosaic virus). (See, e.g., Chung et al. (2006) Trends Plant Sci. 11(1):1-4). Sonoporation using, e.g., the Sonitron 2000 system (Rich-Mar), can also be used for delivery of nucleic acids. Cationic-lipid mediated delivery of proteins and/or nucleic acids is also contemplated as an in vivo or in vitro delivery method. (See Zuris et al. (2015) Nat. Biotechnol. 33(1):73-80; see also Coelho et al. (2013) N. Engl. J. Med. 369, 819-829; Judge et al. (2006) Mol. Ther. 13, 494-505; and Basha et al. (2011) Mol. Ther. 19, 2186-2200).

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see, e.g., U.S. Pat. No. 6,008,336). Lipofection is described in e.g., U.S. Pat. Nos. 5,049,386, 4,946,787; and 4,897,355, and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (See, e.g., Crystal (1995) Science 270:404-410; Blaese et al. (1995) Cancer Gene Ther. 2:291-297; Behr et al. (1994) Bioconjugate Chem. 5:382-389; Remy et al. (1994) Bioconjugate Chem. 5:647-654; Gao et al. (1995) Gene Therapy 2:710-722; Ahmad et al. (1992) Cancer Res. 52:4817-4820; U.S. Pat. Nos. 4,186, 183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (See MacDiarmid et al (2009) Nature Biotechnology 27(7):643).

The use of RNA or DNA viral based systems for viral mediated delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (See, e.g., Buchschacher et al. (1992) J. Virol. 66:2731-2739; Johann et al. (1992) J. Virol. 66:1635-1640; Sommerfelt et al. (1990) Virol. 176:58-59; Wilson et al. (1989) J. Virol. 63:2374-2378; Miller et al. (1991) J. Virol. 65:2220-2224; PCT/US94/05700).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) Blood 85:3048-305; Kohn et al. (1995) Nat. Med. 1:1017-102; Malech et al. (1997) PNAS 94:22 12133-12138). PA317/pLASN was the first therapeutic vector used in a gene therapy trial. (Blaese et al. (1995). Transduction efficiencies of 50% or greater have been observed for MFG-S packaged vectors. (Ellem et al. (1997) Immunol Immunother. 44(1):10-20; Dranoff et al. (1997) Hum. Gene Ther. 1:111-2).

Packaging cells are used to form virus particles that are capable of infecting a host cell. Such cells include 293 cells, which package adenovirus, AAV, and Psi-2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) Proc. Natl. Acad. Sci. USA 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravitreal, intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid composition, and re-infused back into the subject organism (e.g., patient). Various cell types suitable for ex vivo transfection are well known to those of skill in the art (See, e.g., Freshney et al. (1994) Culture of Animal Cells, A Manual of Basic Technique, 3rd ed, and the references cited therein for a discussion of how to isolate and culture cells from patients).

Suitable cells include, but are not limited to, eukaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), perC6 cells, any plant cell (differentiated or undifferentiated), as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with a guided nuclease system (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma, and TNF-alpha are known (as a non-limiting example see, Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Iad (differentiated antigen presenting cells) (as a non-limiting example see Inaba et al. (1992) J. Exp. Med. 176:1693-1702). Stem cells that have been modified may also be used in some embodiments.

Typically, the cells are administered in a pharmaceutical composition comprising at least one pharmaceutically-acceptable carrier. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically-acceptable material, composition or vehicle, such as a liquid or solid filler, diluent, excipient, or solvent encapsulating material.

Any one of the RNA molecule compositions described herein is suitable for genome editing in post-mitotic cells or any cell which is not actively dividing, e.g., arrested cells. Examples of post-mitotic cells which may be edited using an RNA molecule composition of the present invention include, but are not limited to, a hepatocyte cell.

Vectors (e.g., retroviruses, liposomes, etc.) containing therapeutic nucleic acid compositions can also be administered directly to an organism for transduction of cells in vivo. Administration is by any of the routes normally used for introducing a molecule into ultimate contact with blood or tissue cells including, but not limited to, injection, infusion, topical application (e.g., eye drops and cream) and electroporation. Suitable methods of administering such nucleic acids are available and well known to those of skill in the art, and, although more than one route can be used to administer a particular composition, a particular route can often provide a more immediate and more effective reaction than another route. According to some embodiments, the composition is delivered via IV injection.

Vectors suitable for introduction of transgenes into immune cells (e.g., T-cells) include non-integrating lentivirus vectors. See, e.g., U.S. Patent Publication No. 2009-0117617.

Pharmaceutically acceptable carriers are determined in part by the particular composition being administered, as well as by the particular method used to administer the composition. Accordingly, there is a wide variety of suitable formulations of pharmaceutical compositions available, as described below (See, e.g., Remington's Pharmaceutical Sciences, 17th ed., 1989).

In accordance with some embodiments, there is provided an RNA molecule which binds to/associates with and/or directs the RNA guided DNA nuclease to a sequence comprising at least one nucleotide which differs between a mutant allele and a functional allele (e.g., a pathogenic mutation) of a gene of interest. For example, a disease-causing or pathogenic sequence of the mutant allele may be specifically targeted since this sequence is not present in the functional allele.

The disclosed compositions and methods may also be used in the manufacture of a medicament for treating dominant genetic disorders in a patient.

Mechanisms of Action for Several Embodiments Disclosed Herein

Mutations in ELANE that were demonstrated to lead to SCN or CyN, mediate translation from alternative in frame ORF (open reading frame) that generate truncated N-terminus protein thus causing ER and protein misfolding stress.

Without being bound by any theory or mechanism, the instant invention may be utilized to apply a CRISPR nuclease to process the mutated pathologic ELANE allele and not the functional ELANE allele, such as to prevent expression of the mutated pathologic allele or to produce a truncated non-pathologic peptide from the mutated pathologic allele, or to repair/correct the mutated pathologic ELANE allele in order to prevent ameliorate or treat SCN or CyN.

Several alternative editing strategies include exclusion of the whole gene, truncation of the gene to exclude the C-terminus of the gene, and attenuation of the expression of the gene.

Examples of RNA Guide Sequences which Specifically Target Mutant Alleles of ELANE Gene.

Although a large number of guide sequences can be designed to target a mutant allele, the nucleotide sequences described in Table 1 identified by SEQ ID NOs: 1-31117 below were specifically selected to effectively implement the methods set forth herein and to effectively discriminate between alleles.

Table 1 shows guide sequences designed for use as described in the embodiments above to associate with mutant ELANE alleles. Each engineered guide molecule is further designed such as to associate with a target genomic DNA sequence of interest that lies next to a protospacer adjacent motif (PAM), e.g., a PAM matching the sequence NGG or NAG, where "N" is any nucleobase. The guide sequences were designed to work in conjunction with one or more different CRISPR nucleases, including, but not limited to, e.g. SpCas9WT (PAM SEQ: NGG), SpCas9.VQR.1 (PAM SEQ: NGAN), SpCas9.VQR.2 (PAM SEQ: NGNG), SpCas9.EQR (PAM SEQ: NGAG), SpCas9.VRER (PAM SEQ: NGCG), SaCas9WT (PAM SEQ: NNGRRT), NmCas9WT (PAM SEQ: NNNNGATT), Cpf1 (PAM SEQ: TTTV), or JeCas9WT (PAM SEQ: NNNVRYM). RNA molecules of the present invention are each designed to form complexes in conjunction with one or more different CRISPR nucleases and designed to target polynucleotide sequences of interest utilizing one or more different PAM sequences respective to the CRISPR nuclease utilized.

TABLE 1

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:852329_A_G | 1-41 | 42-63 | 64-95 |
| 19:852330_T_G | 1, 20, 31, 96-135 | 136-157 | 65-66, 158-188 |
| 19:852331_G_C | 31, 97, 114, 189-228 | 229-269 | 65, 158, 270-312 |
| 19:852338_G_A | 313-358 | 359-406 | 407-456 |
| 19:852342_G_A | 457-502 | 503-550 | 551-600 |
| 19:852343_CCG_CCGCC G | 313-315, 344, 601-620 | 359-360, 391, 400, 621-632 | 407, 417, 440, 450, 633-652 |
| 19:852350_G_A | 653-698 | 699-746 | 747-796 |
| 19:852351_C_T | 656, 665-666, 670, 684, 698, 797-836 | 702, 712, 717-718, 731, 740, 837-878 | 753, 759, 767-768, 781, 790, 879-922 |
| 19:852366_C_G | 923-968 | 969-1016 | 1017-1066 |
| 19:852367_C_G | 926-927, 933, 939, 948, 950, 1067-1106 1149-1192 | 974, 980, 983, 986, 995, 997, 1107-1148 | 1022, 1029, 1032, 1035, 1047, 1049, |
| 19:852380_G_C | 1193-1238 | 1239-1284 | 1285-1334 |
| 19:852392_G_C | 1335-1380 | 1381-1426 | 1427-1476 |
| 19:852395_GG_G | 1369, 1377, 1380, 1477-1509 | 1411, 1414, 1426, 1510-1544 | 1434, 1461, 1464, 1545-1581 |
| 19:852396_G_T | 1486-1487, 1492, 1497, 1505, 1582-1622 | 1520, 1525, 1530, 1538-1539, 1623-1665 | 1555, 1560, 1571, 1574-1575, 1666-1710 |
| 19:852864_G_T | 1711-1756 | 1757-1803 | 1804-1852 |
| 19:852878_A_C | 1853-1880 | 1881-1896 | 1897-1918 |
| 19:852882_C_T | 1919-1964 | 1965-2012 | 2013-2062 |
| 19:852885_T_C | 1940, 1946, 2063-2088 | 1988, 1991, 2089-2112 | 2037, 2050, 2113-2140 |
| 19:852898_T_G | 2141-2179 | 2180-2211 | 2212-2248 |
| 19:852927_C_T | 2249-2283 | 2284-2310 | 2311-2339 |
| 19:852933_C_T | 2340-2378 | 2379-2417 | 2418-2458 |
| 19:852935_T_C | 2350, 2364, 2459-2493 | 2395, 2403, 2494-2528 | 2434, 2446, 2529-2565 |
| 19:852937_C_A | 2476, 2484, 2566-2606 | 2512, 2520, 2607-2648 | 2546, 2548, 2649-2692 |
| 19:852939_T_G | 2582, 2584, 2586, 2693-2734 | 2623, 2644, 2735-2777 | 2670, 2688, 2778-2822 |
| 19:852941_GTGTCCC_G | 2823-2863 | 2864-2906 | 2907-2951 |
| 19:852941_G_A | 2714, 2720, 2726, 2731, 2832, 2952-2992 | 2751, 2758, 2770, 2875, 2993-3034 | 2795, 2801, 2810, 2934, 3035-3079 |
| 19:852941_G_C | 2714, 2720, 2726, 2731, 2832, 2964, 3118-3157 2967, 2980, 3080-3117 | 2751, 2758, 2770, 2875, 3019, 3021, | 2795, 2801, 2810, 2934, 3068, 3070, 3078, 3158-3199 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
| --- | --- | --- | --- |
| 19:852941_G_T | 2714, 2720, 2726, 2731, 2832, 2964, 2967, 2980, 3200-3237 | 2751, 2758, 2770, 2875, 3019, 3021, 3238-3277 | 2795, 2801, 2810, 2934, 3068, 3070, 3078, 3278-3319 |
| 19:852942_T_A | 2714, 2720, 2831-2832, 2964, 2967, 2980, 3320-3358 | 2751, 2770, 2874-2875, 3019, 3021, 3359-3399 | 2801, 2810, 2919, 2934, 3068, 3070, 3078, 3400-3442 |
| 19:852945_C_A | 2824, 2826, 2828, 2831, 2856, 3350, 3443-3482 | 2864, 2868, 2870, 2873-2874, 3398, 3483-3524 | 2907, 2917-2919, 2931, 3436, 3525-3568 |
| 19:852945_C_G | 2824, 2826, 2828, 2831, 2856, 3350, 3455, 3479, 3569-3606 | 2864, 2868, 2870, 2873-2874, 3398, 3483, 3515, 3607-3645 | 2907, 2917-2919, 2931, 3436, 3528, 3530, 3646-3687 |
| 19:852945_C_T | 2824, 2826, 2828, 2831, 2856, 3350, 3455, 3479, 3688-3725 | 2864, 2868, 2870, 2873-2874, 3398, 3483, 3515, 3726-3765 | 2907, 2917-2919, 2931, 3436, 3528, 3530, 3766-3807 |
| 19:852948_T_C | 2823, 2826, 2844, 3455, 3808-3845 | 2864, 2866, 2887, 3483, 3846-3877 | 2909, 2914, 2931, 3530, 3878-3915 |
| 19:852948_T_G | 2823, 2826, 2844, 3455, 3808, 3821, 3829, 3834, 3916-3949 | 2864, 2866, 2887, 3483, 3849, 3856, 3858, 3866, 3950-3977 | 2909, 2914, 2931, 3530, 3879, 3892, 3898, 3903, 3978-4011 |
| 19:852954_T_C | 4012-4053 | 4054-4089 | 4090-4131 |
| 19:852965_C_T | 4132-4177 | 4178-4225 | 4226-4275 |
| 19:852966_A_T | 4133, 4139, 4143, 4169, 4172-4173, 4276-4315 | 4179, 4185-4186, 4216, 4221, 4225, 4316-4356 | 4227, 4234, 4250, 4266, 4268, 4275, 4357-4400 |
| 19:852967_C_A | 4133, 4139, 4143, 4173, 4282, 4288, 4401-4440 | 4179, 4186, 4216, 4221, 4338, 4441-4482 | 4234, 4250, 4266, 4275, 4371, 4397, 4483-4526 |
| 19:852971_T_A | 4527-4572 | 4573-4620 | 4621-4670 |
| 19:852972_G_A | 4529, 4536, 4550, 4553, 4561, 4563, 4671-4710 | 4582, 4597, 4608, 4610, 4616, 4619, 4711-4752 | 4641, 4646, 4659, 4665, 4668, 4670, 4753-4796 |
| 19:852972_G_C | 4529, 4536, 4550, 4553, 4561, 4563, 4696, 4709, 4797-4834 | 4582, 4597, 4608, 4610, 4616, 4619, 4713, 4752, 4835-4874 | 4641, 4646, 4659, 4665, 4668, 4670, 4761, 4790, 4875-4916 |
| 19:852974_G_C | 4529, 4563, 4696, 4709, 4917-4958 | 4582, 4619, 4713, 4752, 4959-5002 | 4646, 4670, 4761, 4790, 5003-5048 |
| 19:852976_C_CCTGATT | 4955, 5049-5092 | 4976, 5093-5138 | 5033, 5139-5186 |

TABLE 1-continued

Guide sequences designed to target mutant
alleles the ELANE gene

| Target | SEQ ID NOs: of 20 base guides | SEQ ID NOs: of 21 base guides | SEQ ID NOs: of 22 base guides |
|---|---|---|---|
| 19:852977_G_A | 4951,4955, 5064, 5075-5076, 5187-5227 | 4963,4976, 5108, 5119, 5135, 5228-5270 | 5003,5033, 5157, 5166, 5182, 5271-5315 |
| 19:852977_G_T | 4951,4955, 5064, 5075-5076, 5187, 5192, 5204, 5316-5353 | 4963,4976, 5108, 5119, 5135, 5228, 5239, 5245, 5354-5393 | 5003,5033, 5157, 5166, 5182, 5272, 5283, 5290, 5394-5435 |
| 19:852978_C_T | 5064, 5075-5076, 5187, 5192, 5204, 5436-5475 | 5108, 5119, 5135, 5228, 5239, 5245, 5476-5517 | 5157, 5166, 5182, 5272, 5283, 5290, 5518-5561 |
| 19:852980_A_C | 5076, 5204, 5445, 5447, 5562-5603 | 5108, 5239, 5477, 5498, 5604-5637 | 5166, 5272, 5530, 5536, 5638-5677 |
| 19:852984_T_C | 5678-5723 | 5724-5765 | 5766-5811 |
| 19:852984_T_G | 5680, 5684, 5687, 5691, 5693, 5708, 5712, 5719, 5812-5849 | 5726, 5730, 5733, 5737, 5750, 5752, 5755, 5757, 5850-5883 | 5768, 5772, 5779, 5786, 5793, 5795, 5801-5802, 5884-5921 |
| 19:852986_ATTGC_AG | 5693, 5922-5963 | 5755, 5964-6003 | 5802, 6004-6049 |
| 19:852987_T_C | 5680, 5693, 5926, 5930, 5934, 5944, 6050-6089 | 5750, 5755, 5968, 5972, 5975, 5993, 6090-6125 | 5786, 5802, 6012, 6015, 6033, 6039, 6126-6165 |
| 19:852988_TGCGCCAA CTTCGTCATGTCGGCC_T | 6166-6202 | 6203-6241 | 6242-6282 |
| 19:852988_T_G | 5926, 5930, 5934, 5944, 5950, 6064, 6071, 6283-6321 | 5968, 5972, 5975, 5993, 5996, 6103, 6106, 6322-6356 | 6012, 6015, 6023, 6033, 6039, 6140, 6154, 6357-6395 |
| 19:852990_C_G | 5934, 5938, 5944, 5950, 5953, 6188, 6320, 6396-6434 | 5968, 5977, 5983, 5993, 5996, 6236, 6340, 6435-6475 | 6012, 6023, 6034, 6037, 6039, 6281, 6361, 6476-6518 |
| 19:852990_C_T | 5934, 5944, 5950, 5953, 6188, 6320, 6411, 6427, 6519-6556 | 5968, 5983, 5993, 5996, 6236, 6340, 6461, 6473, 6557-6596 | 6012, 6023, 6037, 6039, 6281, 6361, 6493, 6497, 6597-6638 |
| 19:852998_TTCG_T | 6639-6679 | 6680-6722 | 6723-6767 |
| 19:853001_G_T | 6641-6642, 6644, 6648-6650, 6653, 6655, 6659, 6664, 6667, 6768-6802 | 6682-6683, 6689-6691, 6694-6695, 6701, 6706, 6709-6710, 6803-6839 | 6726, 6732-6733, 6737-6738, 6744-6745, 6750, 6753-6755, 6840-6878 |
| 19:853002_TCATGTCGG CCGCGCAC_TA | 6641, 6655, 6879-6921 | 6682, 6689, 6922-6966 | 6732, 6737, 6967-7013 |
| 19:853002_T_A | 6641-6642, 6648-6649, 6655, 6659, 6897, 7014-7052 | 6682-6683, 6689-6690, 6694-6695, 6940, 7053-7092 | 6732-6733, 6737-6738, 6754-6755, 6970, 7093-7134 |
| 19:853005_T_G | 6897, 6904, 7024, 7135-7176 | 6940-6941, 7177-7218 | 6970, 6986, 7219-7264 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:853007_TCGGCCG_T | 6166, 6173-6174, 7265-7302 | 6203, 6210, 6234, 7303-7342 | 6249, 6263, 6274, 7343-7384 |
| 19:853008_C_G | 7158, 7170, 7298, 7302, 7385-7425 | 7213, 7216, 7310, 7342, 7426-7464 | 7225, 7243, 7352, 7367, 7465-7508 |
| 19:853019_T_A | 6902, 6913, 7509-7550 | 6946, 6955, 7551-7590 | 7001-7002, 7591-7636 |
| 19:853019_T_C | 6902, 6913, 7514, 7532, 7537, 7540, 7547, 7550, 7637-7666 | 6946, 6955, 7551, 7557, 7572, 7576, 7582, 7590, 7667-7696 | 7001-7002, 7591, 7597, 7600, 7610, 7615, 7620, 7697-7730 |
| 19:853020_G_A | 6902, 7532, 7537, 7540, 7547, 7550, 7731-7770 | 6955, 7557, 7572, 7576, 7582, 7590, 7771-7812 | 7002, 7591, 7597, 7610, 7615, 7620, 7813-7856 |
| 19:853020_G_T | 6902, 7532, 7537, 7540, 7547, 7550, 7750, 7752, 7857-7894 | 6955, 7557, 7572, 7576, 7582, 7590, 7786, 7810, 7895-7934 | 7002, 7591, 7597, 7610, 7615, 7620, 7827, 7856, 7935-7976 |
| 19:853022_G_A | 7540, 7547, 7750, 7752, 7977-8018 | 7572, 7590, 7786, 7810, 8019-8062 | 7610, 7620, 7827, 7856, 8063-8108 |
| 19:853023_T_A | 7750, 7752, 7992, 7994, 8009, 8013, 8109-8146 | 7786, 7810, 8034, 8040, 8052, 8057, 8147-8182 | 7827, 7856, 8084, 8087, 8102, 8105, 8183-8224 |
| 19:853023_T_G | 7750, 7752, 7992, 7994, 8009, 8013, 8118, 8141, 8225-8254 | 7786, 7810, 8034, 8040, 8052, 8057, 8166, 8179, 8255-8284 | 7827, 7856, 8084, 8087, 8102, 8105, 8186, 8216, 8285-8318 |
| 19:853025_G_A | 7992, 8013, 8118, 8141, 8319-8360 | 8052, 8057, 8166, 8179, 8361-8404 | 8084, 8087, 8186, 8216, 8405-8450 |
| 19:853265_CGTCCGCGC G_C | 8451-8491 | 8492-8534 | 8535-8579 |
| 19:853265_CGTCC_CCC TCCCCGGCAGGACCTCCCC GGCAGGTCCTCCCTCCCCG GCAGGACCG | 8477, 8490, 8580-8621 | 8514, 8520, 8622-8661 | 8557, 8568, 8662-8703 |
| 19:853270_GCGC_G | 8482, 8485-8486, 8489, 8704-8744 | 8519, 8528-8529, 8534, 8745-8785 | 8542, 8573, 8578-8579, 8786-8830 |
| 19:853270_G_A | 8476, 8489, 8723, 8728, 8733, 8831-8871 | 8519, 8533, 8763, 8778, 8784, 8872-8913 | 8563, 8578, 8817, 8825, 8829, 8914-8958 |
| 19:853272_G_C | 8482, 8485, 8723, 8728, 8733-8734, 8870, 8959-8993 | 8528-8529, 8763, 8767, 8778, 8784, 8900, 8994-9018 | 8573, 8579, 8805, 8817, 8825, 8829, 8951, 9019-9051 |
| 19:853272_G_T | 8482, 8485, 8723, 8728, 8733-8734, 8870, 8992, 9052-9089 | 8528-8529, 8763, 8767, 8778, 8784, 8900, 9011, 9090-9129 | 8573, 8579, 8805, 8817, 8825, 8829, 8951, 9038, 9130-9171 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:853273_CGGTGCG_C | 9172-9208 | 9209-9239 | 9240-9276 |
| 19:853276_T_G | 8486, 8491, 9185, 9188, 9204, 9277-9299 | 8499, 8534, 9221-9222, 9239, 9300-9313 | 8542, 8574, 9253-9254, 9271, 9314-9332 |
| 19:853278_C_T | 9185, 9188, 9193, 9198, 9203-9204, 9208, 9281, 9333-9370 | 9221-9222, 9224, 9231-9232, 9234, 9239, 9312, 9371-9410 | 9246, 9253-9255, 9257, 9269, 9271, 9332, 9411-9452 |
| 19:853279_G_C | 9178, 9188, 9193, 9198, 9201, 9203-9204, 9208, 9453-9486 | 9215, 9222, 9224, 9231-9232, 9234-9235, 9239, 9487-9510 | 9246, 9254-9255, 9257, 9262, 9269, 9271, 9276, 9511-9542 |
| 19:853281_G_A | 9193, 9201, 9203, 9461, 9543-9584 | 9215, 9231-9232, 9246, 9257, 9500, 9585-9628 | 9262, 9533, 9629-9674 |
| 19:853285_T_A | 9675-9717 | 9718-9751 | 9752-9791 |
| 19:853288_T_C | 9694, 9792-9825 | 9724, 9826-9849 | 9753, 9760, 9850-9878 |
| 19:853290_G_A | 9796, 9805, 9821, 9879-9920 | 9833, 9837, 9921-9962 | 9855, 9858, 9963-10007 |
| 19:853290_G_C | 9796, 9805, 9821, 9882, 9885, 9887, 9898, 10008-10045 | 9833, 9837, 9924-9925, 10046-10082 | 9855, 9858, 9966, 9999-10000, 10083-10121 |
| 19:853291_G_A | 9805, 9882, 9885, 9887, 9898, 10122-10161 | 9833, 9924-9925, 10162-10202 | 9855, 9966, 9999-10000, 10203-10245 |
| 19:853293_G_T | 9882, 9898, 10125, 10130, 10246-10287 | 9924, 10195, 10288-10330 | 9999, 10214, 10331-10375 |
| 19:853295_CCATAACCT CTC_CCATAACCTCTCCCA TAACCTCTC | 10376-10398 | 10399-10423 | 10424-10450 |
| 19:853295_CCAT_C | 10256, 10451-10494 | 10309, 10495-10538 | 10342, 10539-10584 |
| 19:853302_C_T | 10585-10627 | 10628-10671 | 10672-10717 |
| 19:853312_G_A | 10718-10759 | 10760-10795 | 10796-10835 |
| 19:853327_A_C | 10836-10868 | 10869-10893 | 10894-10924 |
| 19:853327_A_T | 10840, 10842, 10857, 10868, 10925-10957 | 10870, 10873, 10875, 10886, 10958-10988 | 10895, 10898, 10912, 10914, 10989-11021 |
| 19:853329_G_A | 10840, 10857, 11022-11061 | 10870, 10873, 11062-11102 | 10895, 10912, 11103-11145 |
| 19:853329_G_T | 10840, 10857, 11023, 11046, 11146-11183 | 10870, 10873, 11079, 11086, 11184-11222 | 10895, 10912, 11121, 11143, 11223-11263 |
| 19:853333_T_C | 11264-11308 | 11309-11345 | 11346-11388 |
| 19:853335_G_A | 11295, 11298, 11307-11308, 11389-11430 | 11334, 11344-11345, 11431-11474 | 11363, 11380, 11388, 11475-11520 |
| 19:853338_G_A | 11393, 11423, 11521-11564 | 11450, 11453, 11565-11610 | 11490, 11505, 11611-11658 |

TABLE 1-continued

Guide sequences designed to target mutant
alleles the ELANE gene

| Target | SEQ ID NOs: of 20 base guides | SEQ ID NOs: of 21 base guides | SEQ ID NOs: of 22 base guides |
|---|---|---|---|
| 19:853338_G_T | 11393, 11423, 11531, 11533, 11536, 11541, 11548-11549, 11659-11696 | 11450, 11453, 11568-11569, 11579, 11582, 11593-11594, 11697-11736 | 11490, 11505, 11614-11615, 11635, 11640-11641, 11649, 11737-11778 |
| 19:853342_A_C | 11779-11824 | 11825-11872 | 11873-11922 |
| 19:853345_G_C | 11789, 11797, 11923-11966 | 11834, 11865, 11967-12012 | 11874, 11907, 12013-12060 |
| 19:853345_G_T | 11789, 11797, 11936, 11942, 11946, 11948, 11951, 11959, 12061-12098 | 11834, 11865, 11976, 11981, 11992, 11994-11995, 11998, 12099-12138 | 11874, 11907, 12022-12023, 12028, 12041-12043, 12139-12180 |
| 19:853348_T_A | 11942, 11948, 12181-12224 | 11992, 11994, 12225-12270 | 12028, 12041, 12271-12318 |
| 19:853370_C_G | 12319-12364 | 12365-12412 | 12413-12462 |
| 19:853372_TAAACTTGC TCAACGACATCGTGAT_T | 12362, 12463-12503 | 12391, 12504-12545 | 12456, 12546-12589 |
| 19:853375_A_T | 12479, 12488, 12590-12633 | 12520, 12543, 12634-12679 | 12587, 12589, 12680-12727 |
| 19:853379_G_T | 12728-12773 | 12774-12821 | 12822-12871 |
| 19:853384_A_G | 12872-12917 | 12918-12965 | 12966-13015 |
| 19:853390_T_A | 13016-13061 | 13062-13109 | 13110-13159 |
| 19:853395_A_T | 12481, 12493, 13160-13201 | 12522, 13202-13245 | 12559, 13246-13291 |
| 19:853396_T_A | 12481, 13161, 13164, 13168, 13292-13330 | 13203, 13206, 13239, 13331-13371 | 13247, 13282, 13285, 13372-13414 |
| 19:853396_T_G | 12481, 13161, 13164, 13168, 13312, 13415-13452 | 13203, 13206, 13239, 13336, 13453-13491 | 13247, 13282, 13285, 13373, 13492-13532 |
| 19:853398_C_T | 13168, 13312, 13533-13572 | 13206, 13336, 13573-13613 | 13247, 13373, 13614-13656 |
| 19:853399_T_A | 13312, 13568, 13570, 13657-13692 | 13336, 13594, 13611, 13693-13728 | 13373, 13619, 13637, 13729-13766 |
| 19:853399_T_C | 13312, 13568, 13570, 13681, 13767-13799 | 13336, 13594, 13611, 13726, 13800-13832 | 13373, 13619, 13637, 13766, 13833-13867 |
| 19:853401_C_T | 13568, 13681, 13868-13904 | 13611, 13726, 13905-13939 | 13637, 13766, 13940-13976 |
| 19:855553_C_CAC | 13977-14017 | 14018-14060 | 14061-14105 |
| 19:855556_C_A | 13979, 13988-13989, 13999, 14001, 14106-14146 | 14020, 14030-14031, 14039, 14042, 14147-14189 | 14063, 14074, 14083, 14086, 14099, 14190-14234 |
| 19:855563_G_C | 14235-14280 | 14281-14328 | 14329-14378 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:855564_C_T | 14239, 14255, 14262-14263, 14275, 14280, 14379-14418 | 14285, 14301, 14306, 14318, 14323, 14328, 14419-14460 | 14333, 14352, 14356, 14368, 14371, 14378, 14461-14504 |
| 19:855565_T_A | 14255, 14262, 14275, 14280, 14384, 14411, 14505-14544 | 14285, 14301, 14318, 14328, 14440, 14444, 14545-14586 | 14333, 14352, 14356, 14368, 14480, 14490, 14587-14630 |
| 19:855568_A_T | 14524, 14539, 14631-14674 | 14549, 14572, 14675-14720 | 14610, 14616, 14721-14768 |
| 19:855574_C_G | 14769-14814 | 14815-14862 | 14863-14912 |
| 19:855574_C_T | 14771, 14773, 14778-14779, 14783, 14785, 14790, 14793, 14913-14950 | 14819, 14824-14825, 14829, 14831-14832, 14840, 14856, 14951-14990 | 14873, 14877, 14879-14880, 14887, 14889, 14904, 14906, 14991-15032 |
| 19:855575_G_A | 14771, 14773, 14778-14779, 14783, 14793, 15033-15072 | 14824-14825, 14829, 14831, 14840, 14856, 15073-15114 | 14877, 14879-14880, 14887, 14889, 14906, 15115-15158 |
| 19:855576_GCCA_G | 15159-15197 | 15198-15238 | 15239-15281 |
| 19:855576_G_C | 14771, 14778-14779, 14793, 15043, 15067, 15178, 15282-15320 | 14824, 14829, 14840, 14856, 15075, 15092, 15212, 15321-15361 | 14877, 14879, 14887, 14906, 15124, 15130, 15241, 15362-15404 |
| 19:855577_C_A | 14771, 14793, 15043, 15067, 15172, 15178, 15181, 15292, 15405-15442 | 14824, 14856, 15075, 15092, 15200, 15212-15213, 15332, 15443-15482 | 14877, 14887, 15124, 15130, 15241, 15248, 15253, 15364, 15483-15524 |
| 19:855580_C_T | 15160-15161, 15164, 15167-15168, 15170-15172, 15179, 15181, 15183, 15193, 15525-15558 | 15199-15200, 15203, 15206-15207, 15209-15211, 15213, 15220, 15222, 15234, 15559-15594 | 15240, 15247-15248, 15250-15253, 15255, 15262, 15264-15265, 15277, 15595-15632 |
| 19:855582_ATCA_A | 15160, 15533, 15633-15672 | 15206, 15577, 15673-15714 | 15251, 15618, 15715-15758 |
| 19:855588_G_A | 15759-15804 | 15805-15852 | 15853-15902 |
| 19:855591_A_C | 15764, 15774, 15903-15946 | 15806, 15833, 15947-15992 | 15863, 15886, 15993-16040 |
| 19:855604_C_A | 16041-16086 | 16087-16133 | 16134-16182 |
| 19:855604_C_T | 16048-16049, 16053, 16060, 16070, 16074, 16078, 16081, 16183-16220 | 16094, 16099, 16101, 16107, 16117, 16121, 16128, 16221-16260 | 16136, 16142, 16147, 16149, 16155, 16166, 16170, 16261-16302 |
| 19:855613_C_G | 16303-16346 | 16347-16377 | 16378-16417 |
| 19:855613_C_T | 16303-16304, 16309, 16314, 16316, 16324, 16330, 16344, 16418-16455 | 16347-16348, 16352, 16355, 16375, 16377, 16456-16495 | 16378, 16384, 16387, 16400, 16410, 16414, 16417, 16496-16537 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:855616_C_T | 16324, 16344, 16538-16581 | 16348, 16377, 16582-16626 | 16378, 16410, 16627-16673 |
| 19:855624_C_T | 16674-16719 | 16720-16765 | 16766-16815 |
| 19:855625_G_A | 16686, 16696, 16699, 16701, 16709, 16715, 16816-16855 | 16721, 16743, 16747, 16761, 16764, 16856-16897 | 16767, 16773, 16790, 16803, 16808, 16814, 16898-16941 |
| 19:855627_C_T | 16686, 16696, 16818, 16827, 16942-16983 | 16721, 16747, 16863, 16869, 16984-17027 | 16773, 16803, 16923-16924, 17028-17073 |
| 19:855628_G_A | 16818, 16827, 16944, 16948, 16950, 16967, 17074-17113 | 16863, 16869, 16991, 16994, 17010, 17018, 17114-17155 | 16923-16924, 17032, 17040, 17042, 17064, 17156-17199 |
| 19:855634_G_A | 17200-17244 | 17245-17288 | 17289-17335 |
| 19:855639_G_A | 17336-17381 | 17382-17428 | 17429-17477 |
| 19:855648_T_A | 17478-17523 | 17524-17568 | 17569-17617 |
| 19:855649_G_A | 17479, 17483, 17497, 17499, 17510, 17514, 17618-17657 | 17525, 17529, 17543, 17545, 17549, 17658-17699 | 17570, 17573, 17590, 17596, 17603, 17700-17743 |
| 19:855649_G_C | 17479, 17483, 17497, 17499, 17510, 17514, 17635, 17638, 17744-17781 | 17525, 17529, 17543, 17545, 17549, 17660, 17684, 17782-17820 | 17570, 17573, 17590, 17596, 17603, 17708, 17720, 17821-17862 |
| 19:855649_G_T | 17479, 17483, 17497, 17499, 17510, 17514, 17635, 17638, 17863-17900 | 17525, 17529, 17543, 17545, 17549, 17660, 17684, 17901-17940 | 17570, 17573, 17590, 17596, 17603, 17708, 17720, 17941-17982 |
| 19:855650_C_G | 17479, 17483, 17499, 17510, 17635, 17638, 17983-18022 | 17525, 17543, 17545, 17549, 17660, 17684, 18023-18062 | 17573, 17590, 17596, 17603, 17708, 17720, 18063-18106 |
| 19:855652_T_C | 17635, 17638, 17985, 18002, 18107-18144 | 17660, 17684, 18031, 18042, 18145-18180 | 17708, 17720, 18076, 18092, 18181-18220 |
| 19:855653_G_A | 17985, 18002, 18115, 18119, 18135, 18144, 18221-18260 | 18031, 18042, 18155, 18158, 18165, 18180, 18261-18302 | 18076, 18092, 18194, 18201, 18204, 18208, 18303-18346 |
| 19:855654_G_C | 18115, 18119, 18135, 18144, 18234, 18249, 18347-18386 | 18155, 18158, 18165, 18180, 18285, 18293, 18387-18426 | 18194, 18201, 18204, 18208, 18343, 18346, 18427-18470 |
| 19:855655_C_A | 18119, 18135, 18234, 18249, 18368, 18370, 18471-18510 | 18158, 18180, 18285, 18293, 18414, 18423, 18511-18552 | 18204, 18208, 18343, 18346, 18448, 18460, 18553-18596 |
| 19:855663_T_C | 18597-18638 | 18639-18674 | 18675-18716 |
| 19:855665_G_C | 18598, 18615, 18629, 18633, 18717-18758 | 18640, 18644, 18665, 18667, 18759-18800 | 18680, 18684, 18706-18707, 18801-18846 |
| 19:855669_C_G | 18847-18892 | 18893-18939 | 18940-18989 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:855687_G_A | 18990-19035 | 19036-19083 | 19084-19133 |
| 19:855687_G_C | 19000, 19006-19007, 19016, 19022, 19025-19026, 19030, 19134-19171 | 19046, 19052, 19064, 19069, 19072-19073, 19077, 19082, 19172-19211 | 19087, 19101, 19105, 19114, 19122-19123, 19127, 19132, 19212-19253 |
| 19:855690_A_G | 19006, 19016, 19254-19297 | 19064, 19069, 19298-19343 | 19087, 19122, 19344-19391 |
| 19:855693_G_A | 19276, 19297, 19392-19435 | 19317, 19338, 19436-19481 | 19354, 19391, 19482-19529 |
| 19:855699_G_A | 19530-19575 | 19576-19623 | 19624-19673 |
| 19:855706_A_C | 19674-19719 | 19720-19767 | 19768-19817 |
| 19:855712_T_C | 19818-19863 | 19864-19911 | 19912-19961 |
| 19:855715_ACGTGACGGTGGTGACGTCCCTCTG_A | 19962-20004 | 20005-20049 | 20050-20096 |
| 19:855736_T_TCT | 20097-20137 | 20138-20180 | 20181-20225 |
| 19:855739_GC_G | 19969, 19986, 19996, 20116, 20132, 20226-20263 | 20009, 20013, 20030, 20170, 20175, 20264-20303 | 20054, 20075, 20077, 20197, 20214, 20304-20345 |
| 19:855741_CG_C | 19986, 20116, 20227, 20231, 20237, 20346-20385 | 20009, 20175, 20265, 20281, 20284, 20386-20427 | 20075, 20214, 20314, 20323, 20338, 20428-20471 |
| 19:855753_G_A | 20472-20517 | 20518-20565 | 20566-20615 |
| 19:855755_C_A | 20487-20488, 20494, 20513, 20616-20657 | 20535, 20554, 20557, 20561, 20658-20701 | 20590, 20603, 20606, 20614, 20702-20747 |
| 19:855758_C_A | 20637, 20656, 20748-20791 | 20674, 20682, 20792-20836 | 20715, 20720, 20837-20883 |
| 19:855764_C_G | 20884-20924 | 20925-20963 | 20964-21004 |
| 19:855765_G_A | 20899, 20916, 20919, 21005-21043 | 20943, 20956, 20959, 21044-21081 | 20977, 20982, 20997, 21082-21121 |
| 19:855767_G_A | 20899, 21031, 21122-21160 | 20959, 21058, 21161-21195 | 20997, 21117, 21196-21235 |
| 19:855770_G_C | 21125, 21236-21266 | 21167, 21267-21295 | 21196, 21222, 21296-21326 |
| 19:855770_G_T | 21125, 21236-21239, 21242, 21254, 21327-21360 | 21167, 21267-21268, 21272-21273, 21284-21285, 21361-21387 | 21196, 21222, 21296, 21300, 21303, 21307, 21314-21315, 21388-21421 |
| 19:855775_G_A | 21422-21463 | 21464-21497 | 21498-21539 |
| 19:855777_C_T | 21442, 21454, 21457, 21460, 21540-21577 | 21476, 21490-21491, 21495, 21578-21607 | 21504, 21516-21517, 21532, 21608-21645 |
| 19:855778_AG_CT | 21442, 21545, 21557, 21563, 21577, 21646-21670 | 21495, 21582, 21584, 21594, 21607, 21671-21693 | 21532, 21616, 21627, 21629, 21643, 21694-21720 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:855779_G_GGC | 21545, 21557, 21721-21739 | 21582, 21584, 21740-21756 | 21616, 21629, 21757-21777 |
| 19:855780_GC_G | 21652, 21725, 21729, 21731-21732, 21738-21739, 21778-21799 | 21685, 21743, 21745, 21750, 21756, 21800-21821 | 21713, 21761, 21763, 21767, 21770, 21772, 21777, 21822-21845 |
| 19:855783_G_GGC | 21793, 21797, 21846-21866 | 21805, 21819, 21867-21887 | 21827, 21830, 21888-21910 |
| 19:855785_C_CGTCTGTTT | 21911-21938 | 21939-21967 | 21968-21998 |
| 19:855786_G_A | 21999-22038 | 22039-22073 | 22074-22115 |
| 19:855786_G_GCT | 22013, 22015, 22116-22146 | 22052-22053, 22147-22175 | 22078, 22092, 22176-22206 |
| 19:855786_G_GTTTTT | 22207-22243 | 22244-22280 | 22281-22321 |
| 19:855795_G_A | 21922, 21925, 21931, 22322-22364 | 21951, 21960, 22365-22409 | 21990, 21994, 22410-22456 |
| 19:855795_G_C | 21922, 21925, 21931, 22325, 22327, 22332, 22344, 22351, 22457-22494 | 21951, 21960, 22368, 22375, 22382, 22388, 22390, 22495-22534 | 21990, 21994, 22413-22414, 22421, 22427, 22437, 22535-22576 |
| 19:855795_G_T | 21922, 21925, 21931, 22325, 22327, 22332, 22344, 22351, 22577-22614 | 21951, 21960, 22368, 22375, 22382, 22388, 22390, 22615-22654 | 21990, 21994, 22413-22414, 22421, 22427, 22437, 22655-22696 |
| 19:855797_A_T | 21925, 22325, 22332, 22351, 22697-22738 | 21951, 22375, 22382, 22390, 22739-22782 | 21990, 22414, 22427, 22437, 22783-22828 |
| 19:855799_G_A | 22700, 22706, 22720-22721, 22829-22870 | 22743, 22761, 22764, 22769, 22871-22914 | 22799, 22806, 22813, 22815, 22915-22960 |
| 19:855799_G_T | 22700, 22706, 22720-22721, 22833, 22850, 22856, 22858, 22961-22998 | 22743, 22761, 22764, 22769, 22875, 22881, 22899, 22904, 22999-23038 | 22799, 22806, 22813, 22815, 22926, 22940, 22949, 22951, 23039-23080 |
| 19:855955_CAG_C | 23081-23125 | 23126-23168 | 23169-23215 |
| 19:855955_C_G | 23081, 23087, 23094, 23118, 23124, 23216-23256 | 23132, 23134, 23149, 23161, 23167, 23257-23298 | 23170, 23179, 23194, 23201, 23214, 23299-23343 |
| 19:855956_AG_A | 23081-23082, 23087, 23090, 23344-23376 | 23127, 23132, 23134, 23151, 23377-23411 | 23170, 23173, 23179, 23196, 23412-23448 |
| 19:855957_G_A | 23081-23082, 23087, 23090, 23093-23094, 23118, 23346, 23449-23486 | 23127, 23132, 23134, 23137, 23151, 23161, 23167, 23377, 23487-23526 | 23170, 23173, 23179, 23194, 23196, 23208, 23214, 23417, 23527-23568 |
| 19:855958_G_GGGGACTCC | 23569-23593 | 23594-23618 | 23619-23647 |
| 19:855959_GGGACTC_G | 23345, 23354, 23359, 23648-23685 | 23379, 23383, 23389, 23686-23723 | 23414, 23419, 23422, 23724-23765 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
| --- | --- | --- | --- |
| 19:855960_GG_GGGG | 23081, 23087, 23090, 23218, 23345, 23354, 23359, 23685, 23766-23767 | 23127, 23132, 23134, 23257, 23379, 23383, 23389, 23705, 23768-23769 | 23170, 23179, 23196, 23305, 23414, 23419, 23422, 23739, 23770-23773 |
| 19:855965sj | 23662, 23677, 23684-23685, 23774-23815 | 23699, 23701, 23705, 23715, 23816-23859 | 23736-23737, 23739-23740, 23860-23905 |
| 19:855967_G_C | 23581, 23593, 23660, 23662, 23677, 23808, 23810, 23906-23944 | 23606, 23616, 23698-23699, 23701, 23850, 23856, 23945-23983 | 23642, 23645, 23736-23737, 23748, 23902, 23905, 23984-24026 |
| 19:855967_G_T | 23581, 23593, 23660, 23662, 23677, 23808, 23810, 23920, 24027-24064 | 23606, 23616, 23698-23699, 23701, 23850, 23856, 23967, 24065-24104 | 23642, 23645, 23736-23737, 23748, 23902, 23905, 23989, 24105-24146 |
| 19:855968_G_A | 23581, 23584, 23593, 23660, 23662, 23810, 23920, 24147-24185 | 23606, 23616, 23618, 23698-23699, 23850, 23967, 24186-24226 | 23631, 23642, 23645, 23736, 23748, 23902, 23989, 24227-24269 |
| 19:855971_GC_G | 24270-24308 | 24309-24349 | 24350-24392 |
| 19:855974_C_G | 24271, 24279, 24281, 24286, 24307, 24393-24433 | 24318, 24320, 24325, 24334, 24345, 24434-24474 | 24366, 24372, 24376, 24381, 24388, 24475-24519 |
| 19:855977_T_C | 24271, 24284, 24423, 24520-24562 | 24310, 24320, 24472, 24563-24601 | 24361, 24366, 24512, 24602-24644 |
| 19:855978_G_T | 24284, 24525, 24538, 24553-24554, 24560, 24645-24684 | 24310, 24568, 24576, 24580, 24594, 24685-24726 | 24361, 24602, 24612, 24617, 24621, 24639, 24727-24770 |
| 19:855982_T_C | 24771-24816 | 24817-24864 | 24865-24914 |
| 19:855982_T_G | 24771-24772, 24776, 24792, 24798, 24801, 24809, 24814, 24915-24952 | 24817, 24822-24823, 24839, 24845, 24848-24849, 24862, 24953-24992 | 24865, 24870-24871, 24889, 24894, 24897-24899, 24993-25034 |
| 19:855984_C_A | 24771-24772, 24776, 24792, 25035-25076 | 24817, 24823, 24839, 24845, 25077-25120 | 24871, 24889, 24894, 24897, 25121-25166 |
| 19:855986_A_T | 25038, 25050, 25055, 25066, 25167-25208 | 25077, 25093, 25098, 25103, 25209-25252 | 25122, 25125, 25143, 25149, 25253-25298 |
| 19:855988_G_A | 25170, 25180, 25184, 25195, 25299-25340 | 25212, 25223, 25231, 25244, 25341-25384 | 25272, 25275, 25283, 25290, 25385-25430 |
| 19:855988_G_T | 25170, 25180, 25184, 25195, 25319, 25323, 25326, 25328, 25431-25468 | 25212, 25223, 25231, 25244, 25346, 25358, 25369, 25372, 25469-25508 | 25272, 25275, 25283, 25290, 25386, 25391, 25401, 25405, 25509-25550 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:855989_G_T | 25170, 25184, 25319, 25323, 25326, 25328, 25551-25590 | 25223, 25231, 25346, 25358, 25369, 25372, 25591-25632 | 25283, 25290, 25386, 25391, 25401, 25405, 25633-25676 |
| 19:855997_C_T | 25677-25722 | 25723-25770 | 25771-25820 |
| 19:855998_A_C | 25689, 25693, 25699, 25706, 25720, 25722, 25821-25860 | 25735, 25737, 25739, 25741, 25747, 25770, 25861-25902 | 25783, 25785-25787, 25789, 25797, 25903-25946 |
| 19:855999_CG_C | 25689, 25835, 25853, 25947-25986 | 25735, 25874, 25901, 25987-26028 | 25783, 25940, 25946, 26029-26072 |
| 19:856000_G_A | 25689, 25720, 25835, 25853, 25962, 25979, 25982, 25984, 26073-26110 | 25735, 25770, 25874, 25901, 26007, 26020-26021, 26024, 26111-26150 | 25783, 25797, 25940, 25946, 26046, 26051, 26064, 26071, 26151-26192 |
| 19:856000_G_C | 25689, 25720, 25835, 25853, 25962, 25964, 25979, 25982, 25984, 26193-26229 | 25735, 25770, 25874, 25901, 26002, 26007, 26020-26021, 26024, 26230-26268 | 25783, 25797, 25940, 25946, 26044, 26046, 26051, 26064, 26071, 26269-26309 |
| 19:856000_G_T | 25689, 25720, 25835, 25853, 25962, 25979, 25982, 25984, 26310-26347 | 25735, 25770, 25874, 25901, 26007, 26020-26021, 26024, 26348-26387 | 25783, 25797, 25940, 25946, 26046, 26051, 26064, 26071, 26388-26429 |
| 19:856001_G_A | 25835, 25853, 25962, 25967, 25971, 25979, 25982, 25984-25986, 26430-26465 | 25874, 25901, 26007-26008, 26020-26021, 26024, 26026-26028, 26466-26503 | 25940, 25946, 26046, 26051-26052, 26064-26065, 26069, 26071-26072, 26504-26543 |
| 19:856001_G_T | 25835, 25853, 25962, 25967, 25979, 25982, 25984, 26451, 26544-26581 | 25874, 25901, 26007, 26020-26021, 26024, 26026, 26483, 26582-26621 | 25940, 25946, 26046, 26051, 26064-26065, 26071, 26533, 26622-26663 |
| 19:856007_C_T | 26664-26709 | 26710-26757 | 26758-26807 |
| 19:856008_CT_C | 26670, 26685, 26688, 26696, 26808-26848 | 26710, 26716, 26731, 26745, 26849-26891 | 26758, 26770, 26793, 26798, 26892-26936 |
| 19:856015_G_A | 26937-26982 | 26983-27027 | 27028-27075 |
| 19:856018_CG_C | 27076-27114 | 27115-27152 | 27153-27193 |
| 19:856019_G_A | 27077-27078, 27090, 27097, 27100, 27194-27234 | 27116-27118, 27135, 27144, 27235-27277 | 27155, 27160, 27175, 27183, 27185, 27278-27322 |
| 19:856021_G_T | 27077, 27090, 27096-27097, 27104, 27195, 27323-27362 | 27116-27117, 27128, 27141, 27144, 27239, 27363-27404 | 27154, 27160, 27168, 27183, 27185, 27287, 27405-27448 |
| 19:856025_G_A | 27076, 27449-27493 | 27134, 27494-27540 | 27181, 27541-27589 |

TABLE 1-continued

Guide sequences designed to target mutant alleles the ELANE gene

| Target | SEQ ID NOs: of 20 base guides | SEQ ID NOs: of 21 base guides | SEQ ID NOs: of 22 base guides |
|---|---|---|---|
| 19:856026_CT_T | 27454, 27463, 27480-27481, 27491, 27493, 27590-27628 | 27494, 27500, 27509, 27526, 27535, 27540, 27629-27665 | 27541, 27547-27548, 27557, 27562, 27584, 27666-27706 |
| 19:856029_C_A | 27611, 27625, 27707-27750 | 27633, 27664, 27751-27796 | 27671, 27706, 27797-27844 |
| 19:856034_C_A | 27845-27890 | 27891-27938 | 27939-27988 |
| 19:856036_G_T | 27845, 27852, 27861, 27887, 27989-28030 | 27898, 27915, 27935, 27938, 28031-28073 | 27960, 27963, 27970, 27988, 28074-28119 |
| 19:856043_AC_A | 28120-28158 | 28159-28199 | 28200-28242 |
| 19:856044_C_A | 28122, 28127, 28130-28131, 28142, 28150, 28243-28282 | 28161, 28163, 28167, 28170, 28182, 28198, 28283-28324 | 28208, 28211, 28221, 28224, 28236, 28241, 28325-28368 |
| 19:856044_C_G | 28122, 28127, 28130, 28142, 28150, 28247, 28261, 28268, 28369-28406 | 28163, 28167, 28170, 28182, 28198, 28301, 28308, 28313, 28407-28446 | 28211, 28221, 28224, 28236, 28241, 28351, 28356, 28359, 28447-28488 |
| 19:856047_CG_C | 28139, 28146, 28158, 28489-28530 | 28179, 28186, 28190, 28531-28574 | 28204, 28228, 28232, 28575-28620 |
| 19:856056_TG_T | 28621-28665 | 28666-28712 | 28713-28761 |
| 19:856056_T_TCCCCCCCCCCCCATA | 28627, 28631, 28640-28641, 28644, 28648-28653, 28658, 28762-28765 | 28672, 28677, 28687, 28690, 28694-28699, 28704-28705, 28766-28769 | 28719, 28724, 28735-28736, 28739, 28743-28748, 28753, 28770-28773 |
| 19:856057_GC_G | 28655, 28662, 28664, 28774-28809 | 28673, 28701, 28711, 28810-28847 | 28720, 28725, 28750, 28848-28887 |
| 19:856057_G_C | 28627, 28631, 28640-28641, 28648-28653, 28655-28656, 28658, 28662, 28664, 28763, 28765, 28888-28916 | 28672-28673, 28677, 28687, 28694-28699, 28701, 28704-28705, 28709, 28711, 28766-28767, 28917-28947 | 28719-28720, 28724-28725, 28735-28736, 28743-28748, 28750, 28753, 28760, 28771, 28773, 28948-28980 |
| 19:856061_CG_C | 28792, 28803, 28981-29021 | 28829, 28840, 29022-29064 | 28867, 28873, 29065-29109 |
| 19:856064_T_A | 28792, 28984, 28988, 29012-29013, 29110-29150 | 28840, 29029, 29044, 29047, 29055, 29151-29193 | 28867, 29086, 29088, 29091, 29101, 29194-29238 |
| 19:856064_T_G | 28792, 28984, 28988, 29012-29013, 29119, 29127, 29134, 29239-29276 | 28840, 29029, 29044, 29047, 29055, 29154, 29169, 29185, 29277-29316 | 28867, 29086, 29088, 29091, 29101, 29224, 29228, 29230, 29317-29358 |
| 19:856069_CA_C | 29359-29403 | 29404-29450 | 29451-29499 |
| 19:856069_C_T | 29364-29365, 29368, 29378, 29382, 29384, 29500-29539 | 29409, 29421, 29425, 29429, 29431, 29441, 29540-29581 | 29456, 29459, 29467, 29469, 29473, 29490, 29582-29625 |

TABLE 1-continued

Guide sequences designed to target mutant
alleles the ELANE gene

| Target | SEQ ID NOs: of 20 base guides | SEQ ID NOs: of 21 base guides | SEQ ID NOs: of 22 base guides |
|---|---|---|---|
| 19:856081_T_C | 29626-29671 | 29672-29719 | 29720-29769 |
| 19:856081_T_G | 29638-29639, 29641, 29644, 29646, 29652, 29659, 29669, 29770-29807 | 29677, 29685-29686, 29688, 29693, 29699-29700, 29707, 29808-29847 | 29725, 29733-29734, 29741-29742, 29748-29749, 29763, 29848-29889 |
| 19:856083_G_A | 29641, 29644, 29646, 29652, 29890-29931 | 29677, 29686, 29688, 29700, 29932-29975 | 29725, 29733-29734, 29742, 29976-30021 |
| 19:856083_G_C | 29641, 29644, 29646, 29652, 29895, 29906, 29914, 29917, 30022-30059 | 29677, 29686, 29688, 29700, 29945, 29949, 29955, 29958, 30060-30099 | 29725, 29733-29734, 29742, 29988, 29990-29991, 30001, 30100-30141 |
| 19:856084_A_T | 29644, 29652, 29895, 29906, 29914, 29917, 30142-30181 | 29677, 29688, 29945, 29949, 29955, 29958, 30182-30223 | 29734, 29742, 29988, 29990-29991, 30001, 30224-30267 |
| 19:856085_T_A | 29895, 29906, 29914, 29917, 30162, 30176, 30268-30307 | 29945, 29949, 29955, 29958, 30195, 30209, 30308-30349 | 29988, 29990-29991, 30001, 30248, 30259, 30350-30393 |
| 19:856087_G_T | 30162, 30176, 30280, 30292, 30394-30435 | 30195, 30209, 30340, 30345, 30436-30479 | 30248, 30259, 30365, 30379, 30480-30525 |
| 19:856106_C_T | 30526-30571 | 30572-30619 | 30620-30669 |
| 19:856108_G_A | 30540, 30556, 30559, 30566, 30670-30711 | 30579, 30602, 30604, 30614, 30712-30755 | 30627, 30643, 30649, 30651, 30756-30801 |
| 19:856111_G_T | 30673, 30695, 30802-30845 | 30733, 30738, 30846-30890 | 30770, 30772, 30891-30938 |
| 19:856144_C_T | 30939-30974 | 30975-31001 | 31002-31030 |
| 19:856145_C_T | 30953, 30970, 30974, 31031-31063 | 30986, 30998, 31001, 31064-31089 | 31009, 31015, 31030, 31090-31117 |

The indicated locations listed in column 1 of the Table 1 are based on gnomAD v3 database and UCSC Genome Browser assembly ID: hg38, Sequencing/Assembly provider ID: Genome Reference Consortium Human GRCh38.p12 (GCA_000001405.27). Assembly date: December 2013 initial release; December 2017 patch release 12. The SNP details are indicated by the listed SNP ID NOs. ("rs numbers"), which are based on the NCBI 2018 database of Single Nucleotide Polymorphisms (dbSNP)). The indicated DNA mutations are associated with Transcript Consequence NM_001972 as obtained from NCBI RefSeq genes.

For the foregoing embodiments, each embodiment disclosed herein is contemplated as being applicable to each of the other disclosed embodiment. For example, it is understood that any of the RNA molecules or compositions of the present invention may be utilized in any of the methods of the present invention.

As used herein, all headings are simply for organization and are not intended to limit the disclosure in any manner. The content of any individual section may be equally applicable to all sections.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Further, the examples herein below disclose methods utilizing SpCas9 and guide sequences suitable to target the SpCas9 to the disclosed ELANE pathogenic mutation sequences. The examples demonstrate the feasibility of the strategies disclosed. A person having ordinary skill in the art would understand that the same guides sequences may be used with different CRISPR nuclease to target the disclosed mutations to apply each of the specified strategies. Further, different guide sequences that target other CRISPR nucleases to the same mutations may be used together with the other nucleases to apply each of the specified strategies.

Experimental Details

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

CRISPR repeat (crRNA), transactivating crRNA (tracrRNA), nuclease polypeptide sequences, and PAM sequences were predicted from different metagenomic databases of sequences of environmental samples. The list of bacterial species/strains from which the CRISPR repeat, tracRNA and nuclease sequences were predicted is provided in Table 2.

TABLE 2

DNA and Protein Sequences of Nucleases

| Name | Source Organism | Protein Sequence SEQ ID NO: | Original ORF DNA Sequence SEQ ID NO: | Human optimized DNA Sequence SEQ ID NO: |
|---|---|---|---|---|
| OMNI-39 | Butyrivibrio sp. AC2005 | 31123 | 31127 | 31128 |
| OMNI-40 | Aliiarcobacter faecis | 31124 | 31129 | 31130 |
| OMNI-50 | Ezakiella peruensis strain M6.X2 | 31125 | 31131 | 31132 |
| OMNI-53 | Clostridium sp. AF02-29 | 31126 | 31133 | 31134 |

Construction of OMNI Nuclease Polypeptides

For construction of OMNI nuclease polypeptides, the open reading frame of each nuclease (OMNI) that was identified was codon optimized for *E. coli* and for human cell line expression. The *E. coli* optimized ORF was cloned into bacterial plasmid pb-NNC and the human optimized into the pmOMNI plasmid (Table 3).

TABLE 3 APPENDIX

Details of construct elements

| Element | Protein Sequence | DNA sequence |
|---|---|---|
| HA Tag | SEQ ID NO: 31141 | SEQ ID NO: 31142 |
| NLS | SEQ ID NO: 31143 | SEQ ID NO: 31144 |
| P2A | SEQ ID NO: 31145 | SEQ ID NO: 31146 |
| mCherry | SEQ ID NO: 31147 | SEQ ID NO: 31148 |

Prediction and Construction of sgRNA.

For each OMNI the sgRNA was predicted by detection of the CRISPR repeat array sequence (crRNA) and a transactivating crRNA (tracrRNA) in the bacterial genome. The native pre-mature crRNA and tracrRNA sequences were connected in-silico with tetra-loop 'gaaa' and the secondary structure elements of the duplex were predicted by using an RNA Secondary Structure prediction Web Tool available at rna.urmc.rochester.edu.

The predicted secondary structures of the full duplex RNA elements (crRNA-tracrRNA chimera) was used for identification of possible "nexus" and "hairpins" and the design of sgRNAs for each nuclease with various versions. By shortening the duplex at the upper stem at different locations, the crRNA and tracrRNA were connected with tetra-loop 'gaaa', thus generating possible sgRNA scaffolds (all sgRNA designs of all OMNIs are listed in Table 4). At least two versions of possible designed scaffolds for each OMNI were synthesized and 5' connected to a 22 nucleotide universal unique spacer sequence (T1, SEQ ID NO: 31149) and were cloned into a bacterial Guide expressing plasmid under a constitutive promoter and a mammalian expressing plasmid under a U6 promoter (pbGuide and pmGuide, accordantly, Table 3).

In order to overcome potential transcriptional and structural constraints and to assess the plasticity of the sgRNA scaffold in the human cellular environmental context, several versions of sgRNA were tested. In each case, the modifications represent small variations in the nucleotide sequence within the duplex and/or hairpins that were introduced to several synthetic sgRNAs (Table 4).

TABLE 3

Plasmids and Constructs

| Plasmid | Purpose | Elements | Example | SEQ ID NO (DNA Sequence) |
|---|---|---|---|---|
| pbNNC-2 | Expressing OMNI polypeptide in the bacterial system | T7 promoter HA Tag-Linker-OMNI ORF (Human optimized) - T7 terminator | pbNNC2 OMNI39 | 31135 |
| pbGuide T1/T2 | Expressing OMNI sgRNA in the bacterial system | J23119 promoter - T1/T2 spacer sgRNA scaffold - rrnB T1 terminator | pbGuide OMNI39 T2 sgRNA V2 | 31136 |
| pbPOS T2 library | Bacterial/TXTL depletion assay | T2 protospacer - 8N PAM library - chloramphenicol acetyltransferase | pbPOS T2 library | 31137 |
| pET9a | Expression and purification of OMNI proteins | T7 promoter - SV40 NLS - OMNI ORF (human optimized) - HA - SV40 NLS - 8 His-tag - T7 terminator | pET9a OMNI50-HisTag | 31138 |
| pmOMNI | Expressing OMNI polypeptide in the mammalian system | CMV promoter - Kozak - SV40 NLS - OMNI ORF (human optimized) - HA - SV40 NLS - P2A - mCherry - bGH poly(A) signal | pmOMNI OMNI39 | 31139 |
| pmGuide Endogenic site | Expressing OMNI sgRNA in the mammalian system | U6 promoter - Endogenic spacer sgRNA scaffold | pmGuide OMNI39 CXCR4 sgRNA V3 | 31140 |

T1
(SEQ ID NO: 31149)
GGTGCGGTTCACCAGGGTGTCG

T2
(SEQ ID NO: 31150)
ggAAGAGCagagccttGGTCTC

TABLE 4

| | | Guides | | | |
|---|---|---|---|---|---|
| | | OMNI-39 | OMNI-40 | OMNI-50 | OMNI-53 |
| crRNA:trac rRNA duplex V1 | lower + upper stem of crRNA | GUUUUAGUA CCUAGAG (SEQ ID NO: 31151) | GUUUUGUUA CCAUAUG (SEQ ID NO: 31161) | GUUUGAGAG UUAUG (SEQ ID NO: 31171) | GUUUGAGAA CCAUG (SEQ ID NO: 31182) |
| | upper + lower stem of tracrRNA | CUUUAGACC UACUAAAAU (SEQ ID NO: 31152) | UAUAUGACC UAACAAAAC (SEQ ID NO: 31162) | CAUGACGAG UUCAAAU (SEQ ID NO: 31172) | CAUGGUGAG UGCAAAU (SEQ ID NO: 31183) |
| crRNA:trac rRNA duplex V2 | lower + upper stem of crRNA | GUUUUAGUA CCUAGAGAA A (SEQ ID NO: 31153) | GUUUUGUUA CCAUAUGAU U (SEQ ID NO: 31163) | GUUUGAGAG UUAUGUAA (SEQ ID NO: 31173) | GUUUGAGAA CCAUGUAA (SEQ ID NO: 31184) |
| | upper + lower stem of tracrRNA | UUUCUUUAG ACCUACUAA AAU (SEQ ID NO: 31154) | AUUUAUAUG ACCUAACAA AAC (SEQ ID NO: 31164) | UUACAUGAC GAGUUCAAA U (SEQ ID NO: 31174) | UUACAUGGU GAGUGCAAA U (SEQ ID NO: 31185) |
| | tracrRNA (Nexus + hairpins) | AAGGCUUUA UGCCGAGAU UAAAGGAUG CCGACGGGC AUCcuuuuu u (SEQ ID NO: 31155) | AAGGGUUUA UCCCGGACU CGGCUCUUC GGAGCCUUU UU (SEQ ID NO: 31165) | AAAAAUUUA UUCAAACCG CCUAUUUAU AGGCCGCAG AUGUUCUGC AUUAUGCUU GCUAUUGCA AGCUUUUUU (SEQ ID NO: 31175) | AAGGAUUAU CCGAAAUUG UAUGCCCGC CAAUAAAAA GGCUCGAAA GAGUCUUUU U (SEQ ID NO: 31186) |
| | Nexus | GGCUUUAUG CC (SEQ ID NO: 31156) | GGGUUUAUC CC (SEQ ID NO: 31166) | GCCUAUUUA UAGGC (SEQ ID NO: 31176) | GGAUUAUCC UAGGC |
| | hairpin | AAGGAUGCC GACGGGCAU CCUUU (SEQ ID NO: 31157) | GGCUCUUCG GAGCC (SEQ ID NO: 31167) | GCAGAUGUU CUGCAUUAU GCUUGCUAU UGCAAGC (SEQ ID NO: 31177) | UGUAUGCCC GCAUUGUGC GGCAAUAAA AAGGCUCGA AAGAGUCUU U (SEQ ID NO: 31187) |
| | sgRNA V1 | GUUUUAGUA CCUAGAGga aaCUUUAGA CCUACUAAA AUAAGGCUU UAUGCCGAG UUCCGACGG GCAUCCUUU UUU (SEQ ID NO: 31158) | GUUUUGUUA CCAUAUGga aaUAUAUGA CCUAACAAA ACAAGGGUU UAUCCCGGA UCGGAGCCU UCGGAGCCU UUUU (SEQ ID NO: 31168) | GUUUGAGAG UUAUGgaaa CAUGACGAG UUCAAAUAA AAAUUUAUU CAAACCGCC UAUUUAUAG GCCGCAGAU GUUCUGCAU AUGCUUGC AAUUGCAAG CUUUUUU (SEQ ID NO: 31178) | GUUUGAGAA CCAUGgaaa CAUGGUGAG UGCAAAUAA GGAUUAUCC UAGGCCCGCAU UGUGCGGCA AUAAAAAGG CUCGAAAGA GUCUUUUU (SEQ ID NO: 31188) |
| | sgRNA V2 | GUUUUAGUA CCUAGAGAA AgaaaUUUC UUUAGACCU ACUAAAAUA | GUUUUGUUA CCAUAUGAU UgaaaAUUU AUAUGACCU AACAAAACA | GUUUGAGAG UUAUGUAAg aaaUUACAU GACGAGUUC AAAUAAAAA | GUUUGAGAA CCAUGUAAg aaaUUACAU GGUGAGUGC AAAUAAGGA |

TABLE 4-continued

| | | Guides | | | |
|---|---|---|---|---|---|
| | | OMNI-39 | OMNI-40 | OMNI-50 | OMNI-53 |
| | | AGGCUUUAU GCCGAGAUU AAAGGAUGC CGACGGGCA UCCUUUUUU (SEQ ID NO: 31159) | AGGGUUUAU CCCGGACUC GGCUCUUCG GAGCCUUUU U (SEQ ID NO: 31169) | UUUAUUCAA ACCGCCUAU UUAUAGGCC GCAGAUGUU CUGCAUUAU GCUUGCUAU UGCAAGCUU UUUU (SEQ ID NO: 31179) | UUAUCCGAA AUUGUAUGC CCGCAUUGU GCGGCAAUA AAAAGGCUC GAAAGAGUC UUUUU (SEQ ID NO: 31189) |
| Other variations | sgRNA V3 | GUUUAAGUA CCUAGAGAA AgaaaUUUC UUUAGACCU ACUUAAAUA AGGCUUUAU GCCGAGAUU AAAGGAUGC CGACGGGCA UCCUUUUUU (SEQ ID NO: 31160) | GUUUAGUUA CCAUAUGAU UgaaaAUUU AUAUGACCU AACUAAACA AGGGUUUAU CCCGGACUC GGCUCUUCG GAGCCUUUU U (SEQ ID NO: 31170) | GUUUGAGAG UUAUGUgaa aACAUGACG AGUUCAAAU AAAAAUUUA UUCAAACCG CCUAUUUAU AGGCCGCAG AUGUUCUGC AUUAUGCUU GCUAUUGCA AGCUUUUUU (SEQ ID NO: 31180) | |
| | sgRNA V4 | | | GUUUGAGAG UUAUGUAga aaUACAUGA CGAGUUCAA AUAAAAAUU UAUUCAAAC CGCCUAUUU AUAGGCCGC AGAUGUUCU GCAUUAUGC UUGCUAUUG CAAGCUUUU UU (SEQ ID NO: 31181) | |

TABLE 5

| | | PAMs | | | |
|---|---|---|---|---|---|
| | | OMNI-39 | OMNI-40 | OMNI-50 | OMNI-53 |
| Bacterial Depletion | PAM General | NNGYAD | NYGRV | | NRTA |
| | PAM Specific | NNGYAA | NYGAV | | NRTA |
| | Activity (1-Depletion score)* | 0.99 | 0.95 | | 1.00 |
| TXTL Depletion | PAM General | NNGHAD | NYGRV | NGG | NRHR |
| | PAM Specific | NNGYAA | NYGRV | NGG | NAWA |
| | Activity (1-Depletion score)* | 0.95 | 0.97 | 0.98 | 0.97 |
| | sgRNA | V2 | V2 | V2 | V2 |
| mammalian system | | | VTGAAG | NGG | NRTA |

*Depletion score - Average of the ratios from two most depleted sites
** Depends on OMNI expression and sgRNA transcription Bacterial PAM Depletion Assay.

To confirm that each of the identified loci are functional CRISPR-OMNI nuclease systems and to identify their PAMs, E. coli strain BW25141 (1DE3) was co-transformed with: (1) a library of plasmid pool containing a randomized PAM sequences of 8 N's flanking a unique protospacer (pbPOS T2 library, Table 3), (2) plasmids encoding E. coli codon-optimized OMNI nucleases, pbNNC2 (Table 3) and (3) a plasmid encoding designed sgRNA targeting the protospacer of the library or a non-targeting gRNA as control (pbGuide, T2 and T1 respectively, Table 3). Next, cells were selected for all three plasmids by recovering them on media containing appropriate antibiotics. In this this assay, plasmids containing a PAM are cleaved and the cells that contain them cannot grow, while cells containing plasmids with non-PAMs are able to propagate. A survived plasmid DNA pool was isolated, and the library was sequenced using a 75-cycle NextSeq kit (Illumina). PAM representation in the library was determined using a custom script and compared between OMNI and control. By comparing the frequency of a sequence in the library after selection of the targeting guide (T2) relative to the non-targeting (T1), individual PAM sequences could be identified. The presented data reflect a condensed 4N window library with all possible locations along the 8 bp sequence. Sequence motifs were generated using the Weblogo tool (weblogo.berkeley.edu). Activity of the OMNI nuclease was estimated based on the average of the two most depleted sequences and was calculated as: 1—Depletion score (Depletion score—Average of the ratios from two most depleted sites). OMNI nucleases with scores that are higher than 0.6 were considered as active. Following deep sequencing we detected depletion in the tested OMNI systems, indicating functional DNA interference in a heterologous host (Table 5).

In-Vitro Depletion Assay by TXTL.

Depletion of PAM sequences in-vitro was followed according to Maxwell et al, Methods. 2018. Briefly, linear DNA expressing the OMNI nucleases and the sgRNAs under a T7 promoter were added to a TXTL mix (Arbor Bioscience) together with a linear construct expressing T7 polymerase. RNA expression and protein translation by the TXTL mix results in the formation of the RNP complex. Since linear DNA was used, Chi6 sequences, a RecBCD inhibitor, were added to protect the DNA from degradation. The sgRNA spacer is designed to target a library of plasmids containing the targeting protospacer (pbPOS T2 library, Table 3) flanked by an 8N randomized set of potential PAM sequences. Depletion of PAM sequences from the library is measured by adding the adapters and indices necessary for high-throughput sequencing using PCR to both the cleaved library and to a control library expressing a non-targeting gRNA (T1). Following deep sequencing, the activity was confirmed in-vitro by depletion in 10 out of 10 tested OMNIs, showing similar PAM pattern as discovered in *E. coli* (Table 5). Thus, the in-vitro activity displayed by OMNI nucleases indicated functional DNA interference by in-vitro system (Table 5).

PAM Library in Mammalian System

While a PAM sequence preference is considered an inherent property of the nuclease, it might be effected, to some extent, from the cellular environment and genomic composition and size. Since the human cellular environment is significantly different from the bacterial one with respect to those properties, a "fine tuning" step was introduced to address potential differences in PAM preferences in human cellular context. To this end, a PAM library was constructed in human cell line. In this assay, The PAM library is introduced to the cells using a viral vector, as constant target sequence followed by a stretch of 6×N's. Upon introduction of OMNI and sgRNA targeting the library constant target site, NGS analysis is used to identify the edited sequences and the PAM associated with them. The enriched edited sequences are then used to define the PAM consensus. This method is applied to determine the "human" PAM requirements of OMNI nuclease (Table 5, "mammalian system"). OMNI-50 PAM is identical using TXTL or mammalian system. OMNI-53 PAM is a reduced version of the PAM identified by TXTL. On the other hand OMNI-40 show a more strict PAM compared with TXTL results. OMNI-39 PAM could not be determined using the mammalian system due to low number of editing events.

Expression of OMNI Nucleases Coded by an Optimized DNA Sequence in Mammalian Cells First, expression of each of the optimized DNA sequences coding for each of the OMNI proteins OMNI-39, OMNI-40, OMNI-50, and OMNI-53 in mammalian cells, was validated. To this end, an expression vector coding for an HA-tagged OMNI nuclease or *Streptococcus pyogenes* Cas9 (SpCas9) linked by P2A peptide to mCherry (pmOMNI, Table 3) was introduced into HeLa cells using the Jet-optimus transfection reagent (polyplus-transfection). P2A peptide is a self-cleaving peptide which can induce the cleaving of the recombinant protein in cell, such that the OMNI nucleases and the mCherry are separated upon expression and the mCherry can serve as indicator for transcription efficiency of the OMNI from the expression vector. The level of expression for each OMNI in the activity assays was determined using flow cytometry.

Activity in Human Cells on Endogenous Genomic Targets

OMNIs were also assayed for their ability to promote editing on specific genomic locations in human cells. To this end, per each OMNI the corresponding OMNI-P2A-mCherry expression vector (pmOMNI, Table 3) was transfected into HeLa cells together with sgRNA designed to target a specific location in the human genome (pmGuide, Table 3). At 72 h, cells were harvested, and half were used for quantification of transfection efficiency by FACS using mCherry fluorescence as marker. The rest of the cells were lysed, and their genomic DNA content was used in PCR reaction, amplifying the corresponding putative genomic targets. Amplicons were subjected to NGS and the resulting sequences were then used calculate the percentage of editing events in each target site. Short insertions or deletions (InDels) around the cut site are the typical outcome of repair of DNA ends following nuclease induced DNA cleavage. The calculation of % editing was therefore deduced from the fraction of Indels containing sequences within each amplicon. All editing values were normalized to the transfection and translation efficacy obtained for each experiment and deduced from the percentage of mCherry expressing cells. The normalized values represent the effective editing levels within the population of cells that expressed the nucleases.

Genomic activity of each OMNI was assessed using a panel of 4 to 11 unique sgRNA each design to target a different genomic location. The results of these experiments are summarized in Table 6. As can be seen in the table (column 6, "% editing"), all of the OMNIs exhibit high and significant editing levels compared to the negative control (column 9, "% editing in neg control") in all or most target site tested. OMNI-39 exhibited high and significant editing levels in 2/4 sites tested, OMNI-40 exhibit high and significant editing levels in 3/4 sites tested, OMNI50 exhibited high and significant editing levels in 11/11 sites tested, and OMNI-53 exhibited high and significant editing levels in 3/4 sites tested.

TABLE 6

Activity in human cells on endogenous genomic targets

| Nuclease | Genomic site | Corresponding Spacer name | Spacer sequence | 3' (PAM containing) genomic seq (PAM = Bold) | % indels | % transfection |
|---|---|---|---|---|---|---|
| OMNI-39 | CXCR4 site 1 | CXCR4g1_OMNI39 | CCAAGUG AUAAACA CGAGGA (SEQ ID NO: 31190) | TGGCAAGA | 49.8-73.2 | 67.13 |

TABLE 6-continued

| | | Activity in human cells on endogenous genomic targets | | | | |
|---|---|---|---|---|---|---|
| | EMX1 site 1 | EMX1g1_OMNI39 | GUCACCU CCAAUGA CUAGGGU (SEQ ID NO: 31191) | GGGCAACC | 3.9-6.3 | |
| | EMX1 site 2 | EMX1g2_OMNI39 | GCCGCCA UUGACAG AGGGAC (SEQ ID NO: 31192) | AAGCAATG | 22.8-54.7 | |
| | PDCD1 site 1 | PDCD1g1_OMNI39 | AACUGGU ACCGCAU GAGCCC (SEQ ID NO: 31193) | CAGCAACC | 3.71 | 73.67 |
| OMNI-40 | EMX1 site 1 | EMX1g1_OMNI40 | CAUCAGG CUCUCAG CUCAGC (SEQ ID NO: 31194) | CTGAGTGT | 25-37.5 | 50.33 |
| | CXCR4 site 2 | CXCR4g2_OMNI40 | AGGUGCC GUUUGUU CAUUUU (SEQ ID NO: 31195) | CTGACACT | 0.20 | 53.60 |
| | PDCD1 site 2 | PDCD1g1_OMNI40 | CCAGUUG UAGCACC GCCCAG (SEQ ID NO: 31196) | ACGACTGG | 23.59 | 28.33 |
| | PDCD1 site 3 | PDCD1g2_OMNI40 | UCUCCCC AGCCCUG CUCGUG (SEQ ID NO: 31197) | GTGACCGA | 16.66 | 49.00 |
| OMNI-50 | EMX1 site 2 | EMX1g1_OMNI50 | UCUGUGA AUGUUAG ACCCAU (SEQ ID NO: 31198) | GGGAGCAG | 44.18-25.72 | |
| | EMX1 site 3 | EMX1g2_OMNI50 | CCAUGGG AGCAGCU GGUCAG (SEQ ID NO: 31199) | AGGGGACC | 55.81 | |
| | CXCR4 site 3 | CXCR4g1_OMNI50 | GCAAGAG ACCCACA CACCGG (SEQ ID NO: 31200) | AGGAGCGC | 29.58-32.14 | |
| | CXCR4 site 4 | CXCR4g2_OMNI50 | ACACCGG AGGAGCG CCCGCU (SEQ ID NO: 31201) | TGGGGAG | 42.13-49.85 | |
| | PDCD1 site 4 | PDCD1g1_OMNI50 | CGUCUGG GCGGUGC UACAAC (SEQ ID NO: 31202) | TGGGCTGG | 13.35-8.7 | |

TABLE 6-continued

Activity in human cells on endogenous genomic targets

| | | | | | | |
|---|---|---|---|---|---|---|
| | PDCD1 site 5 | PDCD1g2_OMNI50 | CUACAAC UGGGCUG GCGGCC (SEQ ID NO: 31203) | AGGATGGT | 17.53 | |
| | ELANE g35 | ELANEg35_OMNI50 | AGUCCGG GCUGGGA GCGGGU (SEQ ID NO: 31204) | GGGGAGCA | 40.92-55.39 | |
| | ELANE g58 | ELANEg58_OMNI50 | GCUGCGG GAAAGGG AUUCCC (SEQ ID NO: 31205) | TGGGACTC | 11.11 | 20.50 |
| | ELANE g38 | ELANEg38_OMNI50 | ACAGCGG GUGUAGA CUCCGA (SEQ ID NO: 31206) | GGGGGACG | 9.99 | |
| | ELANE g39 | ELANEg39_OMNI50 | CAGCGGG UGUAGAC UCCGAG (SEQ ID NO: 31207) | GGGGACGT | 24.87 | |
| | ELANE g62 | ELANEg62_OMNI50 | GUCAAGC CCCAGAG GCCACA (SEQ ID NO: 31208) | GGGACAGA | 38.87-52.74 | |
| OMNI-53 | EMX1 site 4 | EMXg1_OMNI53 | GCCUGGG GCCCCUA ACCCUA (SEQ ID NO: 31209) | TGTAGCCT | 18.3-36.7 | 49.63 |
| | CXCR4 site 5 | CXCR4g2_OMNI53 | AUUUUCU GACACUC CCGCCC (SEQ ID NO: 31210) | AATATACC | 14.1-12.5 | 38.33 |
| | PDCD1 site 6 | PDCD1g1_OMNI53 | AUCCUGG CCGCCAG CCCAGU (SEQ ID NO: 31211) | TGTAGCAC | 11.5 | 51.27 |
| | PDCD1 site 7 | PDCD1g2_OMNI53 | GGAGAGC UUCGUGC UAAACU (SEQ ID NO: 31212) | GGTACCGC | 1.93 | 30.30 |

| Nuclease | Genomic site | Norm. % editing | % editing in neg control | % transfection in neg control | Norm. % editing in neg control |
|---|---|---|---|---|---|
| OMNI-39 | CXCR4 site 1 | | 0.08 | 76.70 | 0.107791557 |
| | EMX1 site 1 | | | | |
| | EMX1 site 2 | | | | |
| | PDCD1 site 1 | 5.03 | 0.07 | 76.70 | 0.086641622 |

TABLE 6-continued

Activity in human cells on endogenous genomic targets

| | | | | | |
|---|---|---|---|---|---|
| OMNI-40 | EMX1 site 1 | | 0.12 | 53.37 | 0.231979262 |
| | CXCR4 site 2 | 0.37 | 0.21 | 53.37 | 0.396940137 |
| | PDCD1 site 2 | 83.25 | 0.09 | 53.37 | 0.174121445 |
| | PDCD1 site 3 | 34.00 | 0.01 | 0.18 | 8.107932801 |
| OMNI-50 | EMX1 site 2 | | 0.02 | | |
| | EMX1 site 3 | | | | |
| | CXCR4 site 3 | | 0.18 | | |
| | CXCR4 site 4 | | 0.22 | | |
| | PDCD1 site 4 | | 0.05 | | |
| | PDCD1 site 5 | | | | |
| | ELANE g35 | | 0.24 | 5.95 | 3.982225429 |
| | ELANE g58 | 54.23 | 0.18 | 5.95 | 2.974553445 |
| | ELANE g38 | | | | |
| | ELANE g39 | | | | |
| | ELANE g62 | | 0.12 | 5.95 | 2.002503126 |
| OMNI-53 | EMX1 site 4 | | 0.15 | 43.80 | 0.333213614 |
| | CXCR4 site 5 | | 0.22 | 43.80 | 0.509942217 |
| | PDCD1 site 6 | 22.50 | 0.05 | 43.80 | 0.105935337 |
| | PDCD1 site 7 | 6.38 | 0.01 | 43.80 | 0.019429028 |

Intrinsic Fidelity in Human Cells

Figure 2:
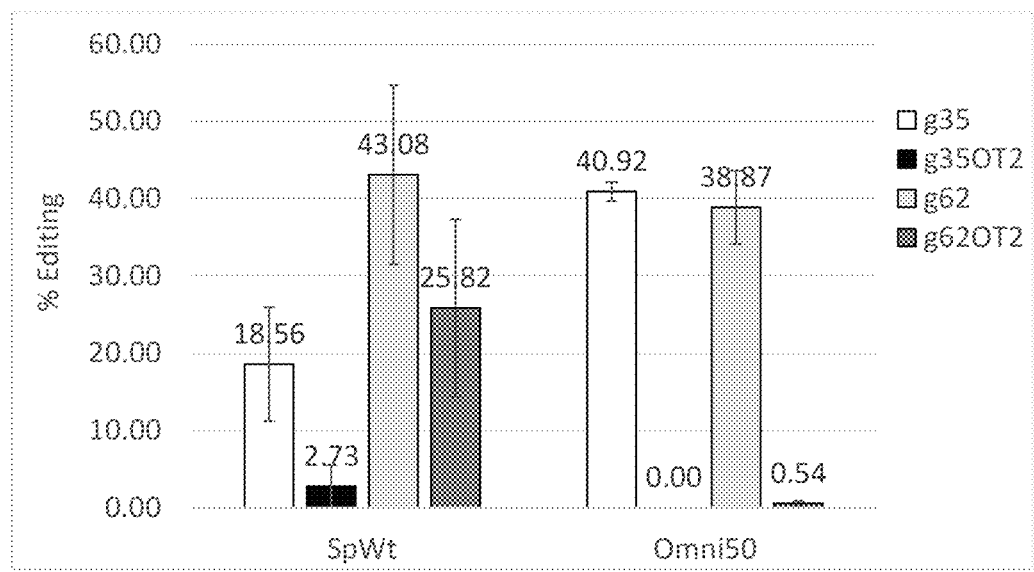
FIG. 2: Intrinsic fidelity in human cells. OMNI-50 or SpCas9 nuclease was expressed in a mammalian cell system by DNA transfection together with a sgRNA-expressing plasmid. Cell lysates were used for site specific genomic DNA amplification and NGS. The percentage of indels was measured and analyzed to compare on-target vs off-target editing in HeLa cell line using ELANEg35_OMNI50 or ELANEg62_OMNI50 (see Table 3). In both cases, the genomic On and Off target sequences are noted below the chart with the PAM sequence underlined. Each experiment represents three (3) independent repeats.

The intrinsic fidelity of a nuclease is a measure of its cleavage specificity. High fidelity nuclease is a nuclease that promotes cleavage on the intended target ("on-target") with minimal or no cleavage of the unintended target ("Off-target"). In CRISPR nucleases, the target is acquired based on sequence complementarity to the spacer element of the guide RNA. Off-targeting results from similarity of an unintended target to the spacer sequence. The intrinsic fidelity of OMNIs at the genomic level in human cells was measured by conducting an activity assay, followed by PCR amplification, NGS, and InDel analysis for both the on-target region and a pre-validated off target region. A measurement of intrinsic fidelity for OMNI-50 is provided in FIG. 2. In this example, OMNI-50 fidelity was measured using two guide RNAs independently, in each case a side by side measurement of SpCas9 is provided for reference. The first site was targeted using the ELANE g35 gRNA (Table 6) which has a defined on-target site upstream to the ELANE gene on chr19 and an off-target site on chr15. As can be seen in FIG. 2, the on/off target editing efficiency ratio obtained by OMNI-50 was 41:0 while SpCas9 on/off ratio is 6.8:1 (40.9%/0%; 18.6%/2.7% respectively). The second site was targeted by ELANE g62 gRNA (Table 6). This gRNA spacer sequence has a defined on-target at the ELANE gene on chr19 and an off-target site on chr1. In this case, the On/Off ratio obtained by OMNI-50 was 72:1 compared to 1.7:1 ratio obtained by SpCas9 (38.9%/0.6%; 43.1%/25.8% respectively). These results demonstrate that OMNI-50 has a significantly higher intrinsic fidelity in comparison to SpCas9 in human cellular environment.

Purification of OMNIs Protein.

The OMNI-50 open-reading frame was cloned into bacterial expression plasmids (T7-NLS-OMNI-NLS-HA-His-tag, pET9a, Table 3) and expressed in C43 cells (Lucigen). Cells were grown in Terrific Broth to mid-log phase and the temperature was lowered to 18° C. Expression was induced at 0.6 OD with 1 mM IPTG for 16-20 h before harvesting and freezing cells at −80° C. Cell paste was resuspended in lysis buffer (50 mM $NaH_2PO_4$, 300 mM NaCl, 10 mM imidazole pH8.0, 1 mM TCEP) supplemented with EDTA-free complete protease inhibitor cocktail set III (Calbiochem). Cells were lysed using sonication and cleared lysate was incubated with Ni-NTA resin. The resin was loaded onto gravity column and washed with wash buffer (50 mM $NaH_2PO_4$, 300 mM NaCl, 50 mM imidazole pH8.0, 1 mM TCEP) and OMNI protein eluted with wash buffer supplemented with 100-500 mM Imidazole. Fractions containing OMNI protein were pooled and concentrated and loaded onto a centricone (Amicon Ultra 15 ml 100K, Merck), and buffer exchanged to GF buffer (50 mM Tris-HCl pH 7.5, 500 mM NaCl, 10% glycerol, 0.4M Arginine). The concentrated OMNI protein was further purified by SEC on HiLoad 16/600 Superdex 200 µg-SEC, AKTA Pure (GE Healthcare Life Sciences) with a 50 mM Tris-HCl pH 7.5, 500 mM NaCl, 10% glycerol, 0.4M Arginine. Fractions containing OMNI protein were pooled and concentrated and loaded onto a centricone (Amicon Ultra 15 ml 100K, Merck) with a final storage buffer of 10 mM Tris-HCl, pH 7.5, 150 mM NaCl, 10% glycerol and 1 mM TCEP. Purified OMNI protein was concentrated to 10 mg/ml stocks and flash-frozen in liquid nitrogen and stored at −80° C.

Guide Optimization by RNP Activity Assay.

Figure 3A:
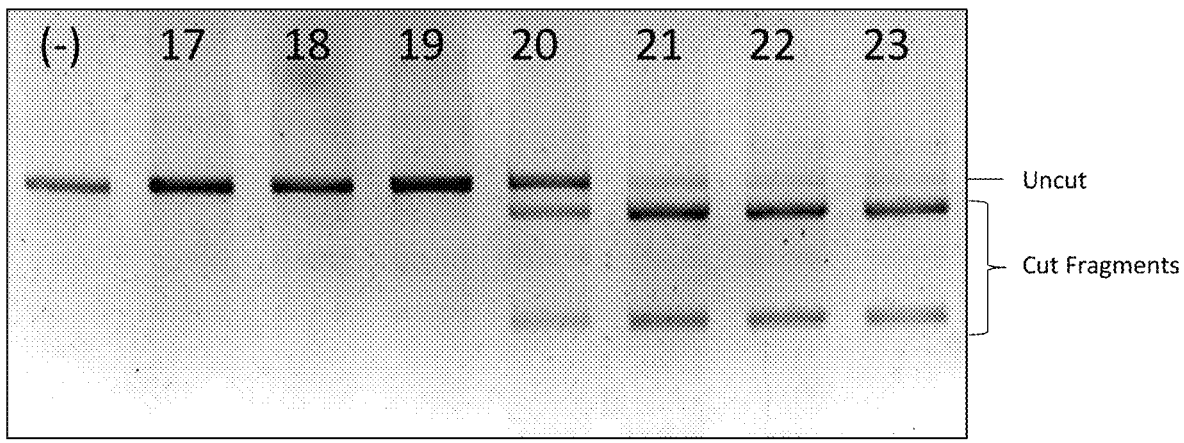
FIGS. 3A-3D: OMNI-50 activity Assay as RNP. OMNI-50 nuclease was over-expressed and purified. The purified protein was complexed with synthetic sgRNA to form RNPs. For the in-vitro assays (FIG. 3A and FIG. 3B) RNPs were incubated with a linear DNA template with the corresponding target and PAM sequences (listed in Table 5). Activity was verified by the ability to cleave the linear template. For the in-vivo assays (FIG. 3C and FIG. 3D) U2OS cells were electroporated with RNP, and activity was determined as indel frequency by NGS.
Figure 3B:
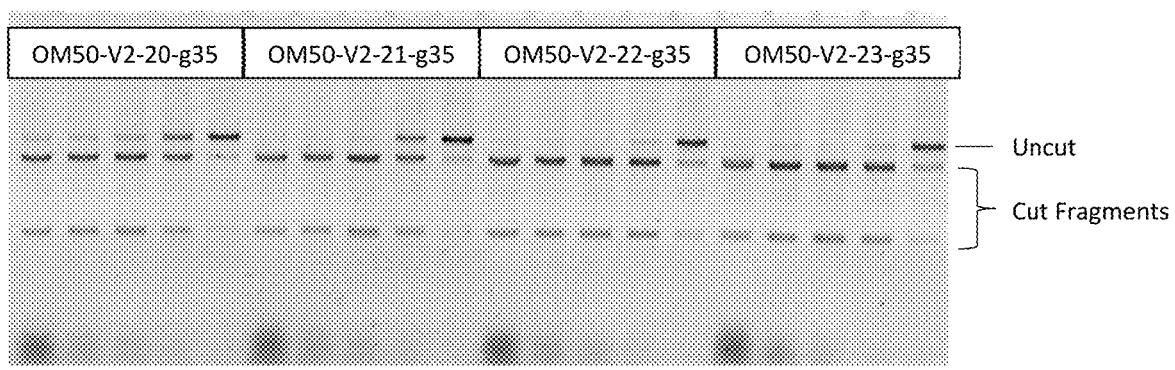

Synthetic sgRNAs of OMNI-50 were synthesized with three 2'-O-methyl 3'-phosphorothioate at the 3' and 5' ends (Agilent). Activity assay of OMNI-50 RNP with different spacer lengths (17-23 nucleotides) of guide 35 (Table 7, FIG. 3A). Briefly, 4 pmol of OMNI-50 nuclease were mixed with 6 pmol of synthetic guide. After 10 min of incubation at room-temp, the RNP complexes were reacted with 100 ng template of On-target. Only spacer larger than 22 nucleotides show near full cleavage of the On-target template. Furthermore, reducing amounts of RNPs (4, 2, 1.2, 0.6 and 0.2 pmol) with spacer lengths 20-23 were reacted with 100 ng DNA target template (FIG. 3B) Spacer at lengths of 22 nucleotides showed better cleavage activity even at lower RNP concentrations.

TABLE 7

| | synthetic sgRNA (RNP) | | |
|---|---|---|---|
| | Name | | |
| | O50_ELANE_V2_g35_23 | O50_ELANE_V2_g35_22 | O50_ELANE_V2_g35_21 |
| Spacer | UgcAGUCCGGGCUGGGAGCGGGU (SEQ ID NO: 31213) | gcAGUCCGGGCUGGGAGCGGGU (SEQ ID NO: 31217) | cAGUCCGGGCUGGGAGCGGGU(SEQ ID NO: 31219) |
| Scaffold | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 31179) | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 31179) | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 31179) |
| Version | V2 | V2 | V2 |
| Full sgRNA sequence | UgcAGUCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 31214) | gcAGUCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 31218) | cAGUCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 31220) |

TABLE 7-continued

| | synthetic sgRNA (RNP) | | |
|---|---|---|---|
| Protospacer (with PAM = Bold) - On target | CTGTTGCTG CAGTCCGGG CTGGGAGCG GGTGGGGAG CAGAGGG (SEQ ID NO: 31215) | CTGTTGCTG CAGTCCGGG CTGGGAGCG GGTGGGGAG CAGAGGG (SEQ ID NO: 31215) | CTGTTGCTG CAGTCCGGG CTGGGAGCG GGTGGGGAG CAGAGGG (SEQ ID NO: 31215) |
| Protospacer (with PAM = Bold) - Off target | GTTAAGA*ga* CAGTCC*a*GG CTGGGAGC*a* GGTGGGGAG AGGAGGG (SEQ ID NO: 31216) | GTTAAGA*ga* CAGTCC*a*GG CTGGGAGC*a* GGTGGGGAG AGGAGGG (SEQ ID NO: 31216) | GTTAAGA*ga* CAGTCC*a*GG CTGGGAGC*a* GGTGGGGAG AGGAGGG (SEQ ID NO: 31216) |

| | Name | |
|---|---|---|
| | O50_ELANE_V2_g35_20 | O50_ELANE_V2_g35_19 |
| Spacer | AGUCCGGGC UGGGAGCGG GU (SEQ ID NO: 31221) | GUCCGGGCU GGGAGCGGG U (SEQ ID NO: 31223) |
| Scaffold | gUUUGAGAG UUAUGUAAg aaaUUACAU GACGAGUUC AAAUAAAAA UUUAUUCAA ACCGCCUAU UUAUAGGCC GCAGAUGUU CUGCAUUAU GCUUGCUAU UGCAAGCUU UUUU (SEQ ID NO: 31179) | gUUUGAGAG UUAUGUAAg aaaUUACAU GACGAGUUC AAAUAAAAA UUUAUUCAA ACCGCCUAU UUAUAGGCC GCAGAUGUU CUGCAUUAU GCUUGCUAU UGCAAGCUU UUUU (SEQ ID NO: 31179) |
| Version | V2 | V2 |
| Full sgRNA sequence | AGUCCGGGC UGGGAGCGG GUgUUUGAG AGUUAUGUA AgaaaUUAC AUGACGAGU UCAAAUAAA AAUUUAUUC AAACCGCCU AUUUAUAGG CCGCAGAUG UUCUGCAUU AUGCUUGCU AUUGCAAGC UUUUUU (SEQ ID NO: 31222) | GUCCGGGCU GGGAGCGGG UgUUUGAGA GUUAUGUAA gaaaUUACA UGACGAGUU CAAAUAAAA AUUUAUUCA AACCGCCUA UUUAUAGGC CGCAGAUGU UCUGCAUUA UGCUUGCUA UUGCAAGCU UUUU (SEQ ID NO: 31224) |
| Protospacer (with PAM = Bold) - On target | CTGTTGCTG CAGTCCGGG CTGGGAGCG GGTGGGGAG CAGAGGG (SEQ ID NO: 31215) | CTGTTGCTG CAGTCCGGG CTGGGAGCG GGTGGGGAG CAGAGGG (SEQ ID NO: 31215) |
| Protospacer (with PAM = Bold) - Off target | GTTAAGA*ga* CAGTCC*a*GG CTGGGAGC*a* GGTGGGGAG AGGAGGG (SEQ ID NO: 31216) | GTTAAGA*ga* CAGTCC*a*GG CTGGGAGC*a* GGTGGGGAG AGGAGGG (SEQ ID NO: 31216) |

TABLE 7-continued

| | synthetic sgRNA (RNP) | |
|---|---|---|
| | Name | |
| | O50_ELANE_V2_g35_18 | O50_ELANE_V2_g35_17 |
| Spacer | UCCGGGCUGGG AGCGGGU (SEQ ID NO: 31225) | CCGGGCUGGGA GCGGGU (SEQ ID NO: 31227) |
| Scaffold | gUUUGAGAGUU AUGUAAgaaaU UACAUGACGAG UUCAAAUAAAA AUUUAUUCAAA CCGCCUAUUUA UAGGCCGCAGA UGUUCUGCAUU AUGCUUGCUAU UGCAAGCUUUU UU (SEQ ID NO: 31179) | gUUUGAGAGUU AUGUAAgaaaU UACAUGACGAG UUCAAAUAAAA AUUUAUUCAAA CCGCCUAUUUA UAGGCCGCAGA UGUUCUGCAUU AUGCUUGCUAU UGCAAGCUUUU UU (SEQ ID NO: 31179) |
| Version | V2 | V2 |
| Full sgRNA sequence | UCCGGGCUGGG AGCGGGUgUUU GAGAGUUAUGU AAgaaaUUACA UGACGAGUUCA AAUAAAAAUUU AUUCAAACCGC CUAUUUAUAGG CCGCAGAUGUU CUGCAUUAUGC UUGCUAUUGCA AGUUUUU (SEQ ID NO: 31226) | CCGGGCUGGGA GCGGGUgUUUG AGAGUUAUGUA AgaaaUUACAU GACGAGUUCAA AUAAAAAUUUA UUCAAACCGCC UAUUUAUAGGC CGCAGAUGUUC UGCAUUAUGCU UGCUAUUGCAA GCCUUUUUU (SEQ NO: ID 31228) |
| Protospacer (with PAM = Bold) - On target | CTGTTGCTGCA GTCCGGGCTGG GAGCGGGTGGG GAGCAGAGGG (SEQ ID NO: 31215) | CTGTTGCTGCA GTCCGGGCTGG GAGCGGGTGGG GAGCAGAGGG (SEQ ID NO: 31215) |
| Protospacer (with PAM = Bold) - Off target | GTTAAGA*ga*CA GTCC*a*GGCTGG GAGC*a*GGTGGG GAGAGGAGGG (SEQ ID NO: 31216) | GTTAAGA*ga*CA GTC*a*GGCTGG GAGC*a*GGTGGG GAGAGGAGGG (SEQ ID NO: 31216) |

| | Name | |
|---|---|---|
| | O50_ELANE_V3_g35_20 | O50_ELANE_V4_g35_20 |
| Spacer | AGUCCGGGCUG GGAGCGGGU (SEQ ID NO: 31221) | AGUCCGGGCUG GGAGCGGGU (SEQ ID NO: 31221) |
| Scaffold | gUUUGAGAGUU AUGUgaaaACA UGACGAGUUCA AAUAAAAAUUU AUUCAAACCGC CUAUUUAUAGG CCGCAGAUGUU CUGCAUUAUGC UUGCUAUUGCA AGCUUUUUU (SEQ ID NO: 31180) | gUUUGAGAGUU AUGUAgaaaUA CAUGACGAGUU CAAAUAAAAAU UUAUUCAAACC GCCUAUUUAUA GGCCGCAGAUG UUCUGCAUUAU GCUUGCUAUUG CAAGCUUUUUU (SEQ ID NO: 31181) |

TABLE 7-continued synthetic sgRNA (RNP)

| Version | V3 | V4 |
|---|---|---|
| Full sgRNA sequence | AGUCCGGGCUG GGAGCGGGUgU UUGAGAGUUAU GUgaaaACAUG ACGAGUUCAAA UAAAAAUUUAU UCAAACCGCCU AUUUAUAGGCC GCAGAUGUUCU GCAUUAUGCUU GCUAUUGCAAG CUUUUUUU (SEQ ID NO: 31229) | AGUCCGGGCUG GGAGCGGGUgU UUGAGAGUUAU GUAgaaaUACA UGACGAGUUCA AAUAAAAAUUU AUUCAAACCGC CUAUUUAUAGG CCGCAGAUGUU CUGCAUUAUGC UUGCUAUUGCA AGCUUUUUU (SEQ ID NO: 31230) |
| Protospacer (with PAM = Bold) - On target | CTGTTGCTGCA GTCCGGGCTGG GAGCGGGTGGG GAGCAGAGGG (SEQ ID NO: 31215) | CTGTTGCTGCA GTCCGGGCTGG GAGCGGGTGGG GAGCAGAGGG (SEQ ID NO: 31215) |
| Protospacer (with PAM = Bold) - Off target | GTTAAGA*ga*CA GTCC*a*GGCTGG GAGC*a*GGTGGG GAGAGGAGGG (SEQ ID NO: 31216) | GTTAAGA*ga*CA GTCC*a*GGCTGG GAGC*a*GGTGGG GAGAGGAGGG (SEQ ID NO: 31216) |

Figure 3C:
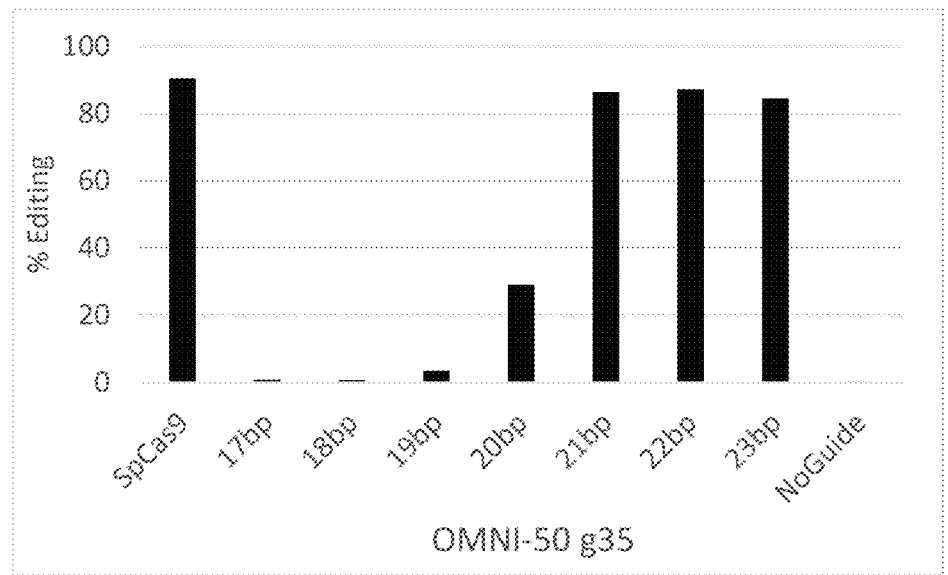

Spacer length optimization was also performed in a cell line context. RNPs were assembled by mixing 100 uM nuclease with 120 uM of synthetic guide with different spacer length (17-23 nt, Table 4) (and 100 uM Cas9 electroporation enhancer (IDT). After 10 mins of incubation at room temperature, the RNP complexes were mixed with 200,000 pre-washed U2OS cells and electroporated using Lonza SE Cell Line 4D-Nucleofector™ X Kit with the DN100 program, according to the manufacturer's protocol. At 72 h cells were lysed, and their genomic DNA content was used in a PCR reaction to amplify the corresponding putative genomic targets. Amplicons were subjected to NGS and the resulting sequences were then used to calculate the percentage of editing events. As can be seen in FIG. 3C, spacers of 17-19 nt show low editing levels, 20 nt spacer shows medium editing levels, and spacers of 21-23 nt show the highest editing levels.

Figure 3D:
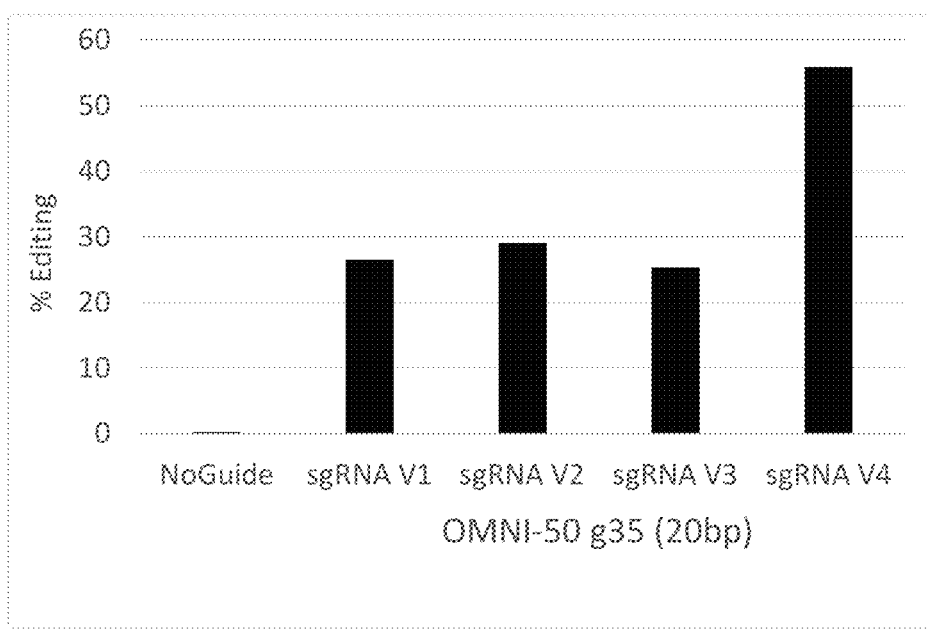

Using the same cell line context, we also tested different versions of tracer RNA modifications (Table 7). The different versions of sgRNA were tested with a 20 nt spacer. As can be seen in FIG. 3D, RNP assembly using either sgRNA V1, V2, and V3 results in similar editing levels. However, RNP assembly using sgRNA V4 results in significantly higher editing level.

Figure 4:
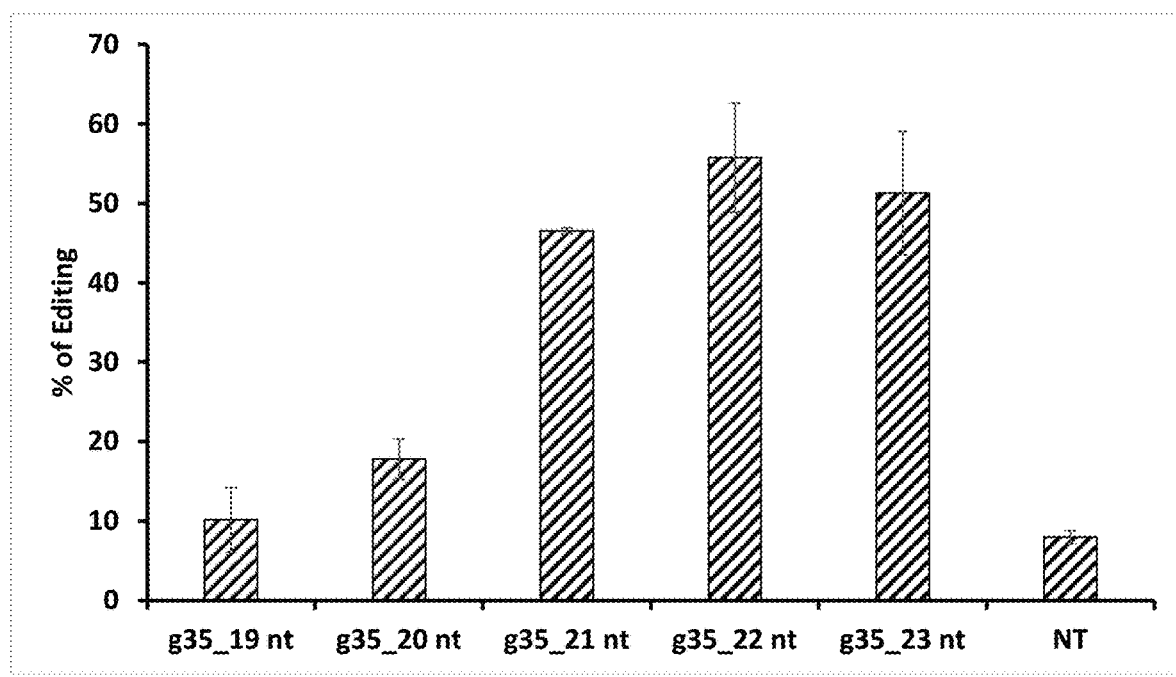
FIG. 4. Activity assay for OMNI-50 as RNP in iPSCs: RNPs with spacer lengths 17-23 nucleotides (Table 4) were electroporated into an iPSC cell line and editing levels (indels) were measured by NGS.

OMNI-50 guide length effects on editing efficacy were also tested in iPSC. Cells were nucleofected with OMNI-50 RNP complexes containing guides of different spacer length (17-23 nt, Table 4). Cells were harvested 72 h post nucleofection, gDNA was used for site specific genomic DNA amplification and capillary gel electrophoresis analysis using sg35 on-target primers which amplify the endogenous genomic region within the target gene. The capillary gel electrophoresis data was used to determine the Total % Editing. As can be seen in FIG. 4, a spacer length of 19 nt showed levels of editing similar to background (NT), 20 nt spacers resulted in medium editing levels, and 21-23 nt spacers resulted in the most significant editing levels, in agreement with the in vitro and the U2OS experiment described above.

EXAMPLE: ELANE Mutant Targeting Analysis

Guide sequences comprising 17-30 contiguous nucleotides containing nucleotides in the sequence set forth in any one of SEQ ID NOs: 1-31117 are screened for high on target activity using SpCas9 in HeLa cells. On target activity is determined by DNA capillary electrophoresis analysis.

REFERENCES

1. Ahmad and Allen (1992) "Antibody-mediated Specific Binging and Cytotoxicity of Lipsome-entrapped Doxorubicin to Lung Cancer Cells in Vitro", Cancer Research 52:4817-20
2. Anders (1992) "Human gene therapy", Science 256:808-13
3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200
4. Behr (1994) Gene transfer with synthetic cationic amphiphiles: Prospects for gene therapy", Bioconjuage Chem 5:382-89
5. Blaese (1995) "Vectors in cancer therapy: how will they deliver", Cancer Gene Ther. 2:291-97
6. Blaese et al. (1995) "T lympocyte-directed gene therapy for ADA-SCID: initial trial results after 4 years", Science 270(5235):475-80
7. Boxer, L. A. (2012) "How to approach neutropenia", Hematology Am Soc Hematol Educ Program 2012: 174-182
8. Buchschacher and Panganiban (1992) "Human immunodeficiency virus vectors for inducible expression of foreign genes", J. Virol. 66:2731-39

9. Burstein et al. (2017) "New CRISPR-Cas systems from uncultivated microbes", Nature 542:237-41

10. Carlsson, G et al. (2012) "Incidence of severe congenital neutropenia in Sweden and risk of evolution to myelodysplastic syndrome/leukaemia", Br J Haematol 158(3): 363-369

11. Chung et al. (2006) "*Agrobacterium* is not alone: gene transfer to plants by viruses and other bacteria", Trends Plant Sci. 11(1):1-4

12. Connelly, J. A. et al. (2012) "Hematopoietic stem cell transplantation for severe congenital neutropenia", Curr Opin Hematol 19(1): 44-51

13. Crystal (1995) "Transfer of genes to humans: early lessons and obstacles to success", Science 270(5235): 404-10

14. Dale, D. C. (2017) "How I manage children with neutropenia", Br J Haematol 178(3): 351-363

15. Dillon (1993) "Regulation gene expression in gene therapy" Trends in Biotechnology 11(5):167-173

16. Donadieu, J. et al. (2011) "Congenital neutropenia: diagnosis, molecular bases and patient management", Orphanet J Rare Dis 6: 26.

17. Dranoff et al. (1997) "A phase I study of vaccination with autologous, irradiated melanoma cells engineered to secrete human granulocyte macrophage colony stimulating factor", Hum. Gene Ther. 8(1):111-23

18. Donadieu et al. (2011) "Congenital neutropenia: diagnosis, molecular bases and patient management", Orphanet J Rare Dis. 6:26

19. Dunbar et al. (1995) "Retrovirally marked CD34-enriched peripheral blood and bone marrow cells contribute to long-term engraftment after autologous transplantation", Blood 85:3048-57

20. Ellem et al. (1997) "A case report: immune responses and clinical course of the first human use of ganulocyte/macrophage-colony-stimulating-factor-tranduced autologous melanoma cells for immunotherapy", Cancer Immunol Immunother 44:10-20

21. Gao and Huang (1995) "Cationic liposome-mediated gene transfer" Gene Ther. 2(10):710-22

22. Germeshausen et al. (2013) "The spectrum of ELANE mutations and their implications in severe congenital and cyclic neutropenia", Hum Mutat. 34(6):905-14

23. Haddada et al. (1995) "Gene Therapy Using Adenovirus Vectors", in: The Molecular Repertoire of Adenoviruses III: Biology and Pathogenesis, ed. Doerfler and Bohm, pp. 297-306

24. Han et al. (1995) "Ligand-directed retro-viral targeting of human breast cancer cells", Proc Natl Acad Sci U.S.A. 92(21):9747-51

25. Horwitz, M. S. et al. (2013) "ELANE mutations in cyclic and severe congenital neutropenia: genetics and pathophysiology", Hematol Oncol Clin North Am 27(1): 19-41, vii.

26. Inaba et al. (1992) "Generation of large numbers of dendritic cells from mouse bone marrow cultures supplemented with granulocyte/macrophage colony-stimulating factor", J Exp Med. 176(6):1693-702

27. Jinek et al. (2012) "A programmable dual-RNA-guided DNA endonuclease in adaptive bacterial immunity," Science 337(6096):816-21

28. Johan et al. (1992) "GLVR1, a receptor for gibbon ape leukemia virus, is homologous to a phosphate permease of *Neurospora crassa* and is expressed at high levels in the brain and thymus", J Virol 66(3):1635-40

29. Judge et al. (2006) "Design of noninflammatory synthetic siRNA mediating potent gene silencing in vivo", Mol Ther. 13(3):494-505

30. Kohn et al. (1995) "Engraftment of gene-modified umbilical cord blood cells in neonates with adnosine deaminase deficiency", Nature Medicine 1:1017-23

31. Koonen et al. (2017) "Diversity, classification and evolution of CRIPR-Cas systems", Current Opinion in Microbiology 37:67-78

32. Kremer and Perricaudet (1995) "Adenovirus and adeno-associated virus mediated gene transfer", Br. Med. Bull. 51(1):31-44

33. Macdiarmid et al. (2009) "Sequential treatment of drug-resistant tumors with targeted minicells containing siRNA or a cytotoxic drug", Nat Biotehcnol. 27(7):643-51

34. Malech et al. (1997) "Prolonged production of NADPH oxidase-corrected granulocyes after gene therapy of chronic granulomatous disease", PNAS 94(22):12133-38

35. Makaran et al. (2015) "The diversity of mutations and clinical outcomes for ELANE-associated neutropenia", Curr Opin Hematol. 22(1):3-11

36. Miller et al. (1991) "Construction and properties of retrovirus packaging cells based on gibbon ape leukemia virus", J Virol. 65(5):2220-24

37. Miller (1992) "Human gene therapy comes of age", Nature 357:455-60

38. Mitani and Caskey (1993) "Delivering therapeutic genes—matching approach and application", Trends in Biotechnology 11(5):162-66

39. Nabel and Feigner (1993) "Direct gene transfer for immunotherapy and immunization", Trends in Biotechnology 11(5):211-15

40. Remy et al. (1994) "Gene Transfer with a Series of Lipphilic DNA-Binding Molecules", Bioconjugate Chem. 5(6):647-54

41. Rosenberg, P. S. et al. (2010) "Stable long-term risk of leukaemia in patients with severe congenital neutropenia maintained on G-CSF therapy", Br J Haematol 150(2): 196-199.

42. Schaffer, A et al. (2007) "Genetic heterogeneity in severe congenital neutropenia: how many aberrant pathways can kill a neutrophil?" Curr Opin Allergy Clin Immunol 7(6): 481-494

43. Sentmanat et al. (2018) "A Survey of Validation Strategies for CRISPR-Cas9 Editing", Scientific Reports 8:888, doi:10.1038/s41598-018-19441-8

44. Skokowa, J. et al. (2017) "Severe congenital neutropenias", Nat Rev Dis Primers 3: 17032

45. Sommerfelt et al. (1990) "Localization of the receptor gene for type D simian retroviruses on human chromosome 19", J. Virol. 64(12):6214-20

46. Van Brunt (1988) "Molecular framing: transgenic animals as bioactors" Biotechnology 6:1149-54

47. Vigne et al. (1995) "Third-generation adenovectors for gene therapy", Restorative Neurology and Neuroscience 8(1,2): 35-36

48. Wilson et al. (1989) "Formation of infectious hybrid virion with gibbon ape leukemia virus and human T-cell leukemia virus retroviral envelope glycoproteins and the gag and pol proteins of Moloney murine leukemia virus", J. Virol. 63:2374-78

49. Yu et al. (1994) "Progress towards gene therapy for HIV infection", Gene Ther. 1(1):13-26

50. Yu, K et al. (2016) "Gene Editing of Human Hematopoietic Stem and Progenitor Cells: Promise and Potential Hurdles", Hum Gene Ther 27(10): 729-740
51. Zetsche et al. (2015) "Cpf1 is a single RNA-guided endonuclease of a class 2 CRIPSR-Cas system" Cell 163(3):759-71
52. Zhenwang et al. (2017) "Large-scale ex vivo generation of human neutrophils from cord blood CD34$^+$ cells", PLOS ONE, doi.org/10.1371/journal.pone.0180832
53. Zuris et al. (2015) "Cationic lipid-mediated delivery of proteins enables efficient protein based genome editing in vitro and in vivo" Nat Biotechnol. 33(1):73-80

SEQUENCE LISTING

The patent contains a lengthy sequence listing. A copy of the sequence listing is available in electronic form from the USPTO web site (https://seqdata.uspto.gov/?pageRequest=docDetail&DocID=US12258599B2). An electronic copy of the sequence listing will also be available from the USPTO upon request and payment of the fee set forth in 37 CFR 1.19(b)(3).

The invention claimed is:

1. An ex vivo or in vitro method of modifying in a cell a mutant allele of the elastase, neutrophil expressed (ELANE) gene wherein the mutant allele has a mutation associated with severe congenital neutropenia (SCN) or cyclic neutropenia (CyN), the method comprising introducing to the cell a composition comprising:
   (a) a CRISPR nuclease, or a DNA polynucleotide encoding said CRISPR nuclease, wherein said CRISPR nuclease comprises:
      (i) the amino acid sequence of SEQ ID NO: 31123, 31124, 31125, or 31126; or
      (ii) the amino acid sequence encoded by the nucleotide sequence of SEQ ID NO: 31131 or 31132; and
   (b) a first RNA molecule, or a DNA polynucleotide encoding the first RNA molecule, wherein said first RNA molecule comprises:
      (i) a CRISPR RNA (crRNA) molecule and a transactivating CRISPR RNA (tracrRNA) molecule; or
      (ii) a single-guide RNA (sgRNA) molecule,
      wherein the first RNA molecule comprises (I) a guide sequence portion comprising 20, 21, or 22 contiguous nucleotides of the sequence set forth in SEQ ID NO: 5519; or (II) a guide sequence portion comprising SEQ ID NO: 5469, 5482, or 5519, wherein the CRISPR nuclease and the first RNA molecule form a complex, and wherein said complex binds to the mutant allele of the ELANE gene and introduces a double strand break in the mutant allele of the ELANE gene.

2. The method of claim 1, further comprising introduction of a second RNA molecule, or a DNA polynucleotide encoding the second RNA molecule, wherein the second RNA molecule comprises (i) a crRNA molecule and a tracrRNA molecule or (ii) an sgRNA molecule,
   wherein the second RNA molecule and the CRISPR nuclease form a complex, and
   wherein the complex of the second RNA molecule and CRISPR nuclease introduces a second double strand break in the mutant allele of the ELANE gene.

3. The method of claim 2, wherein the second double strand break is within a non-coding region of the ELANE gene.

4. The method of claim 1, comprising obtaining a cell with a mutant allele of the ELANE gene associated with severe congenital neutropenia (SCN) or CyN from a subject with a mutant allele of the ELANE gene associated with SCN or CyN and/or suffering from SCN or CyN.

5. The method of claim 4, comprising obtaining the cell from the subject by (i) mobilization and apheresis, (ii) apheresis, (iii) mobilization, or (iv) bone marrow aspiration.

6. The method of claim 4, wherein a cytokine is introduced to the cell prior to introducing the composition to the cell.

7. The method of claim 4, wherein the cell is expanded by culturing the cell to obtain a larger quantity of the cells, and wherein the cells are cultured with one or more of: stem cell factor (SCF), interleukin 3 (IL-3), and granulocyte-macrophage colony-stimulating factor (GM-CSF);
   wherein the cells are cultured with at least one cytokine.

8. The method of claim 7, wherein the at least one cytokine is a recombinant human cytokine.

* * * * *